United States Patent
Vandenbroucke et al.

(10) Patent No.: US 10,988,770 B2
(45) Date of Patent: Apr. 27, 2021

(54) POLYCISTRONIC EXPRESSION SYSTEM FOR BACTERIA

(71) Applicant: INTREXON ACTOBIOTICS NV, Zwijnaarde (BE)

(72) Inventors: Klaas Vandenbroucke, De Pinte (BE); Karolien Van Huynegem, Asper (BE); Lothar Steidler, Lokeren (BE)

(73) Assignee: INTREXON ACTOBIOTICS NV, Zwijnaarde (BE)

( * ) Notice: Subject to any disclaimer, the term of this patent is extended or adjusted under 35 U.S.C. 154(b) by 40 days.

(21) Appl. No.: 15/897,427

(22) Filed: Feb. 15, 2018

(65) Prior Publication Data

US 2018/0187203 A1 Jul. 5, 2018

Related U.S. Application Data

(62) Division of application No. 14/122,545, filed as application No. PCT/EP2012/060431 on Jun. 1, 2012, now Pat. No. 9,920,324.

(30) Foreign Application Priority Data

Jun. 1, 2011 (EP) .................................. 11168495
Jul. 12, 2011 (EP) .................................. 11173588

(51) Int. Cl.
   *C12N 15/74* (2006.01)
(52) U.S. Cl.
   CPC .......... *C12N 15/746* (2013.01); *C12N 15/74* (2013.01)
(58) Field of Classification Search
   None
   See application file for complete search history.

(56) References Cited

U.S. PATENT DOCUMENTS

| | | | |
|---|---|---|---|
| 4,518,584 A | 5/1985 | Mark et al. |
| 4,564,593 A | 1/1986 | Tsukamoto et al. |
| 4,752,585 A | 6/1988 | Koths et al. |
| 4,919,918 A | 4/1990 | Cole et al. |
| 5,223,285 A | 6/1993 | DeMichele et al. |
| 5,229,109 A | 7/1993 | Grimm et al. |
| 5,470,561 A | 11/1995 | Klugkist et al. |
| 5,559,007 A | 9/1996 | Suri et al. |

(Continued)

FOREIGN PATENT DOCUMENTS

| | | |
|---|---|---|
| EP | 88195 A2 | 9/1983 |
| EP | 91539 A1 | 10/1983 |

(Continued)

OTHER PUBLICATIONS

Wu et al., Enhanced Secretory Production of a Single-Chain Antibody Fragment from Bacillus subtilis by Coproduction of Molecular Chaperones. J Bacteriology, 1998, 180:2830-2835 (Year: 1998).*

(Continued)

*Primary Examiner* — Arthur S Leonard
(74) *Attorney, Agent, or Firm* — Faegre Drinker Biddle & Reath LLP

(57) ABSTRACT

The invention relates to polycistronic expression in gram-positive bacterium and in particular concerns polycistronic expression units comprising one or more gene endogenous to the gram-positive bacterium transcriptionally coupled to one or more genes exogenous to the bacterium.

44 Claims, 20 Drawing Sheets

Specification includes a Sequence Listing.

sAGX0090 dual cistron

(56) References Cited

U.S. PATENT DOCUMENTS

| | | | |
|---|---|---|---|
| 5,695,746 | A | 12/1997 | Garlick, Jr. et al. |
| 5,700,782 | A | 12/1997 | Cope et al. |
| 5,869,118 | A | 2/1999 | Morris et al. |
| 5,972,685 | A | 10/1999 | Beitz et al. |
| 5,993,785 | A | 11/1999 | Johansen et al. |
| 6,117,417 | A | 9/2000 | Wicks et al. |
| 6,165,494 | A | 12/2000 | Picciano |
| 6,171,611 | B1 | 1/2001 | Picciano |
| 6,348,187 | B1 | 2/2002 | Pan et al. |
| 6,387,352 | B1 | 5/2002 | Johansen et al. |
| 6,790,444 | B2 | 9/2004 | Le et al. |
| 7,029,842 | B2 | 4/2006 | Duffner et al. |
| 7,569,215 | B2 | 8/2009 | Wittrup et al. |
| 8,759,088 | B2 | 6/2014 | Steidler et al. |
| 2002/0044910 | A1 | 4/2002 | Johansen et al. |
| 2003/0152530 | A1 | 8/2003 | Johansen et al. |
| 2004/0076590 | A1 | 4/2004 | Wilkins |
| 2006/0269515 | A1 | 11/2006 | Denis-Mize et al. |
| 2007/0243303 | A1* | 10/2007 | Dan Hengst ............ A23C 9/12 426/582 |
| 2010/0080774 | A1 | 4/2010 | Steidler et al. |
| 2012/0039853 | A1 | 2/2012 | Corveleyn et al. |
| 2012/0244112 | A1 | 9/2012 | Ast et al. |
| 2014/0004080 | A1 | 1/2014 | Klatzmann et al. |
| 2014/0105863 | A1 | 4/2014 | Vanden-Broucke et al. |
| 2019/0022154 | A1 | 1/2019 | Rottiers et al. |

FOREIGN PATENT DOCUMENTS

| | | |
|---|---|---|
| EP | 0569604 A1 | 11/1993 |
| EP | 1730184 A2 | 12/2006 |
| GB | 227835 A | 4/1925 |
| WO | WO-92/14837 A1 | 9/1992 |
| WO | WO-93/17117 A1 | 9/1993 |
| WO | WO-96/32487 A1 | 10/1996 |
| WO | WO-97/14806 A2 | 4/1997 |
| WO | WO-97/38712 A1 | 10/1997 |
| WO | WO-00/23471 A2 | 4/2000 |
| WO | WO-2000/18377 A1 | 4/2000 |
| WO | WO-2000/22909 A2 | 4/2000 |
| WO | WO-01/02570 A1 | 1/2001 |
| WO | WO-2001/02576 A1 | 1/2001 |
| WO | WO-2001/062944 A2 | 8/2001 |
| WO | WO-01/94585 A1 | 12/2001 |
| WO | WO-02/090551 A2 | 11/2002 |
| WO | WO-2004/046346 A2 | 6/2004 |
| WO | WO-2004/069177 A2 | 8/2004 |
| WO | WO-2005/071088 A2 | 8/2005 |
| WO | WO-2005/086751 A2 | 9/2005 |
| WO | WO-2005/086798 A2 | 9/2005 |
| WO | WO-2008/084115 A2 | 7/2008 |
| WO | WO-2013/036914 A1 | 3/2013 |

OTHER PUBLICATIONS

Gil et al., Determination of the Core of a Minimal Bacterial Gene Set (Micro Mol Bio Rev, 2004, 68:518-537) (Year: 2004).*

Campbell et al. Developing the next generation of monoclonal antibodies for the treatment of rheumatoid arthritis (BJP, 2011, 162:1470-1484)(Year: 2011).*

NCBI, GenBank accession No. AF210073. Streptococcus gordonii lac operon, partial sequence, first deposited by Boken et al. 1999, p. 1-4 (Year: 1999).*

NCBI, GenBank accession No. M28357. Lactococcus lactis phospho-beta-galactosidase (lacG) gene, complete cds, first deposited by De Vos et al. 1989, p. 1-3 (Year: 1989).*

Payne et al., Exploitation of a chromosomally integrated lactose operon for controlled gene expression in Lactococcus lactis. FEMS Microbiology Letters 136 (1996) 19-24 (Year: 1996).*

Drouault et al., The Peptidyl-Prolyl Isomerase Motif Is Lacking in PmpA, the PrsA-Like Protein Involved in the Secretion Machinery of Lactococcus lactis. Applied and Environmental Microbiology, Aug. 2002, p. 3932-3942 (Year: 2002).*

Kok et al., "Construction of Plasmid Cloning Vectors for Lactic Streptococci Which Also Replicate in Bacillus subtilis and *Escherichia coli*," Applied and Environmental Microbiology, vol. 48, No. 4, pp. 726-731, Oct. 1984.

Goulding et al., "Distinctive Profiles of Infection and Pathology in Hamsters Infected with Clostridium difficile Strains 630 and B1," Infection and Immunity, vol. 77, No. 12, pp. 5478-5485, Dec. 2009.

Selleck et al., "Recombinant protein complex expression in *E. coli*," NIH Public Access, Current Protocol in Protein Science, Chapter: Unit 5.21, May 2008.

Madison et al., "cis Elements of the Villin Gene Control Expression in Restricted Domains of the Vertical (Crypt) and Horizontal (Duodenum, Cecum) Axes of the Intestine," The Journal of Biological Chemistry, vol. 277, No. 36, pp. 33275-33283, Sep. 6, 2002.

Keffer et al., "Transgenic mice expressing human tumour necrosis factor: a predictive genetic model of arthritis," The EMBO Journal, vol. 10, No. 13, pp. 4025-4031, 1991.

Stemmer et al., "Single-step assembly of a gene and entire plasmid from large numbers of oligodeoxyribonucleotides," Gene, vol. 164, pp. 49-53, 1995.

Tan et al., "The pST44 polycistronic expression system for producing protein complexes in *Escherichia coli*," Protein Expression and Purification, vol. 40, pp. 385-395, 2005.

O'Kane et al., Integrable α-Amylase Plasmid for Generating Random Transcriptional Fusions in Bacillus subtilis. Journal of Bacteriology, Nov. 1986, p. 973-981.

Dunn et al., A vector for promoter trapping in Bacillus cereus vector for promoter trapping in Bacillus cereus. Gene 226 (1999) 297-305.

Mota et al., Control of the Arabinose Regulon in Bacillus subtilis by AraR in Vivo: Crucial Roles of Operators, Cooperativity, and DNA Looping. J Bacterial. Jul. 2001; 183(14): 4190-4201.

Zuber et al., Use of a lacZ Fusion to Study the Role of the spoO Genes of Bacillus subtilisin Developmental Regulation. Cell. 35:275-283. Nov. 1983.

Schirrmann et al., Production systems for recombinant antibodies. Frontiers in Bioscience, vol. 13, 4576-4594, May 1, 2008.

Rosey et al., "Nucleotide and Deduced Amino Acid Sequences of the lacR, lacABCD, and lacFE Genes Encoding the Repressor, Tagatose 6-Phosphate Gene Cluster, and Sugar-Specific Phosphotransferase System Components of the Lactose Operon of *Streptococcus mutans* ", Journal of Bacteriology, Oct. 1992, p. 6159-6170, vol. 174, No. 19, American Society for Microbiology, USA.

Peschel, et al., "Inactivation of the dlt Operon in *Staphylococcus aureus* Confers Sensitivity to Defensins, Protegrins, and Other Antimicrobial Peptides", The American Society for Biochemistry and Molecular Biology, Inc., Mar. 1999, p. 8405-8410, vol. 274, No. 13, Germany.

Bruckner, Reinhold, "Gene replacement in *Staphylococcus carnosus* and *Staphylococcus xylosus*," Federation of European Microbiological Societies, Jun. 1997, vol. 151, No. 1, p. 1-8, Elsevier Science B.V., Germany.

Dobinsky, et al., "Influence of Tn917 Insertion on Transcription of the icaADBC Operon in Six Biofilm-Negative Transposon Mutants of *Staphylococcus epidermidis*", Academic Press, Jan. 2002, vol. 47, No. 1, p. 10-17, Elsevier Science B.V., Germany.

Qiao, et al., "Regulation of the nisin operons in Lactococcus lactis N8", Journal of Applied Bacteriology, Dec. 1995, vol. 80, p. 626-634, The Society for Applied Bacteriology, Finland.

Luesink, et al., "Molecular Characterization of the Lactococcus lactis ptsHI Operon and Analysis of the Regulatory Role of HPr", Journal of Bacteriology, Feb. 1999, vol. 181, No. 3, p. 764-771, American Society for Microbiology, USA.

International Search Report dated Aug. 27, 2012 for PCT/EP2012/060431.

International Preliminary Report on Patentability dated Dec. 12, 2013 for PCT/EP2012/060431.

Dominguez et al., "Non-conventional yeasts as hosts for heterologous protein production", Int. Microbial., 1998, val. 1(2), 131-142.

Ishiai et al., "Purification, gene cloning, and reconstitution of the heterotrimeric single-stranded DNA-binding protein from *Schizosaccharomyces pombe*", J. Biol. Chem., 1996, val. 271(34), 20868-20878.

(56) References Cited

OTHER PUBLICATIONS

Li et al., "Coexpression of nuclear receptor partners increases their solubility and biological activities", Proc. Natl. Acad. Sci. USA, 1997, val. 94(6), 2278-2283.
McNally et al., "Coexpression and assembly of myosin heavy chain and myosin light chain in *Escherichia coli*", Proc. Natl. Acad. Sci. USA, 1988, vol. 85(19), 7270-7273.
Smolke et al., "Coordinated, Differential Expression of Two Genes through Directed mRNA Cleavage and Stabilization by Secondary Structures", Appl. Environ. Microbial., 2000, vol. 66(12), 5399-5405.
Triode et al., "Reconstitution of the transcription factor TFIIH: assignment of functions for the three enzymatic subunits, XPB, XPD, and cdk7", Mol. Cell, 1999, vol. 3(1), 87-95.
Henricksen et al., "Recombinant Replication Protein A: Expression, Complex Formation, and Functional Characterization", J. Biol. Chem., 1994, vol. 269(15), 11121-11132.
Chancey et al., "Lactobacilli-expressed single-chain variable fragment (scFv) specific for intercellular adhesion molecule 1 (ICAM-1) blocks cell-associated HIV-1 transmission across a cervical epithelial monolayer", J. Immunol., 2006, vol. 176(9), 5627-5636.
Hultberg et al., "Lactobacillli expressing llama VHH fragments neutralise *Lactococcus* phages", BMC Biotechnol., 2007, vol. 7, 58 p. 1-7.
Kyne et al., "Asymptomatic Carriage of *Clostridium difficile* and Serum Levels of IgG Antibody against Toxin A", N Engl J Med, 2000;342(6):390-397.
Law et al., "A system to generate chromosomal mutations in *Lactococcus lactis* which allows fast analysis of targeted genes", J Bacterial, 1995, 177(24): 7011-7018.
Lowy et al., "Treatment with Monoclonal Antibodies against *Clostridium difficile* Toxins", N Engl J Med, 2010, 362(3):197-205.
Mazor et al., "Isolation of engineered, full-length antibodies from libraries expressed in *Escherichia coli*", Nat. Biotechnol., 2007, vol. 25(5), 563-565.
Perez-Martinez et al., "Protein export elements from *Lactococcus lactis*", Mol. Gen. Genet., 1992, vol. 234, 401-11.
Sibakov et al., "Secretion of TEM β-lactamase with signal sequences isolated from the chromosome of *Lactococcus lactis* subsp. *lactis*", Appl. Environ. Microbial., 1991, vol. 57(2), 341-348.
Steidler et al., "Secretion of biologically active murine interleukin-2 by *Lactococcus lactis* subsp. *lactis*", Appl. Environ. Microbial., 1995, vol. 61(4), 1627-1629.
Steidler et al., "Biological containment of genetically modified *Lactococcus lactis* for intestinal delivery of human interleukin 10", Nature Biotechnology, 2003; 21:785-789.
Sougioultzis et al., "*Clostridium difficile* Toxoid Vaccine in Recurrent *C. difficile*-Associated Diarrhea", Gastroenterology, 2005;128(3):764-770.
Wilcox, "Descriptive study of intravenous immunoglobulin for the treatment of recurrent *Clostridium difficile* diarrhoea", J Antimicrob Chemother, 2004;53(5):882-884.
Gazzaniga et al., "Oral delayed release system for colonic specific delivery", Int. J. Pharm., 1994; 108: 77-83.
Jana, S. et al., "Strategies for efficient production of heterologous proteins in *Escherichia coil*", Appl. Microbial. Biotechnol., 2005, vol. 67(3), 289-298.
Beninati et al., "Therapy of mucosal candidiasis by expression of an anti-idiotype in human commensal bacteria", Nature Biotechnology, 2000, vol. 18(10), 1060-1064.
Johnston et al., "Coexpression of proteins in bacteria using T7-based expression plasmids: expression of heteromeric cell-cycle and transcriptional regulatory complexes", Protein Expr. Purif., 2000, vol. 20(3), 435-443.
Kruger et al., "In situ delivery of passive immunity by lactobacilli producing single-chain antibodies", Nature Biotechnology, 2002, vol. 20(7), 702-706.
Leenhouts et al., "A lactococcal pWV01-based integration toolbox for bacteria", Methods in Cell Science, 1998; 20:35-50.

Leung et al., "Treatment with intravenously administered gamma globulin of chronic relapsing colitis induced by *Clostridium difficile* toxin", J Pediatr, 1991 ; 18(4 Pt 1):633-637.
Simmons et al., "Expression of full-length immunoglobulins in *Escherichia coli*: rapid and efficient production of aglycosylated antibodies", J. Immunol. Methods., 2002. val. 263(1-2), 133-147.
Smolke & Keasling, "Effect of Gene Location, mRNA Secondary Structures, and RNase Sites on Expression of Two Genes in an Engineered Operon", Biotechnol. Bioeng., 2002, val. 80(7), 762-776.
Tan, "A modular polycistronic expression system for overexpressing protein complexes in *Escherichia coli*," Protein. Expr. Purif., 2001, vol. 21 (1), 224-234.
Yuvaraj et al., "Human scFv SIgA expressed on *Lactococcus lactis* as a vector for the treatment of mucosal disease", Mol. Nutr. Food. Res., 2008, val. 52(8), 913-920.
Hooks et al., "Muromonab CD-3: a review of its pharmacology, pharmacokinetics, and clinical use in transplantation," Pharmacotherapy, 1991, val. 11 (1), 26-37.
Written Opinion of the International Searching Authority for PCT/EP2012/060431 dated Dec. 2, 2013.
International Search Report for PCT/EP2012/060431 dated Dec. 6, 2012.
Gross et al., "The Functional and Regulatory Roles of Sigma Factors in Transcription," Cold Spring Harbor Symposia on Quantitative Biology, vol. LXIII., pp. 141-155, 1998, downloaded from symposium.cshlp.org on Aug. 30, 2017.
Haugen et al., "Advances in bacterial promoter recognition and its control by factors that do not bind DNA," Nat Rev Microbiol., vol. 6, No. 7, 2008.
Office Action dated Jul. 24, 2017 is Russian Patent Application No. 2013157300 (4 pages) with an English translation (2 pages).
Lewis et al., Compartmentalization of transcription and translation in Bacillus subtilis. The EMBO Journal vol. 19 No. 4 pp. 710-718, 2000 (Year: 2000).
DeLisa et al., Folding quality control in the export of proteins by the bacterial twin-arginine translocation pathway. PNAS, 2003, 100:6115-6120.
Antonioli, L., et al., CD39 and CD73 in immunity and inflammation, Trends Mol. Med. 2013, 19(6): 355-367.
Arden, S. D., T. Zahn, S. Steegers, S. Webb, B. Bergman, R. M. O'Brien, J. C. Hutton. 1999. Molecular cloning of a pancreatic islet-specific glucose-6-phosphatase catalytic subunit-related protein. Diabetes 48: 531-542.
Argos, A possible homology between immunodeficiency virus p24 core protein and picornaviral VP2 coat protein: [prediction of HIV p24 antigenic sites, EMBO J., 8:779-785 (1989).
Batchelor et al., An in vitro mucosal model for prediction of the bioadhesion of alginate solutions to the oesophagus, Int. J. Pharm., 238: 123-32, 2002.
Bruschi, M. L., & de Freitas, O. (2005). Oral bioadhesive drug delivery systems. Drug Development and Industrial Pharmacy, 31(3), 293-310.
Demeester et al., Preexisting Insulin Autoantibodies Predict Efficacy of Otelixizumab in Preserving Residual β-Cell Function in Recent-Onset Type 1 Diabetes, Diabetes Care 2015, 38(4): 644-651.
Devos et al., Molecular cloning of human interleukin 2 cDNA and its expression in *E. coli*, Nucleic Acids Res. 1983, 11(13): 4307-23.
Dogra et al., Alternative splicing of G6PC2, the gene coding for the islet-specific glucose-6-phosphatase catalytic subunit-related protein (IGRP), results in differential expression in human thymus and spleen compared with pancreas, Diabetologia 2006; 49(5):953-7.
Drouault S, et al., Survival, Physiology, and Lysis of Lactococcus lactis in the Digestive Tract, Appl. Environ. Microbiol. 1999; 65(11): 4881-6.
Gagliani, N. et al., Coexpression of CD49b and LAG-3 identifies human and mouse T regulatory type 1 cells, Nat. Med. 2013, 19(6): 739-746.
Gasson MJ, Plasmid Complements of *Streptococcus lactis* NCDO 712 and Other Lactic Streptococci After Protoplast-Induced Curing, J. Bacteriol. 1983, 154(1):1-9.

(56) References Cited

OTHER PUBLICATIONS

Glenting et al., A Plasmid Selection System in Lactococcus lactis and Its Use for Gene Expression in L. lactis and Human Kidney Fibroblasts, Appl. Environ. Microbiol. (2002) 68:5051-5056.

Grinberg-Bleyer Y. et al., IL-2 reverses established type 1 diabetes in NOD mice by a local effect on pancreatic regulatory T cells, J. Exp. Med. 2010; 207(9):1871-1878.

Hartemann A. et al., Low-dose interleukin 2 in patients with type 1 diabetes: a phase1/2 randomised, double-blind, placebo-controlled trial, Lancet Diabetes Endocrinol. 2013; 1:295-305.

International Search Report dated Mar. 13, 2017 for PCT/IB2017/050204.

Jones A.G. and Hattersley A.T., The clinical utility of C-peptide measurement in the care of patients with diabetes, Diabetic Medicine 2013, 30: 803-817.

Little RR et al., Standardization of C-Peptide Measurements, Clin. Chem. 2008, 54: 1023-1026.

Mallone R. et al., Of Bugs and Men: antigen-Fortified Lactococcus lactis for Type 1 Diabetes Immunotherapy, Diabetes, 2014, 63 (8): 2603-2605.

Martin et al., Cloning and Characterization of the Human and Rat Islet-specific Glucose-6-phosphatase Catalytic Subunit-related Protein (IGRP) Genes, J. Biol. Chem. 2001; 276(27):25197-207.

Mayer, L. and Shao, L., Therapeutic potential of oral tolerance. Nat Rev Immunol 2004. 4: 407-419.

Mosmann, et al., "Species-Specificity of T cell stimulating activities of IL 2 and BSF-1 (IL 4): comparison of normal and recombinant, mouse and human IL 2 and BSF-1 (IL 4)," Journal of Immunology, 1987, vol. 138, No. 6, pp. 1813-1816.

Nair, "A simple practice guide for dose conversion between animals and human," 2016 Journal of Basic and Clinical Pharmacy, vol. 7, No. 2, pp. 27-31.

pp. 341-344 of Harwood and Cutting, "Molecular Biological Methods for Bacillus," John Wiley & Co. 1990.

Rapoport: "Gene Expression Using Bacillus", Current Opinion in Biotechnology, vol. 1, 1990, pp. 21-27.

Robert et al., Trimming of two major type 1 diabetes driving antigens, GAD65 and IA-2, allows for successful expression in Lactococcus lactis. Benef Microbes, 2015, 6(4):591-601.

Robert S. and Steidler L., "Recombinant Lactococcus lactis can make the difference in antigen-specific immune tolerance induction, the Type 1 Diabetes case," Microb. Cell Fact. 2014, 13 Suppl. 1: S11.

Robert, S. et al., Oral Delivery of Glutamic Acid Decarboxylase (GAD)-65 and iL10 by Lactococcus lactis Reverses Diabetes in Recent-Onset NOD Mice, Diabetes 2014, 63: 2876-2887.

Rosenzwajg M. et al., Low-dose interleukin-2 fosters a dose-dependent regulatory T cell tuned milieu in T1D patients, J Autoimmun. 2015; 58:48-58.

Sanders et al., Stress Response in Lactocossus lactis: Cloning, Expression Analysis, and Mutation of the Lactococcal Superoxide Dismutase Gene, J. Bacteriol. 1995, 177(18):5254-5260.

Schotte, et al., Secretion of biologically active murine interleukin-10 by Lactococcus lactis, Enzyme Microb. Technol. 2000, 27(10):761-765.

Sorensen et al., A Food-Grade Cloning System for Industrial Strains of Lactococcus lactis, Appl. Environ. Microbiol., 2000, 66:1253-1258.

Steidler et al., "Mucosal Delivery of Murine Interleukin-2 (IL-2) and IL-6 by Recombinant Strains of *Lactococcus lactis* Coexpressing Antigen and Cytokine," Infection and Immunity, 1998, vol. 66, No. 7, pp. 3183-3180.

Steidler et al., Treatment of Murine Colitis by Lactococcus lactis Secreting Interleukin-10, Science 2000; 289(5483): 1352-1355.

Steidler, Lothar, and Klaas Vandenbroucke. "Genetically Modified Lactococcus Lactis: Novel Tools for Drug Delivery." International Journal of Dairy Technology 59.2 (2006): 140-146.

Strobel et al., Immunological response to fed protein antigens in mice, Immunology 1983, 49:451-456.

Suarez-Pinzon, WL et al., Combination Therapy with Glucagon-Like Peptide-1 and Gastrin Restores Normoglycemia in Diabetic NOD Mice, Diabetes 2008; 57:3281-8.

Takiishi, T. et al., Reversal of autoimmune diabetes by restoration of antigen-specific tolerance using genetically modified *Lactococcus lactis* in mice, J. Clin. Inv. 2012, 122(5): 1717-1725.

Tang Q, Bluestone JA., The Foxp3+ regulatory T cell: a jack of all trades, master of regulation, Nat. Immunol. 2008; 9(3): 239-244.

Taniguchi et al., Structure and expression of a cloned cDNA for human interleukin-2, Nature 1983, 302(5906):305-10.

Van Asseldonk et al. Functional analysis of the Lactococcus lactis usp45 secretion signal in the secretion of a homologous proteinase and a heterologous alpha-amylase.(1993) Mol. Gen. Genet. 240:428-434.

van Belle, T.L. et al., Type 1 Diabetes: Etiology, Immunology, and Therapeutic Strategies, Physiol. Rev. 2011, 91(1): 79-118.

Waterfield, N. R., R. W. Le Page, P. W. Wilson, and J. M. Wells. 1995. The isolation of lactococcal promoters and their use in investigating bacterial luciferase synthesis in Lactococcus lactis. Gene 165:9-15.

Wiedmeyer et al., International Comparison of C-Peptide Measurements, Clin. Chem. 2007, 53: 784-787.

Written Opinion dated Mar. 13, 2017 for PCT/IB2017/050204.

Yu, A., et al., Selective IL-2 Responsiveness of Regulatory T Cells Through Multiple Intrinsic Mechanisms Supports the Use of Low-Dose IL-2 Therapy in Type 1 Diabetes, Diabetes 2015, 64: 2172-2183.

Zheng Y, Rudensky AY., Foxp3 in control of the regulatory T cell lineage, Nat. Immunol. 2007; 8(5): 457-462.

Tang Q et al., "Central role of a defective interleukin-2 production in triggering islet autoimmune destruction," Immunity. May 2008; 28(5): 687-697, published online May 8, 2008. doi: 10.1016/j.immuni.2008.03.016.

* cited by examiner

A

B

A

B

A

B

A

B

A

B

A

B

A

B

C

D

E

D

E

POLYCISTRONIC EXPRESSION SYSTEM FOR BACTERIA

CROSS-REFERENCE TO RELATED APPLICATIONS

This application is a divisional application of U.S. patent application Ser. No. 14/122,545 (allowed), filed Nov. 26, 2013, which is the National Stage Entry of PCT/EP2012/060431, filed Jun. 1, 2012, and claims benefit of European Application Nos. 11168495.7, filed Jun. 1, 2011 and 11173588.2, filed Jul. 12, 2011, the contents of each of which are incorporated herein by reference.

SEQUENCE LISTING

The instant application contains a sequence listing which has been submitted in ASCII format via EFS-WEB and is incorporated by reference in its entirety. Said ASCII copy, created on Feb. 7, 2018, is named 205350_0023_01_560404_SL.txt, and is 3,400 bytes in size.

FIELD OF THE INVENTION

The invention belongs to the fields of biology and medicine, more particular molecular and cellular biology, and relates to recombinant engineering and expression of products such as peptides, polypeptides or proteins by microorganisms. More specifically, the invention relates to polycistronic expression constructs or cassettes for expression of such products by microorganisms, and further to related vectors, transformed hosts, uses and applications, such as delivery, especially therapeutic delivery, of so-expressed products to subjects.

BACKGROUND OF THE INVENTION

To date, many expression systems for recombinant proteins have been developed, for various biotechnological applications. Systems for heterologous or homologous gene expression have been established in prokaryotes, yeasts and fungi and in mammalian cells.

Most recombinant proteins produced in yeasts have been expressed using *Saccharomyces cerevisiae* as the host system. Despite this, several limitations have been detected in the *S. cerevisiae* system. Examples are product yield, which is usually low, and inefficient secretion (many *S. cerevisiae* proteins are not found free in the culture medium but rather are retained in the periplasmic space or associated with the cell wall) (Dominguez et al. *Int. Microbiol.,* 1998, vol. 1(2), 131-142). Because of limitations of production in yeast, a lot of interest arose for expression of proteins in bacteria, which are easy to grow in an inexpensive broth and are frequently used to produce recombinant proteins. Among prokaryotic systems, the highest protein levels are usually obtained using recombinant expression in *Escherichia coli* (*E. coli*) (Jana & Deb. *Appl. Microbiol. Biotechnol.,* 2005, vol. 67(3), 289-298). However, in *E. coli*, the most commonly used production strategies are intracellular (in the periplasm or cytoplasm), and therefore involve expensive and often problematic downstream purification processes.

Lactic Acid Bacteria (LAB) are becoming increasingly important as hosts for recombinant expression of heterologous polypeptides in vitro (e.g., U.S. Pat. No. 5,559,007), as well as for in vivo or in situ expression and delivery of antigens and/or therapeutically relevant polypeptides (e.g., WO 97/14806). Heterologous proteins produced in these Gram-positive bacterial hosts can easily be secreted into the medium, thus facilitating their purification as well as their direct delivery to subjects.

Most expression systems can handle very well the expression of one single protein (as a result of one single gene sequence). However, in some cases it is desirable to have an expression system that is capable of expressing multiple proteins or multigenic protein complexes, for example, the in vitro expression of antibodies or protein complexes, but also in vivo or in situ expression and delivery of two or more proteins that have a synergistic effect in a particular disease or the in vivo or in situ expression and delivery of antibodies or functional (multigenic) fragments thereof. In these cases, it is desirable to have the multiple genes that are encoding the desired proteins or antibodies under the control of one promoter, because of the necessity of tight co-regulation of the multiple genes.

The two most common approaches to produce recombinant protein complexes are to perform in vitro reconstitution of individually expressed and purified subunits, or to implement in vivo reconstitution by co-expressing the subunits in an appropriate host (Selleck & Tan, "Recombinant protein complex expression in *E. coli*", *Curr. Protoc. Protein Sci.,* 2008, chapter 5:unit 5, 21). Although in vitro reconstitution has been successfully used, the process is tedious (each subunit has to be expressed and purified, and the complex has to be further purified after reconstitution) and reconstitution yields are often low. In contrast, in vivo reconstitution by co-expression offers the benefits of efficiency (only one round of expression and purification) and potentially higher yields and quality of the desired complex (refolding and assembly of the complex take place in the presence of protein folding enzymes in a cellular environment) (Selleck & Tan 2008, supra). In vivo reconstitution has been successfully performed by co-infecting insect cells with baculoviruses expressing individual protein subunits (Tirode et al. *Mol. Cell,* 1999, vol. 3(1), 87-95), and in bacteria from multiple plasmids (Johnston et al. *Protein Expr. Purif.,* 2000, vol. 20(3), 435-443; McNally et al. Proc. Natl. Acad. Sci. USA, 1988, vol. 85(19), 7270-7273) or from specialized polycistronic plasmids (Henricksen et al. *J. Biol. Chem.,* 1994, vol. 269(15), 11121-11132; Ishiai et al. J. Biol. Chem. 1996, vol. 271(34), 20868-20878; Li et al. Proc. Natl. Acad. Sci. USA, 1997, vol. 94(6), 2278-2283).

General polycistronic expression systems for producing protein complexes in *E. coli* have been described (Selleck & Tan 2008, supra; Tan. *Protein. Expr. Purif.,* 2001, vol. 21(1), 224-234; Tan et al. *Protein Expr. Purif.,* 2005, vol. 40(2), 385-395). These systems utilize the concept of a translation cassette, comprised of the coding region with requisite START and STOP codons and preceded by translational initiation signals such as the Shine-Dalgarno (SD) sequence and translational enhancers (Tan 2001, Tan et al. 2005, supra). When transcribed into mRNA, the translation cassette contains the necessary and sufficient information for the *E. coli* translational machinery to initiate and sustain translation of the mRNA into the desired polypeptide (Selleck & Tan 2008, supra).

A bi-cistronic expression vector for interleukin-18 has been described in *E. coli*, however, the intergenic region between the two genes consisted of a synthetic linker, and is clearly gene-specific as the expression of the caspase-4 was much higher than the expression of ICE. Smolke et al. previously demonstrated that it is possible to differentially control the protein levels encoded by two or more genes in an operon using synthetic intergenic region sequences (Smolke et al. *Appl. Environ. Microbiol.,* 2000, vol. 66(12), 5399-5405; Smolke & Keasling. *Biotechnol. Bioeng.*, 2002, vol. 80(7), 762-776). However, this approach relies on random combinations, and requires the introduction of synthetic sequences into the expression host.

The demand for new and improved antibody production systems has arisen in recent years. Systems for antibody expression have been established in prokaryotes, yeasts and fungi and in mammalian cells. Although single chain and single domain antibodies are easier to produce from bacteria, full-size antibodies generally have higher binding affinities and less risk for formation of neutralizing antibody when injected.

Full-size antibodies can be produced from bacteria (Mazor et al. *Nat. Biotechnol.*, 2007, vol. 25(5), 563-565; Simmons et al. *J. Immunol. Methods*, 2002, vol. 263(1-2), 133-147). Most reports on recombinant prokaryotic expression describe production of antibody fragments, albeit almost exclusively from *E. coli*. Although many engineered LAB are capable of correct disulphide bonding, the literature contains only a limited number of examples of antibody-like molecules produced from LAB (Kruger et al. *Nature Biotechnology*, 2002, vol. 20(7), 702-706; Beninati et al. *Nature Biotechnology*, 2000, vol. 18(10), 1060-1064; Chancey et al. *J. Immunol.*, 2006, vol. 176(9), 5627-5636; Hultberg et al. *BMC Biotechnol.*, 2007, vol. 7, 58; Yuvaraj et al. *Mol. Nutr. Food. Res.*, 2008, vol. 52(8), 913-920). These reports only describe single chain antibody fragments expressed in *Lactobacillus* species, *Lactococcus lactis* and *Streptococcus gordonii*, and not multigenic, double chain antibody fragments or full-sized antibodies.

Polycistronic expression systems could be crucial in obtaining efficient prokaryotic synthesis and expression of complex proteins such as antibodies. Since the FDA approval in 1986 of Muromonab-CD3, still one of the most potent immunosuppressive drugs available for the management of transplant rejection (Hooks et al. Pharmacotherapy, 1991, vol. 11(1), 26-37), full-size antibodies and antibody fragments have become increasingly important and versatile tools in medicine.

While the current state of the art reveals several examples of polycistronic expression systems in bacterial cells, these are quite limited, highlighting the need for a more efficient system for introducing and expressing multiple genes. Accordingly, there exists a need to provide further sequences which can be favourably used for expression of proteins, preferably heterologous protein expression and even more preferably multiple heterologous protein expression.

In addition to the above, the endeavour to produce higher amounts of recombinant protein, both for direct protein delivery by recombinant microorganisms as well as for bulk protein production and down stream purification, represents a great technological strive. An existing approach to increase production of heterologous proteins is the use of selected strong promoters (see for instance WO 2008/084115). In this approach, proteomic analysis is performed to identify the most abundant endogenous proteins expressed by a microorganism. By use of the genome sequence, the respective genes and promoters can be identified and isolated. These strong promoters (e.g. the *Lactococcus lactis* hllA gene promoter, PhllA) can be positioned in front of a heterologous gene and in this way, high expression can be achieved. However, a level of expression which impairs host physiology may impose a growth burden on the host and results in counter-selection. This intrinsically limits the highest possible expression of any given heterologous protein in an expression host to a certain specific level. This is an especially cumbersome obstacle in the development of chromosomally located expression units.

The issue of counter-selection is traditionally addressed by the provision of selection markers. Indeed, positive or negative selection, e.g. by providing antibiotic resistance genes, can prevent loss of the introduced heterologous gene. Alternatively, or in addition to the use of selection markers, inducible gene expression systems may be employed, which allow for uncoupling propagation of the host and expression of the heterologous protein, thereby preventing possible counter-selection during the propagation phase when the heterologous gene is not expressed. In this context, EP0569604 describes an inducible expression system in *Streptococcus thermophilus* in which a heterologous gene is obligatory positioned 5' to the LacZ gene. In this way, expression of the heterologous gene is not only inducible but in addition maintenance of the heterologous gene is also selected for by growing the bacteria in their natural habitat, milk, with lactose as carbon source, which requires the expression of the LacZ gene.

It is clear that the systems for heterologous gene expression described above are limited in application. For instance, the use of selection markers, such as antibiotic resistance genes, is not readily tolerated for applications in food production or in pharmaceutical applications. Further, limitation to growing in the natural habitat or to using the carbon source from the natural habitat for growth significantly reduces the versatility of any system for heterologous gene expression. Also, the use of inducible systems is inherently dependent on the growth conditions of the host, such that defined culture media, to which an inducer is to be added, are needed to ensure expression of the heterologous protein.

Accordingly, there also exists a need in the art to increase heterologous protein expression; and sequences, cloning systems and strategies are needed which can achieve high expression levels in order to obtain sufficient amounts of expressed heterologous proteins in industrial and/or therapeutic settings, while at the same time being versatile and widely applicable under a variety of different conditions. In these settings it would also be particularly useful to obtain expression of multiple proteins, each having its own biological activity and therapeutic effect.

SUMMARY OF THE INVENTION

The aspects and embodiments of the present invention address at least some, e.g., one or more, of the above discussed needs of the art.

The inventors have surprisingly found that gram-positive bacteria can efficiently express exogenous or heterologous genes from polycistronic expression units also comprising endogenous gene(s) of these bacteria. Thus, gram-positive bacteria can efficiently express exogenous or heterologous genes from polycistronic expression units when such genes are transcriptionally or translationally coupled to endogenous gene(s) of these bacteria. Unexpectedly, the inventors have found that transcriptional and/or translational coupling of endogenous genes and exogenous genes in polycistronic expression units results in high expression levels of the exogenous genes in gram-positive bacteria. In particular, expression levels of exogenous genes transcriptionally and/or translationally coupled to gram-positive bacterial endogenous genes were found to be at least comparable to and advantageously higher than expression levels of exogenous genes which are not transcriptionally or translationally coupled to gram-positive bacterial endogenous genes.

Accordingly, in an aspect the invention relates to a gram-positive bacterium comprising a polycistronic expression unit, said polycistronic expression unit comprising one or more endogenous genes and one or more exogenous genes. The polycistronic expression unit can thus also be denoted as comprising an endogenous gene (for example but without limitation one endogenous gene) and one or more exogenous genes. Preferably, the polycistronic expression unit consecutively comprises one or more endogenous genes and one or more exogenous genes. Such polycistronic expression unit can thus also be denoted as consecutively comprising an endogenous gene (for example but without limitation one endogenous gene) and one or more exogenous genes. The polycistronic expression unit is configured to effect transcription of the one or more endogenous genes and the one or more exogenous genes in a polycistronic mRNA. Hence, the present gram-positive bacterium may otherwise be denoted as comprising one or more endogenous genes to which one or more exogenous genes are transcriptionally or translationally coupled. Also provided is thus a gram-positive bacterium comprising one or more endogenous genes to which one or more exogenous genes are transcriptionally and/or translationally coupled.

Another aspect provides a recombinant nucleic acid comprising a polycistronic expression unit, said polycistronic expression unit comprising a gene endogenous to a gram-positive bacterium and one or more genes exogenous to the gram-positive bacterium. Preferably, the polycistronic expression unit consecutively comprises one or more endogenous genes and one or more exogenous genes. Hence, also provided is a recombinant nucleic acid comprising a polycistronic expression unit comprising one or more gene endogenous to a gram-positive bacterium to which one or more genes exogenous to the gram-positive bacterium are transcriptionally and/or translationally coupled.

Preferably, as intended throughout this specification said one or more exogenous genes may be transcriptionally or translationally coupled to the 3' end of said one or more endogenous genes. The inventors have surprisingly found that such configuration is beneficial in respect of heterologous protein expression levels, maintenance and/or genomic stability of the polycistronic expression unit. It has moreover been found that further downstream genomic arrangement is of lesser or no importance.

The transcription of the transcriptionally or translationally coupled one or more endogenous genes and one or more exogenous genes may be suitably regulated or controlled by a promoter capable of achieving transcription in the gram-positive bacterium, and preferably may be regulated or controlled by an endogenous promoter of said gram-positive bacterium. Hence, also provided is a gram-positive bacterium comprising one or more endogenous genes located in its native chromosomal locus, to which one or more exogenous genes are transcriptionally or translationally coupled. Preferably, transcription of these transcriptionally or translationally coupled one or more endogenous genes and one or more exogenous genes are thus controlled or regulated by the native promoter of said one or more endogenous genes. Suitably, the transcriptional or translational coupling may be achieved by chromosomally integrating the one or more exogenous genes to said locus, such as for example by chromosomally integrating the one or more exogenous genes 3' of said one or more endogenous genes in said locus.

Accordingly, in an aspect, the invention relates to a recombinant nucleic acid or a gram-positive bacterium comprising a polycistronic expression unit, said polycistronic expression unit consecutively comprising an endogenous gene and one or more exogenous genes transcriptionally coupled to the 3' end of said one or more endogenous gene, preferably wherein said one or more exogenous gene(s) is (are) the most 3' gene(s) of the polycistronic expression unit.

The inventors have surprisingly found that chromosomal integration of an exogenous or heterologous gene (or multiple heterologous genes) transcriptionally coupled 3' to a native gene, which in itself may be a polycistronic gene, such as for instance an operon, yields a stable expression unit, in which counter selection against the (one or more) exogenous gene is absent or minimal, contrary to expectations.

The inventors have unexpectedly found that the herein described advantages are increasingly manifested when the expression of the polycistronic expression unit is effected under certain conditions, in particular by certain types of promoters. The inventors have surprisingly found that polycistronic expression systems as described herein, in which counter-selection against the heterologous protein(s) is not addressed by conventional measures, such as the use of selection markers, or by the use of inducible systems, may nevertheless be stably maintained and expressed at high levels, thereby being broadly applicable under a variety of different conditions, absent the need of selection agents or inducers. The polycistronic expression modules as described herein thus allow the use of non-selectable endogenous and/or exogenous genes.

In an aspect, the invention relates to a recombinant nucleic acid or a gram-positive bacterium comprising a polycistronic expression unit, said polycistronic expression unit consecutively comprising an endogenous gene and one or more exogenous genes transcriptionally coupled to the 3' end of said endogenous gene, wherein expression of said polycistronic expression unit is effected by a constitutive promoter.

In another aspect, the invention relates to a recombinant nucleic acid or a gram-positive bacterium comprising a polycistronic expression unit, said polycistronic expression unit consecutively comprising an endogenous gene and one or more exogenous genes transcriptionally coupled to the 3' end of said endogenous gene, wherein expression of said polycistronic expression unit is effected by a central metabolism gene promoter.

In another aspect, the invention relates to a recombinant nucleic acid or a gram-positive bacterium comprising a polycistronic expression unit, said polycistronic expression unit consecutively comprising an endogenous gene and one or more exogenous genes transcriptionally coupled to the 3' end of said endogenous gene, wherein expression of said polycistronic expression unit is effected by a housekeeping gene promoter.

In another aspect, the invention relates to a recombinant nucleic acid or a gram-positive bacterium comprising a polycistronic expression unit, said polycistronic expression unit consecutively comprising an endogenous gene and one or more exogenous genes transcriptionally coupled to the 3' end of said endogenous gene, wherein expression of said polycistronic expression unit is effected by an essential gene promoter.

In another aspect, the invention relates to a recombinant nucleic acid or a gram-positive bacterium comprising a polycistronic expression unit, said polycistronic expression unit consecutively comprising an endogenous gene and one or more exogenous genes transcriptionally coupled to the 3' end of said endogenous gene, wherein expression of said polycistronic expression unit is not effected by an inducible gene promoter.

In another aspect, the invention relates to a recombinant nucleic acid or a gram-positive bacterium comprising a polycistronic expression unit, said polycistronic expression unit consecutively comprising an endogenous gene and one or more exogenous genes transcriptionally coupled to the 3' end of said endogenous gene, wherein expression of said polycistronic expression unit is effected by a ribosomal gene promoter.

In another aspect, the invention relates to a recombinant nucleic acid or a gram-positive bacterium comprising a polycistronic expression unit, said polycistronic expression unit consecutively comprising an endogenous gene and one or more exogenous genes transcriptionally coupled to the 3' end of said endogenous gene, wherein expression of said polycistronic expression unit is effected by a glycolysis gene promoter.

As also indicated above, in a preferred embodiment, the promoters as described above are endogenous gene promoters. As is also detailed further below, preferably, the promoters as used herein are strong promoters. Preferably but without limitation, said endogenous promoter may be selected from the group consisting of the promoters of eno, usp45, gapB, pyk, rpmB, and rplS. Very preferably, the transcription of the translationally coupled endogenous gene and one or more exogenous gene may be regulated or controlled by the native promoter of (one of) said endogenous gene.

It is to be understood that the characteristics of the promoters as described herein may be combined according to the invention. Accordingly, in embodiments, the invention relates to a recombinant nucleic acid or a gram-positive bacterium comprising a polycistronic expression unit, said polycistronic expression unit consecutively comprising an endogenous gene and one or more exogenous genes transcriptionally coupled to the 3' end of said endogenous gene, wherein expression of said polycistronic expression unit is effected by for instance a (endogenous) constitutive housekeeping gene promoter, a (endogenous) constitutive central metabolism gene promoter, a (endogenous) constitutive essential gene promoter, a (endogenous) constitutive ribosomal gene promoter, a (endogenous) constitutive glycolysis gene promoter, a (endogenous) central metabolism housekeeping gene promoter, a (endogenous) essential central metabolism gene promoter, a (endogenous) essential central metabolism housekeeping gene promoter, a (endogenous) essential housekeeping gene promoter, a (endogenous) constitutive central metabolism housekeeping gene promoter, a (endogenous) constitutive essential central metabolism housekeeping gene promoter, a (endogenous) essential ribosomal gene promoter, a (endogenous) essential glycolysis gene promoter, a (endogenous) constitutive essential ribosomal gene promoter, a (endogenous) constitutive essential glycolysis gene promoter.

Preferably as intended throughout this specification said one or more exogenous genes may be transcriptionally or translationally coupled to the 3' end of said one or more endogenous genes whereby the one or more endogenous genes are present at their native position on the bacterial chromosome. In this configuration, the sequence at the 5' end of the one or more endogenous genes (minimally including the endogenous genes promoter) is identical to that of the wild type strain and the region subsequent to the 3' end of the one or more exogenous genes are identical to the sequence of the region 3' of the one or more endogenous genes as in the wild type strain.

Many applications of exogenous protein expression such as for instance for therapeutic protein delivery by recombinant microorganisms can benefit from the expression of said therapeutic protein in specific selected host microorganisms. These microorganisms could be selected based on their colonizing capacity, as e.g. selected strains originating from the human or animal microbiota. Microorganisms could also be selected on their capacity to potentiate the activity of any specific delivered therapeutic protein e.g. as a consequence of the interaction of their cell wall, cell surface or intracellular content with the host immune system e.g. through interaction with toll like receptors, Ig family members, complement, cytokines and other. Specific microorganisms could be selected for their robustness to persist in or on specific harsh delivery sites, such as intratumoural, skin, sites with high bile content, sites with low pH and other. The gram-positive bacterium as recited throughout this specification may be preferably a lactic acid bacterium (LAB), more preferably a *Lactococcus* sp., even more preferably *Lactococcus lactis* or a subspecies or strain thereof. Alternatively, said LAB may be preferably an *Enterococcus* sp., more preferably *Enterococcus fecium* or *Enterococcus faecalis* or a subspecies or strain thereof.

To avoid lateral gene transfer to endogenous microflora, expression from a chromosomally embedded expression unit is highly favourable for use of recombinant microflora as delivery tools for therapeutic proteins in medicine. Also, chromosomally located expression units may prove to be much more stably inherited over generations, so that chromosomally located expression units may be the desirable structure for production strains used in bulk protein production. In the current state of the art, chromosomal insertion is performed by use of knock-in (KI) type vectors which are conditionally non-replicative and which contain the heterologous gene in-between flanking regions that allow homologous recombination. In a conventional approach (see for instance WO 2008/084115), the KI plasmid is constructed in the homologous host (KI plasmid for *L. lactis* is built in *L. lactis*). This is especially the case for heterologous expression that requires protein secretion, as many secretion signals are not compatible for use in other hosts. The use of strong promoters in expression constructs that are intended to be placed on the bacterial chromosome is hampered by expression of the heterologous gene from the KI plasmid intermediates. The heterologous gene is immediately preceded by a strong promoter, making that the expression from the KI plasmid, although not intended and not required, intrinsically limits the use of the strongest promoters. In many cases, the KI plasmid has a copy number that is a multiplicity of the chromosome number in the host, making that upon integration, expression will be several fold lower. Therefore, chromosomal expression units will be intrinsically weaker than what would be the highest achievable. This problem is circumvented by the invention described here. In this approach, the heterologous genes will be positioned downstream and transcriptionally and/or translationally coupled to a (strongly expressed) endogenous gene on the bacterial chromosome. This strategy does not require the endogenous (strong) promoter to be present on the KI plasmid. Rather, upstream of the heterologous gene, the promoterless 3' end of the (strongly expressed) endogenous gene is positioned. This type of KI plasmid is silent and will not limit the use of strong promoters.

The transcriptional or translational coupling of one or more exogenous genes with one or more other genes as described herein may be achieved by means of an intergenic region active (i.e., functional, effective) in a gram-positive bacterium, preferably by means of an endogenous intergenic region of a gram-positive bacterium. Accordingly, a further aspect provides a recombinant nucleic acid comprising an intergenic region active in a gram-positive bacterium, preferably an endogenous intergenic region of a gram-positive bacterium, operably linked to a gene exogenous to said gram-positive bacterium. The operable linkage ensures that a transcript of the intergenic region, present on a mRNA together with a transcript of the exogenous gene, is able to provide a site for initiation of translation of the exogenous gene, in the gram-positive bacterium. Preferably, the intergenic region may be provided 5' of the exogenous gene. The nucleic acid may comprise two or more exogenous genes in polycistronic arrangement, each exogenous gene preceded by an intergenic region. The intergenic regions may be the same or different. For example, where the intergenic regions are different, these may correspond to intergenic regions derived from different genes of the same or different species, or from the same gene of different species. These nucleic acids may be useful in constructing polycistronic expression units comprising the one or more exogenous genes, whereby one or more other gene is transcriptionally or translationally coupled with the one or more exogenous genes via the intergenic region. For example, these nucleic acids may be useful in constructing polycistronic expression units as taught herein, whereby one or more endogenous genes is transcriptionally or translationally coupled with the one or more exogenous genes via the intergenic region. Preferably the first cistron of the polycistronic expression unit will be a strongly expressed endogenous gene.

The present recombinant nucleic acids may be comprised on a replicon. An aspect thus also relates to a replicon or vector comprising the nucleic acid as taught herein. For example, the vector may be a prokaryotic expression vector, preferably a prokaryotic polycistronic expression vector. The development of such plasmid expression systems may however be tedious because the combination of certain replicons and strong promoters may be unstable. Also it may be impossible to transform selected microorganisms with recombinant plasmids and stably maintain the latter in the microorganism because of the presence of natural plasmids, especially not if no antibiotic selection markers may be included in the expression plasmid, as would be the case in an application for therapeutic protein delivery. This issue can be circumvented by positioning the heterologous genes downstream and transcriptionally or translationally coupled to a (strongly expressed) endogenous gene on the bacterial chromosome. As this strategy does not require a plasmid borne expression system, it can be used as a general approach to be applied for the genetic engineering of any type of selected microflora. The only strain specific information required can be rapidly established through state of the art technology. High throughput sequencing combined with proteomic analysis of the abundantly expressed proteins will rapidly yield the nucleotide sequence of the regions encoding the abundantly present proteins. Accordingly, most preferably, the vector as described herein may be configured to effect homologous recombination in the gram-positive bacterium, such as to generate a chromosomal integration of the exogenous gene(s).

Further provided is the use of the recombinant nucleic acid or vector as described herein for polycistronic expression of the one or more exogenous genes or for polycistronic expression of the one or more endogenous genes and one or more exogenous genes in the gram-positive bacterium. As well disclosed is the gram-positive bacterium comprising (for example, transformed with) the recombinant nucleic acid or vector as taught herein, whereby the gram-positive bacterium is capable of polycistronic expression of the one or more exogenous genes or of polycistronic expression of the one or more endogenous genes and one or more exogenous genes. Further provided is a method for effecting polycistronic expression of the one or more exogenous genes or for effecting polycistronic expression of the one or more endogenous genes and one or more exogenous genes in a gram-positive bacterium, comprising the step of introducing the recombinant nucleic acid or vector as taught herein to said gram-positive bacterium. As well provided is a method for generating a gram-positive bacterium capable of polycistronic expression of the one or more exogenous genes or capable of polycistronic expression of the one or more endogenous genes and one or more exogenous genes, comprising the step of introducing the recombinant nucleic acid or vector as taught herein to said gram-positive bacterium.

The invention allows to express, preferably strongly (highly) express, a single exogenous gene or a plurality of (e.g., two, three or more) distinct exogenous genes in a gram-positive bacterium. Said exogenous gene or genes may encode expression product or products such as advantageously protein(s), polypeptide(s) and/or peptide(s). By means of example and not limitation, such protein(s), polypeptide(s) and/or peptide(s) may encompass antigens (for example, for inducing immunity or immunotolerance), allergens, non-vaccinogenic therapeutic polypeptides (cytokines, growth factors, wound healing factors, . . . ), antibodies or functional fragments thereof (e.g., Fab fragments), fusion proteins, multimeric proteins, etc and any combination thereof.

The polycistronic organisation may render expression units as taught herein particularly suitable for the expression of proteins comprising two or more polypeptide chains (e.g., multimeric proteins, protein complexes). Accordingly, two or more exogenous genes as intended in this specification may preferably encode distinct monomers or subunits of a multimeric protein, whereby the genes are co-transcribed into a polycistronic mRNA and the individual monomers or subunits are translated from this mRNA. This can allow for tightly regulated co-expression of the exogenous genes, such as to achieve balanced and optimal assembly of the individual monomers or subunits into the multimeric protein.

A particularly advantageous illustration of this principle is the expression of antibodies or functional fragments thereof. Hence, the two or more exogenous genes as taught herein may preferably encode separate chains of an antibody or of a functional fragment thereof. For example, one exogenous gene may encode the light chain ($V_L$) of an antibody or of a functional fragment thereof, and another exogenous gene may encode the heavy chain ($V_H$) of the antibody or of a functional fragment thereof. Preferably, the functional fragment of the antibody may be Fab. In specific but non-limiting embodiments, said Fab may be binding to and/or inhibiting the biological effect of cytokines, receptors of cytokines, chemokines or immune/inflammatory activating molecules. In a preferred embodiment the Fab may be binding to and/or inhibiting the biological effect of TNFα, such as without limitation said Fab may be cA2 anti-TNF or CDP870 anti-TNF.

The exogenous genes encoding the individual chains of the antibody or of the fragment thereof are thus transcriptionally or translationally coupled for polycistronic expression in the gram-positive bacterium. Preferably, the exogenous gene encoding $V_L$ or functional fragment thereof may be transcriptionally or translationally coupled to the 3' end of the exogenous gene encoding $V_H$ or functional fragment thereof. This gene organisation yields particularly effective expression and assembly of the antibody or functional fragment thereof.

The polycistronic organisation may also render expression units as taught herein particularly suitable for the co-expression of products such as proteins that cooperate to achieve a synergistic effect, for example a synergistic therapeutic or prophylactic effect, for example when delivered in situ by the bacterium.

Another aspect provides a gram-positive bacterium as taught herein, wherein the one or more exogenous genes encodes a product or products such as protein(s), polypeptide(s) or peptide(s) having a therapeutic or preventive effect in a subject. Such bacterium is particularly provided for use as a medicament, more particularly for use in administration or delivery of said product or products to the subject, even more particularly for use in the treatment of a disease that can benefit from the administration or delivery of said product or products. Also provided is thus a pharmaceutical composition comprising such gram-positive bacterium.

As well provided is a method for delivering a product or products such as protein(s), polypeptide(s) or peptide(s) to a subject comprising administering the gram-positive bacterium as taught herein to the subject, wherein the one or more exogenous genes encodes said product or products. Preferably said product or products may have a therapeutic or preventive effect in the subject.

Advantageously for in situ delivery of the present gram-positive bacterium to subjects, the bacterium more closely retains its endogenous character by not introducing or introducing less exogenous or even pathogenic sequences besides the sequences for the exogenous expression products. Thereby, the regulatory GRAS or "Generally Recognized As Safe" status is maintained as much as possible, thus facilitating the process of acquiring clinical approval or market authorisation for the use of the engineered strains in humans or animals.

Further aspects and embodiments according to the invention are presented hereafter in items (i) to (xxii).

(i) A gram-positive bacterium comprising a polycistronic expression unit, said polycistronic expression unit consecutively comprising an endogenous gene and one or more exogenous genes transcriptionally coupled to the 3' end of said one or more endogenous gene.

(ii) A recombinant nucleic acid comprising a polycistronic expression unit, said polycistronic expression unit consecutively comprising a gene endogenous to a gram-positive bacterium and one or more genes exogenous to the gram-positive bacterium transcriptionally coupled to the 3' end of said one or more endogenous gene.

(iii) The gram-positive bacterium according to (i) or the recombinant nucleic acid according to (ii), wherein said one or more exogenous genes encodes a protein, polypeptide and/or peptide having a therapeutic or preventive effect in a subject, or an antigen for inducing immunity or immunotolerance, a non-vaccinogenic therapeutically active polypeptide, an antibody or a functional fragment thereof such as Fab, a fusion protein or a multimeric protein.

(iv) The gram-positive bacterium according to (i) or the recombinant nucleic acid according to (ii), wherein the one or more exogenous genes encodes a product, such as a protein, polypeptide or peptide, which product has a therapeutic or preventive effect in a subject, for use as a medicament, preferably for use in administration or delivery of said product to the subject.

(v) The gram-positive bacterium according to (i), (iii) or (iv) or the recombinant nucleic acid according to (ii) to (iv), wherein said one or more exogenous gene is the most 3' gene of the polycistronic expression unit.

(vi) The gram-positive bacterium according to any of (i), (iii), (iv) or (v) or the recombinant nucleic acid according to any of (ii) to (v), wherein said endogenous gene and said one or more exogenous genes are transcriptionally controlled by a promoter endogenous to the gram-positive bacterium.

(vii) The gram-positive bacterium or the recombinant nucleic acid according to (vi), wherein said promoter is an essential gene promoter, a constitutive promoter, a central metabolism gene promoter, and/or a housekeeping gene promoter.

(viii) The gram-positive bacterium or the recombinant nucleic acid according to (vi), wherein said promoter is a ribosomal gene promoter.

(ix) The gram-positive bacterium or the recombinant nucleic acid according to (vi), wherein said promoter is a glycolysis gene promoter.

(x) The gram-positive bacterium or the recombinant nucleic acid according to (vi), wherein said promoter is selected from the group consisting of the promoter of eno, usp45, gap, pyk, rpmB and rplS of said gram-positive bacterium.

(xi) The gram-positive bacterium according to any one of (i) or (ii) to (x), wherein the endogenous gene is located in its native chromosomal locus in the gram-positive bacterium.

(xii) The gram-positive bacterium according to (xi), wherein the endogenous gene is transcriptionally coupled to the one or more exogenous genes by chromosomally integrating the one or more exogenous genes to said locus, preferably by chromosomally integrating the one or more exogenous genes 3' of the endogenous gene in said locus.

(xiii) The gram-positive bacterium according to any one of (i) or (iii) to (xii) or the recombinant nucleic acid according to any of (ii) to (x), wherein the endogenous gene and the one or more exogenous genes are transcriptionally coupled by intergenic region or regions active in the gram-positive bacterium, preferably wherein the intergenic region or regions is endogenous to said gram-positive bacterium.

(xiv) The gram-positive bacterium or the recombinant nucleic acid according to (xiii), wherein said intergenic region is selected from the group consisting of intergenic regions preceding rplW, rplP, rpmD, rplB, rpsG, rpsE, rplN, rplM, rplE, and rplF.

(xv) A recombinant nucleic acid comprising an intergenic region active in a gram-positive bacterium operably linked to a gene exogenous to said gram-positive bacterium, preferably wherein the intergenic region is an endogenous intergenic region of a gram-positive bacterium.

(xvi) The recombinant nucleic acid according to (xiv), wherein said intergenic region is selected from the group consisting of intergenic regions preceding rplW, rplP, rpmD, rplB, rpsG, rpsE, rplN, rplM, rplE, and rplF.

(xvii) The gram-positive bacterium according to any one of (i) or (iii) to (xiv), or the recombinant nucleic acid according to any one of (ii) to (x) or (xiii) to (xvi), wherein one exogenous gene encodes the light chain ($V_L$) of an antibody or of a functional fragment thereof, and another exogenous gene encodes the heavy chain ($V_H$) of the antibody or of a functional fragment thereof, more preferably wherein the functional fragment is Fab.

(xviii) The gram-positive bacterium or recombinant nucleic acid according to (xvii), wherein the exogenous gene encoding $V_L$ or functional fragment thereof is transcriptionally coupled to the 3' end of the exogenous gene encoding $V_H$ or functional fragment thereof.

(xix) The gram-positive bacterium according to any one of (i), (iii) to (xiv), (xvii) or (xviii), or the recombinant nucleic acid according to any one of (ii) to (x), or (xiii) to (xviii), wherein the gram-positive bacterium is a lactic acid bacterium, preferably *Lactococcus, Lactobacillus*, or *Enterococcus*, more preferably *Lactococcus lactis* or *Enterococcus faecium*, or where the gram-positive bacterium is a *Bifidobacterium*.

(xx) A pharmaceutical composition comprising the gram-positive bacterium according to any one of (i), (iii) to (xiv), or (xvii) to (xix).

(xxi) The pharmaceutical composition according to (xx), wherein said one or more exogenous genes encodes a product, such as a protein, polypeptide or peptide, which product has a therapeutic or preventive effect in a subject.

(xxii) A vector comprising the recombinant nucleic acid according to any one of (ii) to (x), or (xiii) to (xix).

The above and further aspects and preferred embodiments of the invention are described in the following sections and in the appended claims. The subject matter of appended claims is hereby specifically incorporated in this specification.

Figure 9:
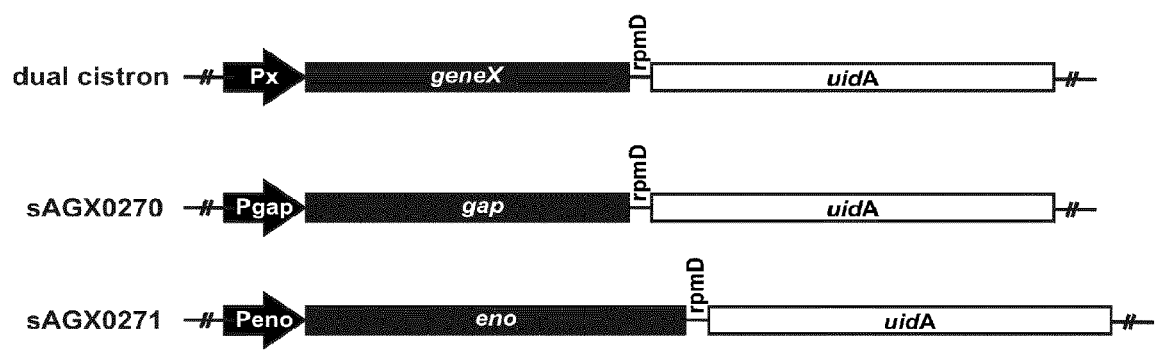
FIG. 9: Representation of polycistronic (bicistronic, dual cistron) constructs according to an embodiment of the invention whereby gene X represents an endogenous gene. Expression constructs are intended for the expression of β-glucuronidase from the *E. coli* uidA gene, serving here as an exemplary exogenous gene. Gap and eno are representative "fist" endogenous genes.

and in a host comprising a polycistronic (bicistronic) construct according to an embodiment of the invention (endogenous gene X>>rpmD>>uidA), organized as in FIG. 9. The endogenous genes X are, in this example, gapB and eno. In this example, the rpmD intergenic region provides transcriptional coupling of the endogenous and the exogenous gene. The exogenous E. coli uidA gene encodes β-glucuronidase. All expression constructs are embedded in the bacterial chromosome. The monocistronic construct is present in the thyA locus, bicistronic constructs are embedded at the native position of geneX. The data show that all bicistronic constructs have 3-galactosidase activity superior to the monocistronic PhllA>>uidA construct.

Figure 11:
Figure 11:
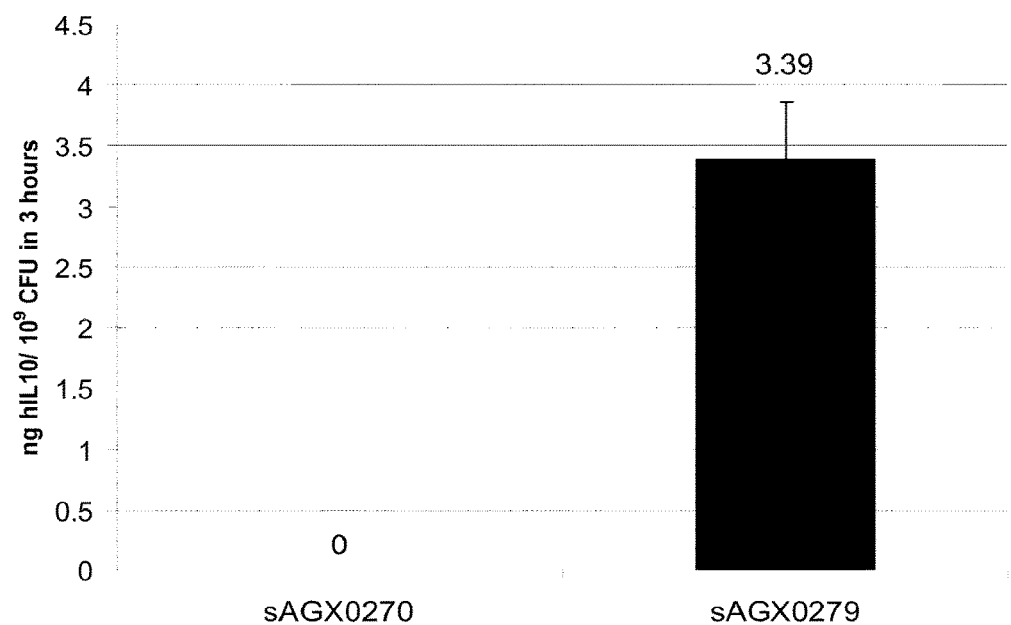

FIG. 11: Quantification of human interleukin-10 (hIL-10) secretion by *Enterococcus faecium* in a reference host (sAGX0270) and a host according to an embodiment of the invention (sAGX0279). (A) Schematic overview of hIL-10 expression modules. Bicistronic expression construct in sAGX0279 consists of a transcriptional coupling of the endogenous gap with SS::hIL10, through the rpmD intergenic region. (B) Levels of hIL-10 detected in the supernatants of the various strains.

Figure 12:
Figure 12:
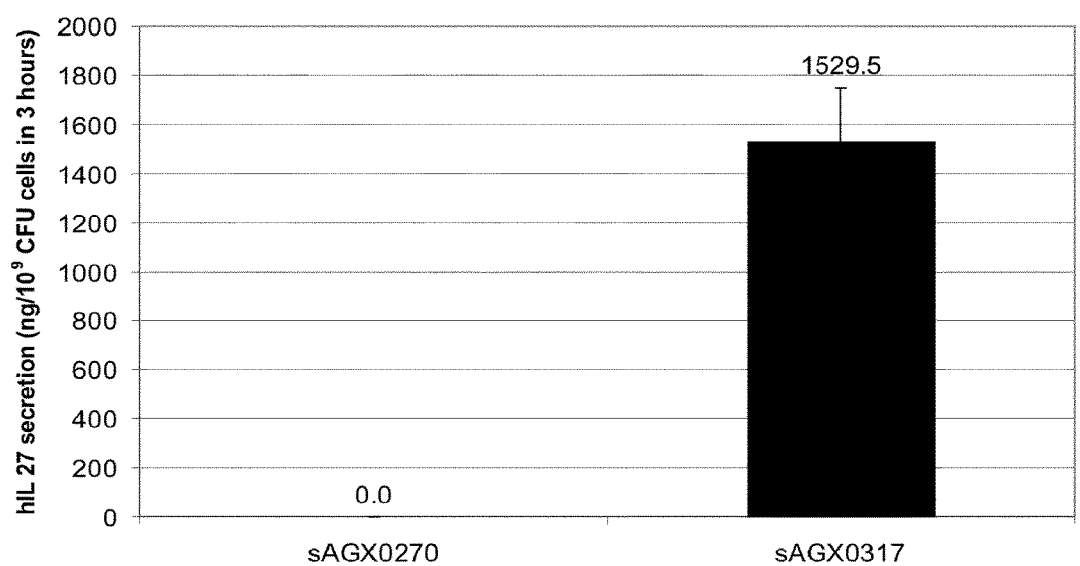

FIG. 12: Quantification of human interleukin-27 (hIL-27) secretion by *Enterococcus faecium* in a reference host (sAGX0270) and a host according to an embodiment of the invention (sAGX0317). (A) Schematic overview of hIL-27 expression modules. Bicistronic expression construct in sAGX0317 consists of a transcriptional coupling of the endogenous gap with SS::hIL27, through the rpmD intergenic region. (B) Levels of hIL-27 detected in the supernatants of the various strains.

Figure 13:
Figure 13:
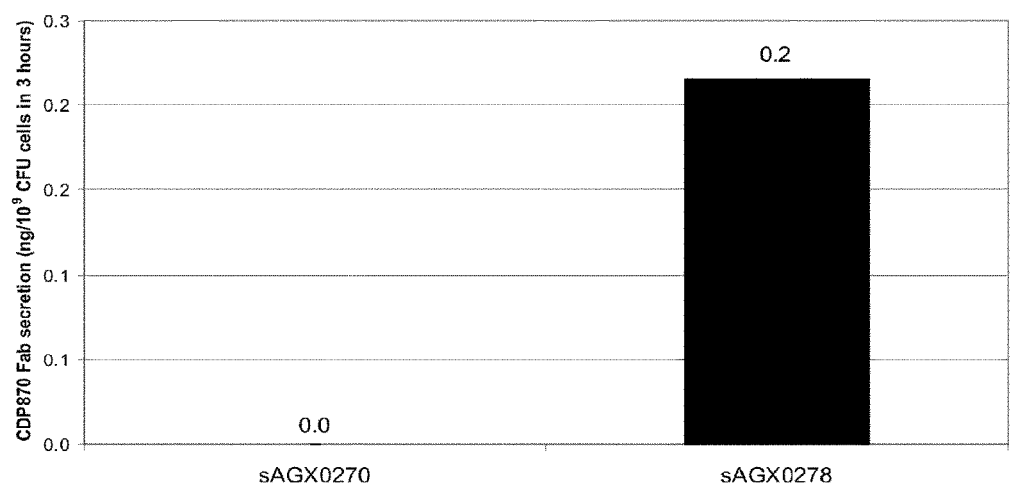

FIG. 13: CDP870 anti-TNF Fab expression in *Enterococcus faecium*. (A) CDP870 light and heavy chain fusions to usp45 secretion leader encoding sequences (SS::CDP870 VHCH1 and SS::CDP870 VLCL) were inserted as a second and third cistron downstream from gap (sAGX0278). To avoid genetic instability, light and heavy chain genes were coupled through the intergenic region preceding rpmD from *Lactococcus lactis* (LL), whereas rpmD from *Enterococcus faecium* (EF) was used to couple gap and heavy chain genes. (B) Quantification of anti-human TNF activity in crude culture supernatants. Both heavy chain and light chains were highly expressed by the dual cistron constructs, leading to high levels of functional CDP870 anti-TN F Fab.

Figure 14:
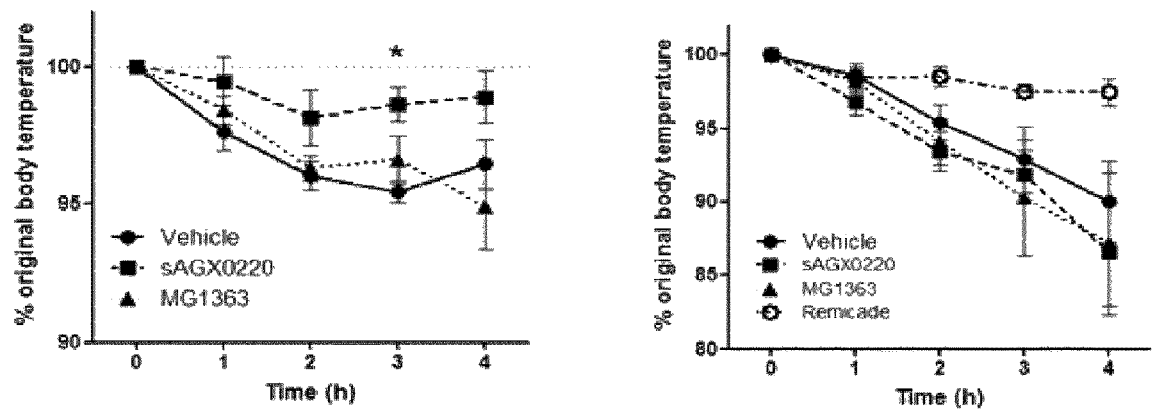
Figure 14:
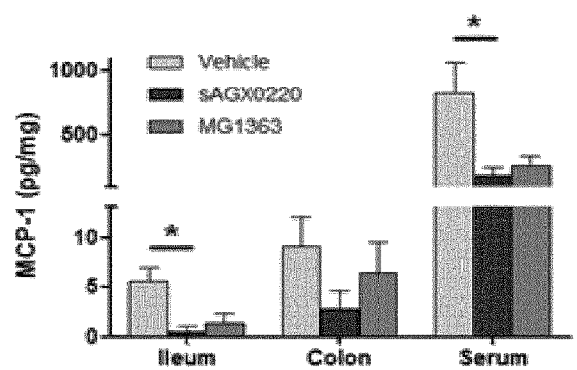
Figure 14:
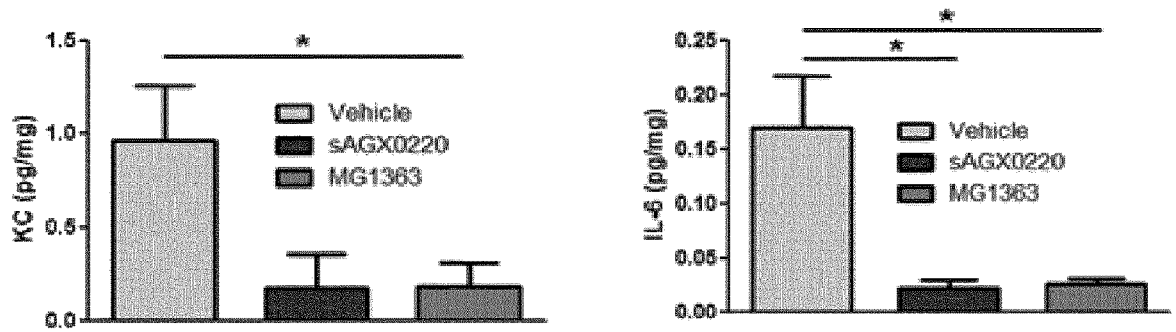
Figure 14:
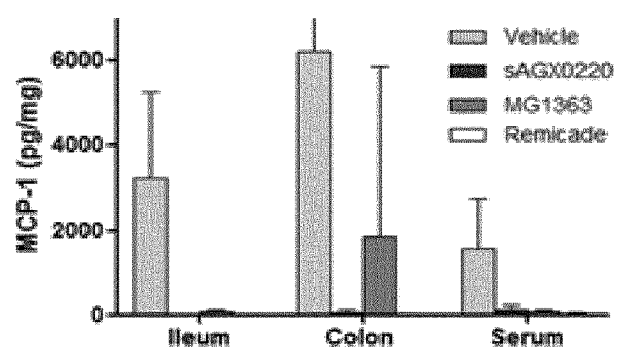
Figure 14:
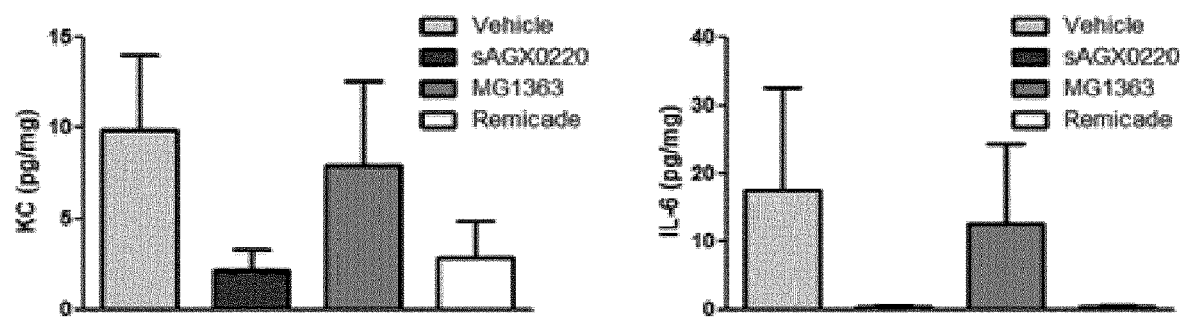

FIG. 14: Effect of anti-hTNF producing *L. lactis* bacteria (sAGX0220) on hTNF-induced toxicity and inflammatory cytokine production in A20$^{IEC-KO}$ mice. (a) A20$^{IEC-KO}$ mice (n=5 per group) were pretreated with vehicle, sAGX0220 or MG1363 1 hour before injection with 2 μg (left panel) and 6 μg (right panel) of recombinant hTNF and body temperature was followed in time. One group of A20$^{IEC-KO}$ mice was injected with Remicade prior to injection with 6 μg hTNF. (b) MCP-1 levels in ileum, proximal colon and serum 5 h after injection with 2 μg of hTNF. (c) KC and IL-6 levels in ileal homogenates 5 h after injection with 2 μg hTNF. (d) MCP-1 levels in ileum, proximal colon and serum 5 h after injection with 6 μg of hTNF. (e) KC and IL-6 levels in ileal homogenates 5 h after injection with 6 μg of hTNF. Error bars represent SEM. *, p<0.05.

Figure 15:
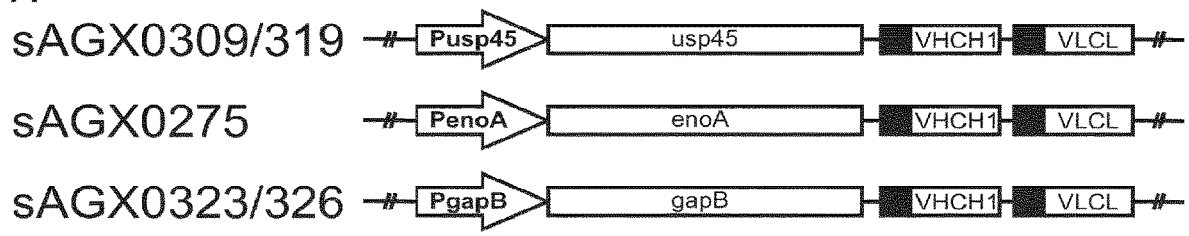
Figure 15:
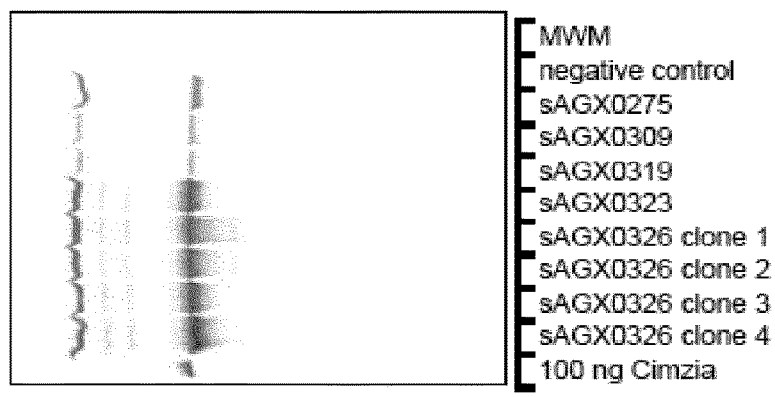
Figure 15:
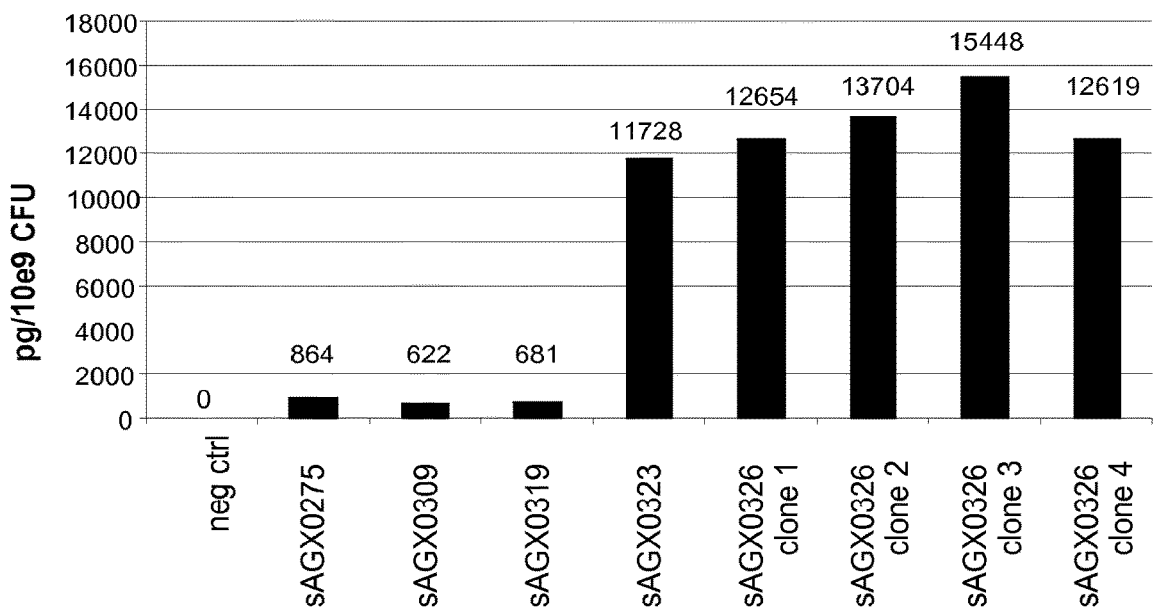
Figure 15:
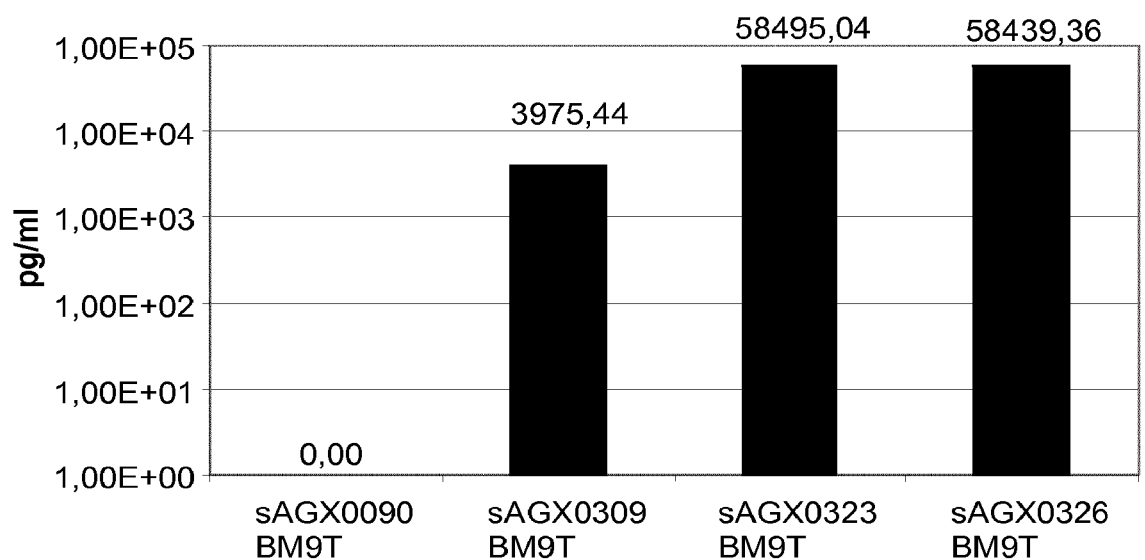
Figure 15:
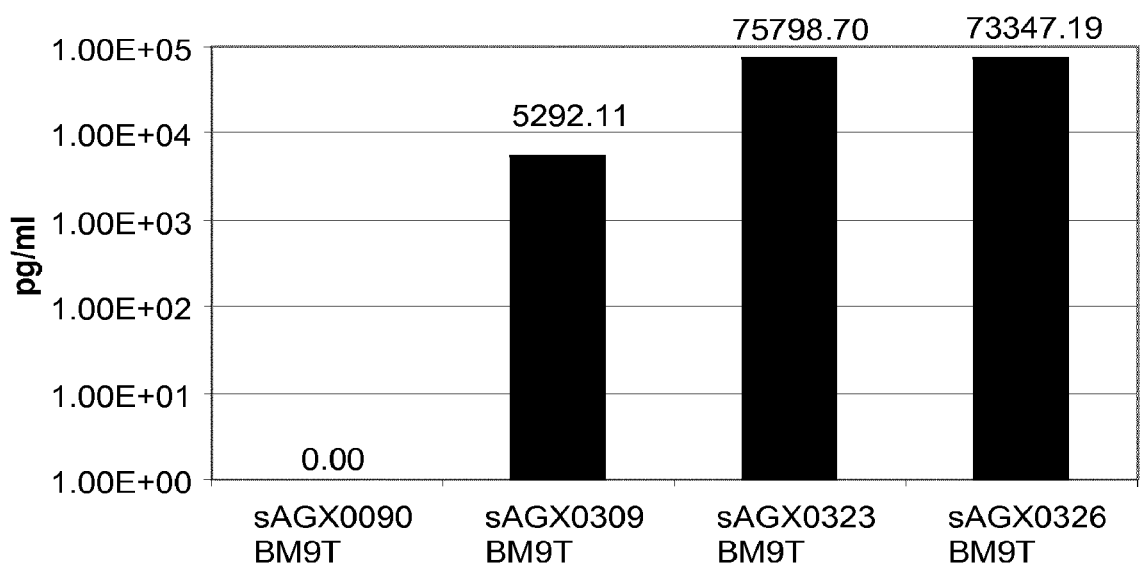
Figure 15:
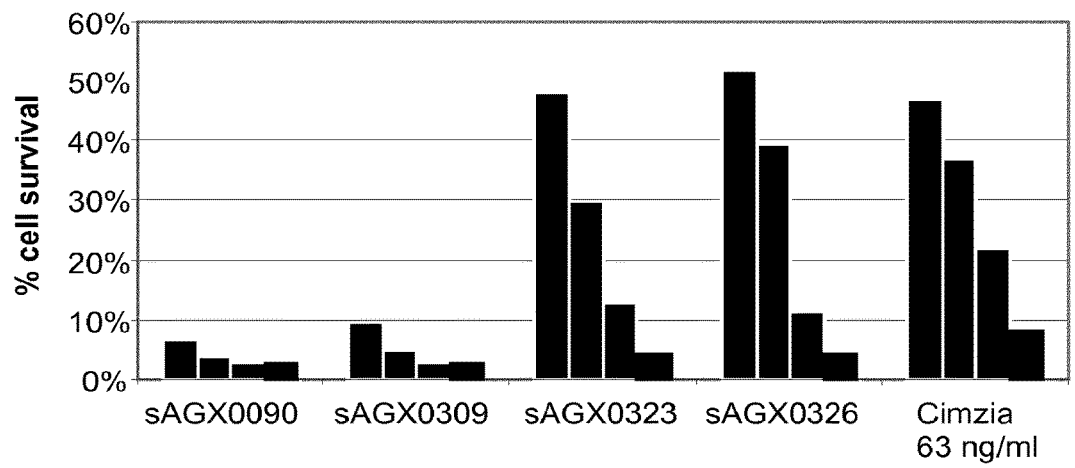

FIG. 15: CDP870 production in strains according to an embodiment of the invention. (A) CDP870 heavy chain and light chain integrated in the usp45 locus, the enoA locus or the gapB locus. (B) Western blot analysis indicating CDP870 expression in different strains according to an embodiment of the invention. (C) and (D) ELISA analysis indicating CDP870 expression in different strains according to an embodiment of the invention. (E) TNF neutralizing activity of different strains according to an embodiment of the invention.

Figure 16:
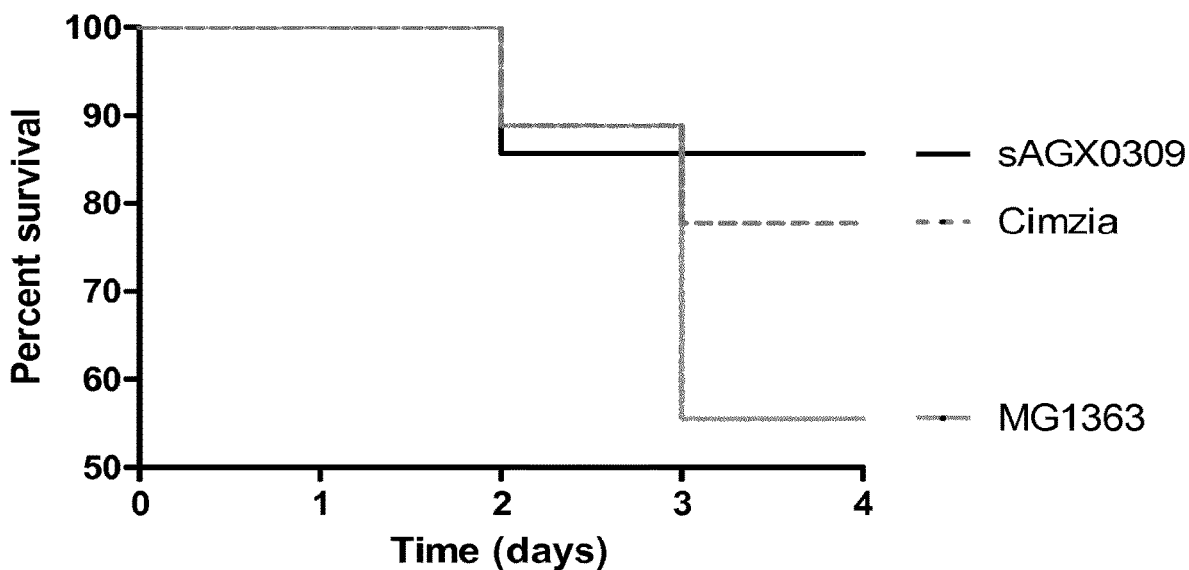

FIG. 16: Survival of Tg1278 mice with induced TNBS colitis after treatment with a strain according to an embodiment of the invention (anti-hTNF-secreting *L. lactis* strain sAGX0309) in comparison with mice treated with a wild type *L. lactis* strain and mice treated with Cimzia.

Figure 17:
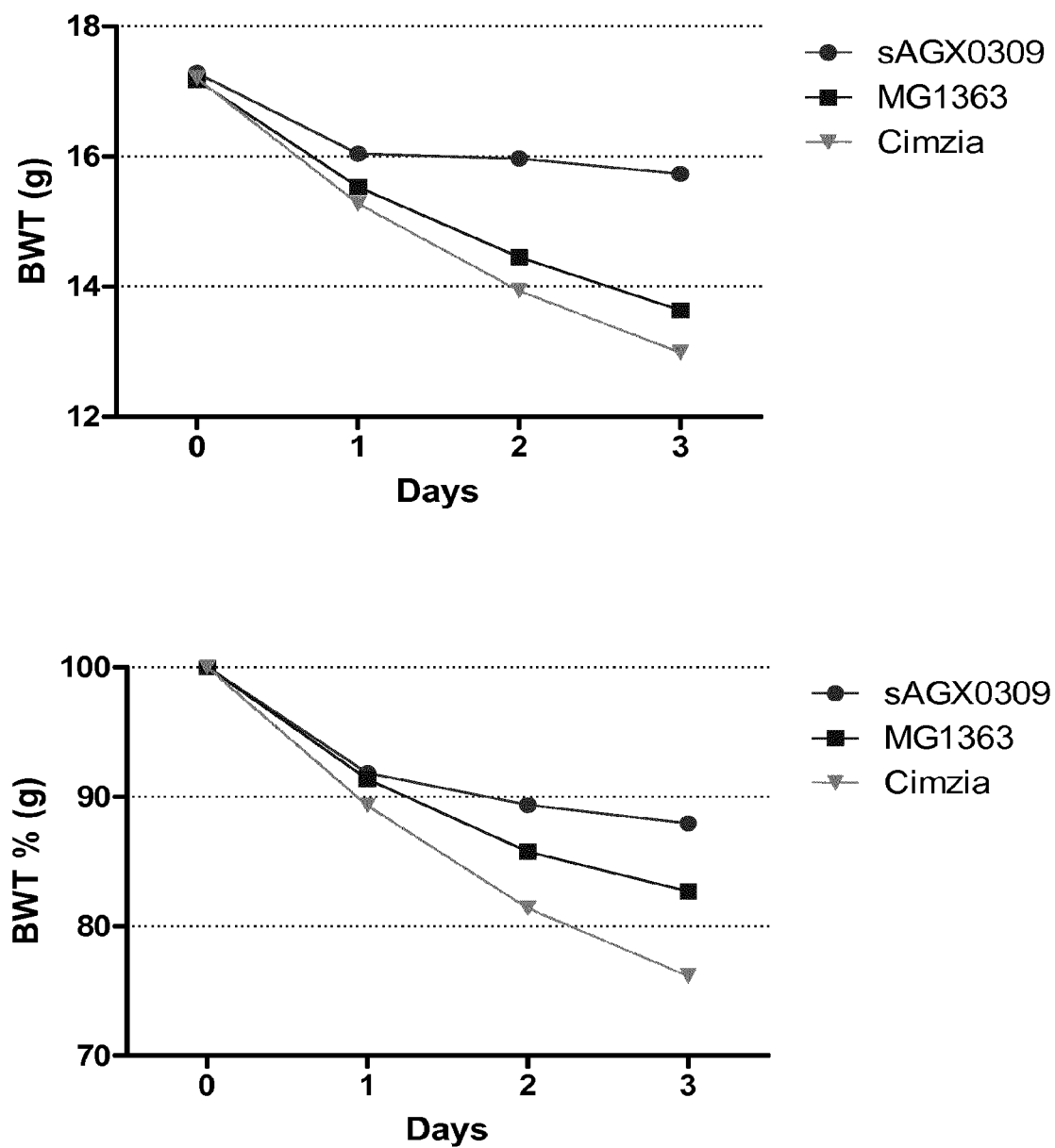

FIG. 17: Body weight evolution of Tg1278 mice with induced TNBS colitis after treatment with a strain according to an embodiment of the invention (anti-hTNF-secreting *L. lactis* strain sAGX0309) in comparison with mice treated with a wild type *L. lactis* strain and mice treated with Cimzia. Top panel: absolute body weight (g); bottom panel: body weight relative to starting body weight (%).

Figure 18:
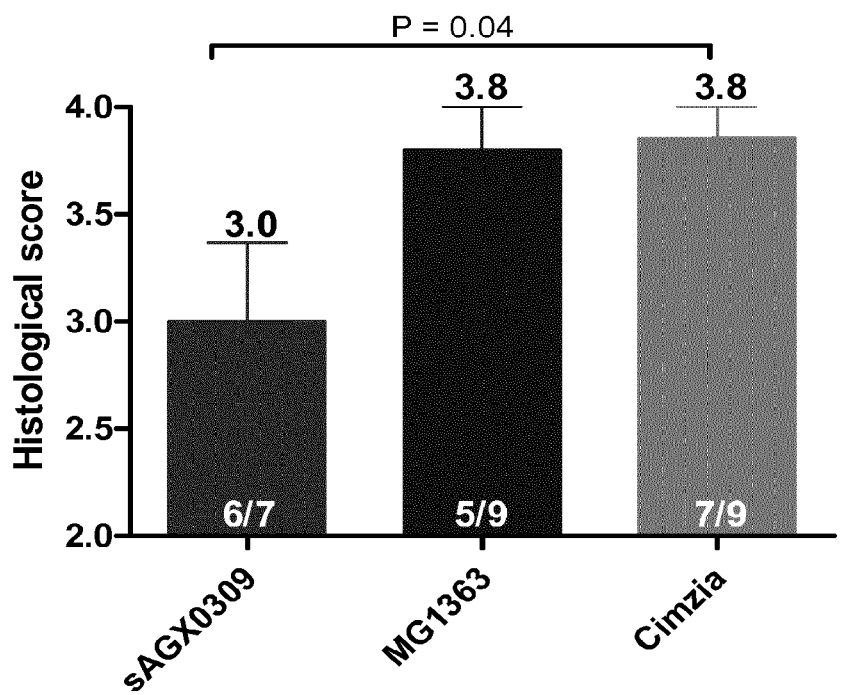

FIG. 18: Histological score of colon tissue of Tg1278 mice with induced TNBS colitis after treatment with a strain according to an embodiment of the invention (anti-hTNF-secreting *L. lactis* strain sAGX0309) in comparison with mice treated with a wild type *L. lactis* strain and mice treated with Cimzia. Mean values are indicated above bars. Survival rate is indicated per group.

Figure 19:
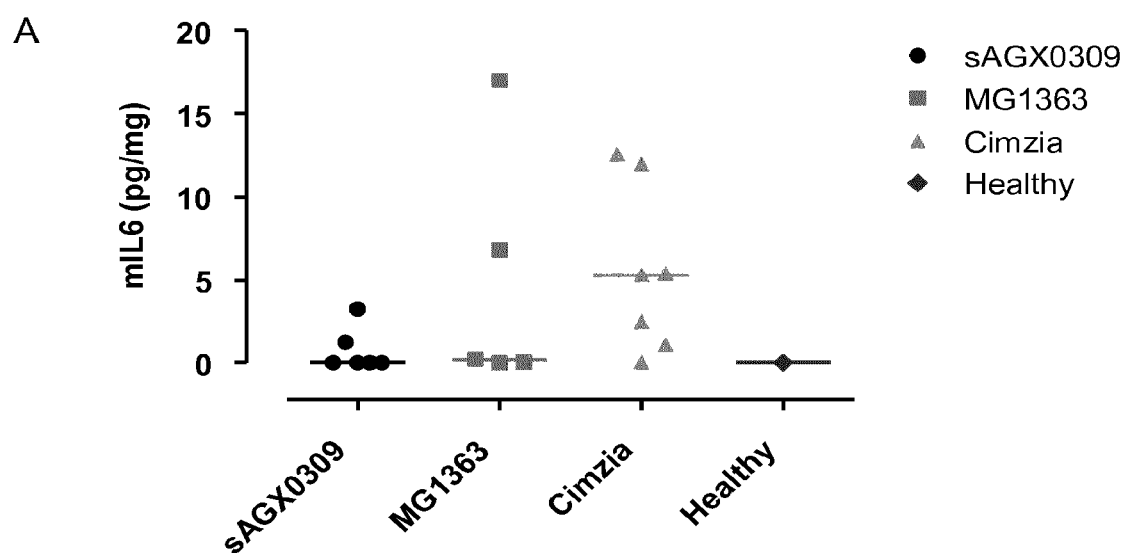
Figure 19:
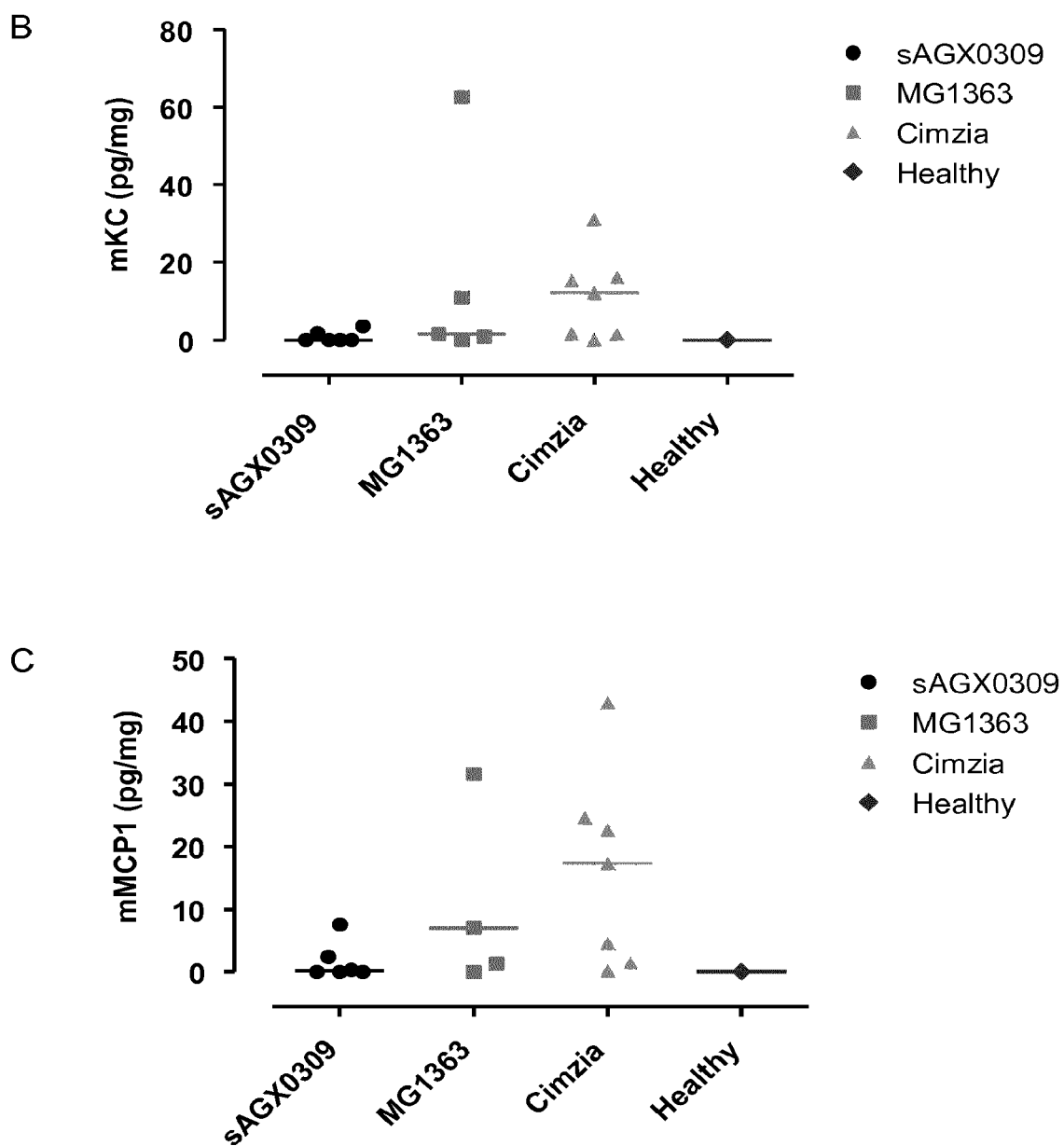

FIG. 19: Proinflammatory cytokine secretion in Tg1278 mice with induced TNBS colitis after treatment with a strain according to an embodiment of the invention (anti-hTNF-secreting *L. lactis* strain sAGX0309) in comparison with healthy mice, mice treated with a wild type *L. lactis* strain and mice treated with Cimzia. (A), (B), and (C) represent mIL6, mKC, and mMCP1 levels in pg/mg in the distal colon, respectively.

DETAILED DESCRIPTION OF THE INVENTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of", "consists essentially" and "consists essentially of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the following detailed description of the invention, reference is made to the accompanying drawings that form a part hereof, and in which are shown by way of illustration only of specific embodiments in which the invention may be practiced. It is to be understood that other embodiments may be utilised and structural or logical changes may be made without departing from the scope of the present invention. The following detailed description, therefore, is not to be taken in a limiting sense, and the scope of the present invention is defined by the appended claims.

Standard reference works setting forth the general principles of recombinant DNA technology include Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates) ("Ausubel et al. 1992"); Innis et al., PCR Protocols: A Guide to Methods and Applications, Academic Press: San Diego, 1990. General principles of microbiology are set forth, for example, in Davis, B. D. et al., Microbiology, 3rd edition, Harper & Row, publishers, Philadelphia, Pa. (1980).

As noted an aspect of the invention relates to a gram-positive bacterium comprising an endogenous gene to which one or more exogenous genes are transcriptionally or translationally coupled. Preferably, the one or more exogenous genes are transcriptionally or translationally coupled downstream (i.e. at the 3' end) of the endogenous gene. A related aspect provides a gram-positive bacterium comprising a polycistronic expression unit, said polycistronic expression unit comprising an endogenous gene and one or more exogenous genes. Preferably, the polycistronic expression unit consecutively comprises one or more endogenous genes and one or more exogenous genes. A further aspect provides a recombinant nucleic acid comprising a polycistronic expression unit comprising a gene endogenous to a gram-positive bacterium to which one or more genes exogenous to the gram-positive bacterium are transcriptionally or translationally coupled. Preferably, the one or more exogenous genes are transcriptionally or translationally coupled downstream (i.e. at the 3' end) of the endogenous gene.

Preferably, the one or more exogenous gene(s) is (are) the most 3' genes of the polycistronic expression unit, i.e. the one or more exogenous gene(s) is (are) the last or most downstream gene(s) of the polycistronic expression unit. For instance if the endogenous gene is monocistronic, the one or more exogenous gene is located after or downstream (i.e. at the 3' end) of—and transcriptionally coupled with—the open reading frame of the gene. Likewise, if the endogenous gene is itself polycistronic, such as (part of) an operon, the one or more exogenous gene is located after or downstream (i.e. at the 3' end) of the last (i.e. most downstream or most 3') endogenous gene of the endogenous polycistronic gene.

Most preferably, the endogenous gene as referred to herein throughout the description is monocistronic. The endogenous gene preferably thus does not form part of an endogenous operon.

Preferably, the expression of the polycistronic expression unit as described herein is effected by a promoter which may be or may exhibit one or more of the following characteristics: constitutive promoters, central metabolism gene promoters, essential gene promoters, strong promoters, housekeeping gene promoters, ribosomal gene promoters, glycolysis gene promoters. Most preferably, the promoter is a constitutive promoter.

As used herein, the term "gram-positive bacterium" has its common meaning known in the art. By means of further guidance, a gram-positive bacterium can be identified by Gram staining as retaining crystal violet stain.

In a preferred embodiment, the gram-positive bacterium according to the invention is non-pathogenic in the sense that it does not cause harm or does not lead to deleterious effects when administered to an intended subject.

Preferably, the gram-positive bacterium according to the invention is a lactic acid bacterium (LAB), including, but not limited to the genera *Lactococcus, Lactobacillus, Leuconostoc, Pediococcus, Streptococcus, Aerococcus, Carnobacterium, Enterococcus, Oenococcus, Sporolactobacillus, Tetragenococcus, Vagococcus*, and *Weisella*. More preferably, the LAB is a *Lactococcus* species, such as, but not limited to *Lactococcus lactis, Lactococcus garvieae, Lactococcus piscium, Lactococcus plantarum* and *Lactococcus raffinolactis*, and any subspecies and strains thereof. Most preferably, the *Lactococcus* species is *Lactococcus lactis*, and any subspecies and strain thereof, such as without limitation *Lactococcus lactis* ssp. *cremoris, Lactococcus lactis* ssp. *hordniae, Lactococcus lactis* ssp. *lactis, Lactococcus lactis* ssp. bv. *diacetylactis*. In further preferred embodiments of the invention the *Lactococcus lactis* is *Lactococcus lactis* ssp. *cremoris* or *Lactococcus lactis* ssp. *lactis*, more preferably *Lactococcus lactis* ssp. *cremoris*, and encompasses any strains thereof, such as, e.g., *Lactococcus lactis* ssp. *cremoris* SK11, *Lactococcus lactis* ssp. *cremoris* MG1363, or *Lactococcus lactis* ssp *lactis* IL1403. In another preferred embodiment, the LAB is an *Enterococcus* sp., preferably *Enterococcus faecalis, Enterococcus faecium* and any subspecies and strains thereof, such as, without limitation *Enterococcus faecium* strain LMG15709.

In another preferred embodiment, the gram-positive bacterium according to the invention is *Bifidobacterium*.

*Bifidobacterium* is a genus of Gram-positive, non-motile, often branched anaerobic bacteria. Bifidobacteria as used herein may include *B. adolescentis, B. angulatum, B. animalis, B. asteroides, B. bifidum, B. boum, B. breve, B. catenulatum, B. choerinum, B. coryneforme, B. cuniculi, B. denticolens, B. dentium, B. gallicum, B. gallinarum, B. indicum, B. infantis, B. inopinatum, B. lactis, B. longum, B. magnum, B. merycicum, B. minimum, B. pseudocatenulatum, B. pseudolongum, B. pullorum, B. ruminantium, B. saeculare, B. subtile, B. suis, B. thermacidophilum, B. thermophilum*. Preferably, the *Bifidobacterium* is *B. adolescentis, B. bifidum, B. breve, B. infantis, B. longum*. It is to be understood that all subspecies and strains of Bifidobacteria are also included.

As used herein, the term "consecutively" in the context of endogenous and exogenous genes refers to the 5' to 3' order of the respective genes in a polynucleic acid, vector or chromosome. For example, a polycistronic expression unit consecutively comprising one or more endogenous genes and one or more exogenous genes relates to a unit in which the one or more endogenous genes are positioned upstream of the one or more exogenous genes. Hence the one or more exogenous genes are positioned after the 3' end of the one or more endogenous genes. It is to be understood that the consecutive coupling or ordering as described herein does not necessarily imply a direct coupling of the endogenous and exogenous gene. Additional sequences may be present between the endogenous and exogenous gene. As an example, an intergenic region as defined further herein may be present between (i.e. downstream or 3' of the endogenous gene and upstream or 5' of the exogenous gene) the consecutive endogenous and exogenous genes. As used herein, the terms "endogenous gene", "endogenous promoter", "endogenous intergenic region", "endogenous ribosome binding site" refer to respectively a gene, promoter, intergenic region or ribosome binding site which are native to a gram-positive bacterium, or can be found in nature in a gram-positive bacterium. As such, the term endogenous gene, promoter, intergenic region or ribosome binding site encompasses orthologous genes, promoters, intergenic regions, and ribosome binding sites between different genera, species, subspecies or strains of gram-positive bacteria. In particular, a gene, promoter, intergenic region or ribosome binding site isolated from one genus, species, subspecies, or strain of gram-positive bacteria is said to be endogenous for all other genera, species, subspecies, or strains of gram-positive bacteria, irrespective of possible polynucleic acid sequence differences, provided said other genus, species, subspecies, or strain of gram-positive bacteria in nature also comprises such gene, promoter, intergenic region or ribosome binding site. Thus, such divergent but found-in-nature gene, promoter, intergenic region, or ribosome binding site sequences would be considered endogenous. By means of example, and without limitation, the gene encoding enolase, enoA, which is isolated from *Lactococcus lactis* ssp. *lactis* is also considered endogenous in respect of *Lactococcus lactis* ssp. *cremoris*.

Preferably, however, an "endogenous" gene, promoter or intergenic region of a given genus, species, subspecies or strain of gram-positive bacterium as intended herein may denote a gene, promoter or intergenic region which is found in nature in, i.e., is native to or own to, that same genus, species, subspecies or strain of gram-positive bacterium, respectively. By means of example, and without limitation, the gene encoding enolase, enoA, which is isolated from *Lactococcus lactis* ssp. *lactis* may preferably be considered "endogenous" to *Lactococcus lactis* ssp. *lactis*, but not to *Lactococcus lactis* ssp. *cremoris*.

As used herein, the term "exogenous gene" refers to a gene which is not native to a gram-positive bacterium, or cannot be found in nature in a gram-positive bacterium. The term exogenous gene is synonymous with the term heterologous gene. The exogenous gene may be a full length gene or may alternatively be a truncated gene or a gene fragment. By means of example, a exogenous gene can be derived from viruses, other prokaryotes, such as a gram-negative bacterium, or alternatively and preferably can be derived from eukaryotes, such as plants, animals, preferably mammals, most preferably human. Alternatively, the exogenous gene can be completely or partially synthetic or artificial, in the sense that it completely or partially does not occur in nature. In addition, the exogenous gene can be chimeric, in the sense that it can be composed of sequences originating from different species or a combination of naturally occurring and synthetic or artificial sequences. Also encompassed are chimeric sequences composed of gram-positive bacterial sequences and sequences exogenous of gram-positive bacteria, such as for instance sequences encoding fusion proteins composed of gram-positive bacterial secretion signal peptides and exogenous proteins.

As eukaryotic genes for the most part comprise introns beside exons, the skilled person will appreciate that according to the invention, any reference to a exogenous gene relates to the intron-less open reading frame of such gene, i.e., the protein-coding sequence of such gene. The term "open reading frame" or ORF refers to a succession of coding nucleotide triplets starting with a translation initiation codon (e.g. ATG or GTG) and closing with a translation termination codon (e.g., TAA, TAG or TGA) and encoding a single polypeptide.

Prokaryotic genes, in particular genes from gram-positive bacteria do not comprise introns. Hence, the coding sequence or open reading frame of a prokaryotic gene corresponds to the succession of coding nucleotide triplets starting with a translation initiation codon and closing with a translation termination codon as located on the prokaryotic genome, in particular the bacterial chromosome.

Accordingly, in an aspect, the invention relates to a gram-positive bacterium comprising an endogenous open reading frame or coding sequence to which one or more exogenous open reading frame or coding sequences are transcriptionally or translationally coupled.

The skilled person will understand that, whereas the term "gene" in general may refer to a locatable region of genomic sequence, corresponding to a unit of inheritance, which is associated with transcriptional and translational regulatory regions such as the pribnow box, shine-dalgarno sequence, operators, terminators, transcribed regions, and or other functional sequence regions, any reference to the term "gene" in the context of exogenous sequences as described herein preferably refers to the coding sequence or open reading frame of that gene, unless explicitly stated to the contrary. Any reference to the term "gene" in the context of endogenous sequences as described herein may refer to a locatable region of genomic sequence, corresponding to a unit of inheritance, which is associated with regulatory regions, transcribed regions, and or other functional sequence regions, but alternatively may also refer to the coding sequence or open reading frame of that gene.

As used herein, the term "translationally coupled" is synonymous with "translationally linked" or "translationally connected". These terms in essence relate to polycistronic expression systems or units. Two or more genes, open reading frames or coding sequences are said to be translationally coupled when common regulatory element(s) such as in particular a common promoter effects the transcription of said two or more genes as one mRNA encoding said two or more genes, open reading frames or coding sequences, which can be subsequently translated into two or more individual polypeptide sequences. The skilled person will appreciate that bacterial operons are naturally occurring polycistronic expression systems or units in which two or more genes are translationally or transcriptionally coupled. According to the invention, transcriptional coupling underlies translational coupling.

Accordingly, in an aspect, the invention relates to a gram-positive bacterium comprising an endogenous gene to which one or more exogenous genes, open reading frame or coding sequence are transcriptionally coupled. Preferably, the gram-positive bacterium consecutively comprises an endogenous gene to which one or more exogenous genes, open reading frame or coding sequence are transcriptionally coupled. As used herein, the term "transcriptionally coupled" is synonymous with "transcriptionally connected" and "transcriptionally linked". These terms generally refer to polynucleic acid sequences comprising two or more open reading frames or coding sequences which are commonly transcribed as one mRNA, and which can be translated into two or more individual polypeptides.

In other aspects, the invention relates to a gram-positive bacterium or recombinant nucleic acid comprising a polycistronic expression unit, said polycistronic expression unit comprising an endogenous gene and one or more exogenous genes, open reading frame or coding sequence.

As used herein, the term "polycistronic expression unit" or "polycistronic expression system" refers to a unit wherein the expression of two or more genes is regulated by common regulatory mechanisms, such as promoters, operators, and the like. The term polycistronic expression unit as used herein is synonymous with multicistronic expression unit. Examples of polycistronic expression units are without limitation bicistronic, tricistronic, tetracistronic expression units. Any mRNA comprising two or more, such as 3, 4, 5, 6, 7, 8, 9, 10, or more, open reading frames or coding regions encoding individual expression products such as proteins, polypeptides and/or peptides is encompassed within the term polycistronic.

In an embodiment, the translationally or transcriptionally coupled one or more endogenous genes and one or more exogenous genes as described herein are transcriptionally controlled by a promoter which is endogenous to a gram-positive bacterium. In another embodiment, the polycistronic expression unit or system as described herein is transcriptionally controlled by a promoter which is endogenous to a gram positive bacterium.

By "promoter" is meant generally a region on a nucleic acid molecule, preferably DNA molecule, to which an RNA polymerase binds and initiates transcription. A promoter is preferably, but not necessarily, positioned upstream, i.e., 5', of the sequence the transcription of which it controls.

In a further embodiment, the translationally or transcriptionally coupled one or more endogenous genes and one or more exogenous genes as described herein are transcriptionally controlled by the native promoter of (one of) said one or more endogenous genes. In another embodiment, the polycistronic expression unit or system as described herein is transcriptionally controlled by the native promoter of (one of) said one or more endogenous genes comprised in said polycistronic expression system or unit. In another embodiment, the polycistronic expression unit or system as described herein is operably linked to a gram-positive endogenous promoter.

As used herein, the term "operably linked" or "operable linkage" is a linkage in which the regulatory DNA sequences and the DNA sequence sought to be expressed are connected in such a way as to permit expression. For example, a promoter is said to be operably linked to a gene, open reading frame or coding sequence, if the linkage or connection allows or effects transcription of said gene. In a further example, a 5' and a 3' gene, cistron, open reading frame or coding sequence are said to be operably linked in a polycistronic expression unit, if the linkage or connection allows or effects translation of at least the 3' gene.

For example, DNA sequences, such as, e.g., preferably a promoter and an open reading frame, are said to be operably linked if the nature of the linkage between the sequences does not (1) result in the introduction of a frame-shift mutation, (2) interfere with the ability of the promoter to direct the transcription of the open reading frame, or (3) interfere with the ability of the open reading frame to be transcribed by the promoter region sequence.

In an exemplary preferred embodiment, the promoter may be positioned upstream of, i.e., 5' of, the open reading frame(s) to which it is operably linked.

The skilled person will appreciate that the promoter may be associated with additional native regulatory sequences or regions, e.g. operators. The precise nature of the regulatory regions needed for expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the Pribnow-box (cf. TATA-box), Shine-Dalgarno sequence, and the like.

In a further embodiment, the promoter is the native promoter of the 5' most, i.e., most upstream, endogenous gene in the polycistronic expression unit.

As used herein, the term "constitutive" in the context of a promoter (or by extension relating to gene expression of the endogenous gene) refers to a promoter that allows for continual transcription of its associated gene. In particular, transcription of the associated gene or genes under control of such promoter occurs independently of any inducer or other regulatory signal.

As used herein, the term "housekeeping gene" or "housekeeping promoter" refers to a gene or a promoter of a gene that is required for the maintenance of basic cellular function. Although some housekeeping genes are expressed at relatively constant levels, other housekeeping genes may vary depending on external or experimental conditions. Housekeeping genes may for instance be involved in metabolism, gene expression (such as basal transcription machinery), signalling, but may also be structural genes.

As used herein, "glycolysis gene" or "glycolysis promoter" refers to a gene or promoter of a gene involved in the glycolytic pathway, and include the promoters of the genes encoding glycolytic enzymes, particularly hexokinase, phosphoglucose isomerase, phosphofructokinase, fructose bisphosphate aldolase, triosephosphate isomerase, glyceraldehyde phosphate dehydrogenase, phosphoglycerate kinase, phosphoglycerate mutase, enolase, and pyruvate kinase.

As used herein, "ribosomal gene" or "ribosomal promoter" refers to a gene or promoter of a ribosomal gene, including genes encoding ribosomal proteins as well as genes transcribed into ribosomal RNA. Preferably, it may refer to a gene or promoter of a ribosomal protein.

As used herein, "central metabolism gene" or "central metabolism promoter" or alternatively "basic metabolism gene" or "basic metabolism promoter" refers to a gene or promoter of a gene involved in critical metabolic pathways, and includes genes involved in glycolysis, pentose-phosphate pathway, and tricaboxylic acid (TCA) cycle.

As used herein, the term "essential" in the context of a gene (or by extension relating to the promoter of such gene) relates to a gene the absence of the native expression product of which is detrimental, such as in particular lethal, for the host or alternatively alters, inhibits or prevents, normal physiology or function, such as in particular propagation or growth. It is to be understood that, as used herein, the term "essential" in the context of a gene or promoter of a gene relates to constitutively essential, as opposed to conditionally essential. For instance, the genes of the lactose operon, such as the beta-galactosidase gene, in several gram-positive bacteria, in particular lactic acid bacteria such as *Lactococcus* sp. may be essential when the bacteria are cultivated in a medium containing lactose as the main or sole carbon source, these genes are not essential when the bacteria are cultivated in a medium containing alternative carbon sources. These genes are therefore only conditionally essential, but not constitutively essential, as intended herein.

In a preferred embodiment, the endogenous promoter and/or the endogenous gene as described herein is selected from the group comprising or consisting of gram-positive bacterial promoters and/or genes corresponding to the following *Lactococcus* promoters and/or genes, more particularly *Lactococcus lactis* ssp. *cremoris* strain MG1363 promoters and/or genes: 1) DNA-directed RNA polymerase, beta' subunit/160 kD subunit (rpoC), 2) DNA-directed RNA polymerase, beta subunit/140 kD subunit (rpb2 or rpoB), 3) DNA-binding ferritin-like protein (oxidative damage protectant) (dps), 4) pyruvate kinase (pyk), 5) glutamyl- and glutaminyl-tRNA synthetases (glnS or gltX), 6) enolase (eno), 7) glutamine synthetase (glnA) 8) HTH-type transcriptional regulator (glnR), 9) Xaa-His dipeptidase (argE or pepV), 10) FOF1-type ATP synthase beta subunit (ATP synthase F1 beta subunit) (atpD), 11) 3-phosphoglycerate kinase (pgk), 12) glyceraldehyde-3-phosphate dehydrogenase/erythrose-4-phosphate dehydrogenase (gapA or gapB), 13) acetate kinase (ackA), 14) 3-oxoacyl-(acyl-carrier-protein) synthase (fabB or fabF), 15) 3-oxoacyl-(acyl-carrier-protein) reductase (fabG), 16) DNA-directed RNA polymerase, alpha subunit/40 kD subunit (rpoA), 17) Xaa-Pro aminopeptidase (pepP), 18) fructose/tagatose bisphosphate aldolase (tbp or fbaA), 19) ribosomal protein S4 (rpsD), 20) superoxide dismutase (sodA), 21) ribosomal protein S12 (rpsL) and ribosomal protein S7 (rpsG), 22) ribosomal protein L18 (rpiR) and ribosomal protein S5 (rpsE) and ribosomal protein L30/L7E (rpmD), 23) S-ribosylhomocysteine lyase (luxS), 24) ribosomal protein L19 (rpIS), 25) ribosomal protein S11 (rpsK), 26) ribosomal protein L10 (rplJ), 27) ribosomal protein L7/L12 (rpiL), 28) bacterial nucleoid DNA-binding protein/DNA binding protein HU (hup or hI/A), 29) 50S ribosomal protein L28 (rpmB), 30) phosphotransferase system cellobiose-specific component IIB (lace or ptcB), 31) FOF1-type ATP synthase alpha subunit (atpA), 32) ABC-type sugar transport system (ATPase component) (malK or msmK), 33) acetoin dehydrogenase complex E1 component alpha subunit (acoA or pdhA), 34) cell division protein (diflVA or ftsA), 35) UDP-galactopyranose mutase (glf), 36) glutamyl aminopeptidase (frvX or pepA), 37) predicted dehydrogenase related protein (mviM or llmg_0272), 38) ribosomal protein S2 (rpsB), 39) translation initiation factor 3 (IF-3) (infC), 40) ribosomal protein L4 (rp/D) and ribosomal protein L23 (rplW) and ribosomal protein L2 (rp/B), 41) EMAP domain (ydjD), 42) transcription elongation factor (greA), 43) protease subunit of ATP-dependent Clp protease (c/pP), 44) ribosomal protein L15 (rplO), 45) ribosomal protein L11 (rplK), 46) ribosomal protein S8 (rpsH), 47) ribosomal protein L21 (rplU), 48) ribosomal protein S13 (rpsM), 49) ribosomal protein S19 (rpsS) and ribosomal protein L22 (rplU or rplV) and ribosomal protein L16 (rplP) and ribosomal protein L14 (rplN), 50) ribosomal protein S10 (rpsJ), 51) co-chaperonin GroES (Hsp10) (cpn10), 52) ribosomal protein L24 (rplX), 53) hypothetical protein LACR_0137 (duf965), and 54) secreted 45 kDa protein (usp45). Preferably, the endogenous promoter and/or endogenous gene is selected from the group comprising or consisting of enoA, usp45, gapB, pyk, rpmB, and rplS. These promoters and their sequences are disclosed for example in WO 2008/08411 incorporated by reference herein, e.g., in Table 1 and FIG. 1A-H thereof. In an embodiment, the invention relates to a gram positive bacterium or a recombinant nucleic acid as described herein, wherein the endogenous gene and the one or more exogenous genes are transcriptionally controlled by a promoter endogenous to the gram-positive bacterium, preferably by an endogenous promoter selected from the group consisting of the promoter of eno, usp45, gap, pyk, rpmB and rplS of said gram-positive bacterium. In a further embodiment, the endogenous gene is located in its native chromosomal locus in the gram-positive bacterium.

In a preferred embodiment, said one or more exogenous genes, open reading frames or coding sequences are translationally or transcriptionally coupled to the 3' end of said one or more endogenous genes, open reading frame or coding sequence. Accordingly, in an embodiment, the invention provides for a gram-positive bacterium comprising a polycistronic expression unit, wherein said polycistronic expression unit comprises one or more 5' endogenous gene and one or more 3' exogenous gene. Preferably, the 5' most gene of the polycistronic expression unit is an endogenous gene. By means of example, and without limitation, the polycistronic expression unit may comprise or consist essentially of from 5' end to 3' end an endogenous gene followed by one or more endogenous genes, followed by one or more exogenous genes. Alternatively, and without limitation, the polycistronic expression unit may comprise or consist essentially of from 5' end to 3' end an endogenous gene followed by one or more exogenous genes. Alternatively, the polycistronic expression unit may comprise or consist essentially of from 5' end to 3' end an endogenous gene followed by one or more exogenous genes, followed by one or more endogenous genes.

The translationally coupled or transcriptionally coupled one or more endogenous genes and one or more exogenous genes, or the polycistronic expression unit or system, as described herein may be comprised in a replicon which allows maintenance and/or propagation and expression of the endogenous and exogenous genes in the gram-positive bacteria according to the invention as described herein.

In an embodiment, the translationally coupled or transcriptionally coupled one or more endogenous genes and one or more exogenous genes, optionally including the (endogenous) promoter as described elsewhere in this specification, or the polycistronic expression unit or system, as described herein may be comprised in a vector, preferably an expression vector allowing expression in gram-positive bacteria. Accordingly, the invention also relates to a vector comprising the recombinant nucleic acid as described herein.

As used herein, "vector" refers to a nucleic acid molecule, typically DNA, to which nucleic acid fragments may be inserted and cloned, i.e., propagated. Hence, a vector will typically contain one or more unique restriction sites, and may be capable of autonomous replication in a defined host or vehicle organism such that the cloned sequence is reproducible. Vectors may include, without limitation, plasmids, phagemids, bacteriophages, bacteriophage-derived vectors, PAC, BAC, linear nucleic acids, e.g., linear DNA, etc., as appropriate (see, e.g., Sambrook et al., 1989; Ausubel 1992).

Factors of importance in selecting a particular vector, e.g., a plasmid, include inter alia: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pUC19, etc.). Such plasmids are describe in, e.g., Sambrook et al., 1989; Ausubel 1992. Particularly preferred vectors may be those able to replicate in *E. coli* (or other Gram negative bacteria) as well as in another host cell of interest, such as in a Gram positive bacterium, a lactic acid bacterium, preferably *Lactococcus*, more preferably *Lactococcus lactis* (see, e.g., Kok et al. *Appl. Environ. Microbiol.*, 1984, vol. 48(4), 726-31). Other preferred vectors may be those able to replicate and/or shuttle between one or more Gram positive bacteria but not in Gram negative bacteria. In a preferred embodiment, the vector is pT1NX as described by Steidler et al. *Appl. Environ. Microbiol.*, 1995, vol. 61(4), 1627-1629, which is specifically incorporated by reference herein.

In another embodiment, the translationally coupled or transcriptionally coupled one or more endogenous genes and one or more exogenous genes, or the polycistronic expression unit or system, as described herein are integrated in the gram-positive bacterial genome or chromosome. Methods for obtaining recombinant gram-positive bacteria and random as well as homologous recombination are well-known in the art, as well as vectors for effecting recombination. By means of further guidance, such methods and vectors are for instance disclosed in Steidler et al. (2003, Nature Biotechnology, 21:785-789), Law et al. (1995, J Bacteriol, 177(24): 7011-7018), Leenhouts et al. (1998, Methods in Cell Science, 20:35-50) and WO 2004/046346, which are incorporated in its entirety by reference. Preferably, the polycistronic expression unit as described herein is generated or introduced by site-directed integration of the requisite sequences in the bacterial chromosome by homologous recombination.

In an embodiment, a recombination vector comprises an endogenous promoter as described elsewhere in this specification, and optionally additional regulatory sequences, as well as a polycistronic expression unit as described herein. Preferably, the endogenous promoter and the polycistronic expression unit are operably linked. Homologous recombination can be effected at a predetermined locus. Such system is highly modular and allows for individual selection and combination of promoter, regulatory sequences, endogenous gene, and exogenous gene, as well as the choice of insertion site.

In another embodiment, the gram-positive bacterium according to the invention comprises an endogenous promoter as described elsewhere in this specification at its native locus, i.e., in its native genomic context on the bacterial chromosome, to which a polycistronic expression unit comprising one or more endogenous genes, open reading frame or coding sequence and one or more exogenous genes, open reading frame or coding sequence are operably linked. The operable linkage can be effected through homologous recombination between the locus comprising the promoter and a recombination vector comprising the polycistronic expression unit, flanked by sequences configured to effect said homologous recombination. Accordingly, in an embodiment, the invention relates to a gram-positive bacterium as described herein, wherein the endogenous gene is transcriptionally coupled to the one or more exogenous genes by chromosomally integrating the one or more exogenous genes to said locus, preferably by chromosomally integrating the one or more exogenous genes 3' of the endogenous gene in said locus.

Vector design can be chosen such that merely the open reading frame or coding sequences of the endogenous and/or exogenous genes are integrated into the intended chromosomal locus. In this case, the regulatory sequences beside the promoter per se which effect transcription and/or translation, e.g. operators, transcription initiation site, shine-dalgarno sequence, terminator sequence, etc. are provided for by the native genomic locus of the promoter. Alternatively, such sequences may be provided on the recombination vector comprising the polycistronic expression unit. In the latter case, depending on the needs, the native regulatory sequences associated with the endogenous promoter may be removed during homologous recombination. The systems described here are modular in respect of individual selection of endogenous gene, exogenous gene and possibly the regulatory sequences, but predetermine the insertion site at the endogenous locus of the selected promoter.

In a further embodiment, the gram-positive bacterium according to the invention comprises an endogenous promoter as well as one or more endogenous genes, both as described elsewhere in this specification, at its (their) native locus, i.e. in its (their) native genomic context on the bacterial chromosome, to which one or more exogenous genes, open reading frame or coding sequence are operably linked, such as to effect polycistronic expression of the one or more endogenous genes and the one or more exogenous genes. In this system, the endogenous promoter and one or more endogenous genes, as well as the regulatory sequences effecting transcription and translation of said one or more endogenous genes is present in their native locus. Such system maximally preserves the native character of the gram-positive bacterium.

A polycistronic expression unit comprises at least two genes, open reading frames or coding sequences. In order to initiate translation of all genes, each of these genes generally is associated with sequences effecting ribosome binding, i.e. ribosome binding sites. In prokaryotes, ribosome binding sites are denoted Shine-Dalgarno (SD) sequences, which have the general consensus sequence 5'-AGGAGG-3'. The SD sequence on average is located about 8 base pairs upstream (i.e. 5' of) the translation initiation codon or start codon. Depending on the distance (in amount of nucleotides) between the stop codon of the 5' gene and the start codon of the 3' gene, the SD sequences can be typically positioned 1) in an intergenic region between both genes, if the distance is at least the size of the SD sequence; 2) in an intergenic region between both genes, but overlapping with the stop codon of the 5' gene, in case of a smaller distance between 5' and 3' gene; or 3) 5' to the stop codon of the 5' gene, if for instance the stop codon of the 5' gene and the start codon of the 3' gene are very close or overlap.

In an embodiment, the invention relates to a gram-positive bacterium or a recombinant nucleic acid as described herein, further comprising one or more polynucleic acid sequences comprising a ribosome binding site configured to effect translation of the one or more exogenous genes. In another embodiment, the invention relates to a gram-positive bacterium or a recombinant nucleic acid as described herein, further comprising one or more ribosome binding site configured to effect translation of the one or more exogenous genes. In a further embodiment, the invention relates to a gram-positive bacterium or a recombinant nucleic acid as described herein wherein said one or more endogenous genes and said one or more exogenous genes are transcriptionally or translationally coupled by means of a ribosome binding site. In yet another embodiment, the invention relates to a gram-positive bacterium or a recombinant nucleic acid, comprising a polycistronic expression unit as described herein, wherein any 5' gene is coupled to a 3' gene by a polynucleic acid sequence comprising or consisting (essentially) of a ribosome binding site. In a preferred embodiment, said ribosome binding site is endogenous to a gram-positive bacterium. In a further preferred embodiment, said ribosome binding site is comprised in an intergenic region, preferably an operon intergenic region.

In another embodiment, the invention relates to a gram-positive bacterium or a recombinant nucleic acid as described herein, further comprising one or more polynucleic acid sequences comprising an intergenic region configured to effect translation of the one or more exogenous genes. In a further embodiment, the invention relates to a gram-positive bacterium or a recombinant nucleic acid as described herein, further comprising one or intergenic region configured to effect translation of the one or more exogenous genes. In a further embodiment, the invention relates to a gram-positive bacterium or a recombinant nucleic acid as described herein wherein said one or more endogenous genes and said one or more exogenous genes are transcriptionally or translationally coupled by means of an intergenic region. In yet another embodiment, the invention relates to a gram-positive bacterium or a recombinant nucleic acid, comprising a polycistronic expression unit as described herein, wherein any 5' gene is coupled to a 3' gene by a polynucleic acid sequence comprising or consisting of an intergenic region. In a preferred embodiment, said intergenic region is endogenous to a gram-positive bacterium. In a further preferred embodiment, said intergenic region is an operon intergenic region.

As used herein, the term "intergenic region" is synonymous with "intergenic linker" or "intergenic spacer". An intergenic region is defined as a polynucleic acid sequence between adjacent (i.e., located on the same polynucleic acid sequence) genes, open reading frames, cistrons or coding sequences. By extension, the intergenic region can include the stop codon of the 5' gene and/or the start codon of the 3' gene which are linked by said intergenic region. As defined herein, the term intergenic region specifically relates to intergenic regions between adjacent genes in a polycistronic expression unit. For example, an intergenic region as defined herein can be found between adjacent genes in an operon. Accordingly, in an embodiment, the intergenic region as defined herein is an operon intergenic region.

In an embodiment, the intergenic region, linker or spacer is selected from the group of intergenic regions comprising or consisting of intergenic regions preceding, i.e. 5' to, or more particularly immediately 5' to, rplW, rplP, rpmD, rplB, rpsG, rpsE or rplN of a gram-positive bacterium. In an embodiment, said gram positive bacterium is a lactic acid bacterium, preferably a *Lactococcus* species, more preferably *Lactococcus lactis*, and any subspecies or strain thereof. In an embodiment, said intergenic region encompasses the start codon of rplW, rplP, rpmD, rplB, rpsG, rpsE or rplN and/or the stop codon of the preceding, i.e. 5', gene. In a preferred embodiment, the invention relates to a gram-positive bacterium or a recombinant nucleic acid as described herein, wherein the endogenous gene and the one or more exogenous genes are transcriptionally coupled by intergenic region or regions active in the gram-positive bacterium, preferably wherein the intergenic region or regions is endogenous to said gram-positive bacterium, more preferably wherein the endogenous intergenic region is selected from the group consisting of intergenic regions preceding rplW, rplP, rpmD, rplB, rpsG, rpsE, rplN, rplM, rplE, and rplF.

The skilled person will appreciate that if the intergenic region encompasses a 5' stop codon and/or a 3' start codon, these respective codons preferably are not present in the genes which are linked by said intergenic regions, in order to avoid double start and/or stop codons, which may affect correct translation initiation and/or termination. Methods for identifying intergenic regions are known in the art. By means of further guidance, intergenic regions can for instance be identified based on prediction of operons, and associated promoters and open reading frames, for which ample software is known and available in the art.

In a further embodiment, said intergenic region sequence is selected from the group comprising, consisting essentially of or consisting of any of SEQ ID NOs: 1 to 7:

```
                                    SEQ ID NO: 1
    TAATG

SEQ ID NO: 2
    TAATCCATG

SEQ ID NO: 3
    TAAGGAGGAAAAAATG

SEQ ID NO: 4
    TAATAGAGGAGGAAAATCGTG

SEQ ID NO: 5
    TAAGAAGGGAGATAAGTAAGAATG

SEQ ID NO: 6
    TAAGGAAAGGGGTAATTAAACATG

SEQ ID NO: 7
    TAAGCAAAACTAGGAGGAATATAGCATG.
```

In a further embodiment, said intergenic region sequence is selected from the group comprising, consisting essentially of or consisting of sequences displaying one mismatch or a deletion or insertion of one nucleotide vs. SEQ ID NO: 1 or SEQ ID NO: 2, sequences displaying one, two or three mismatches, or a deletion or insertion of one, two or three nucleotides vs. SEQ ID NO: 3 or SEQ ID NO: 4, and sequences displaying one, two, three or four mismatches or a deletion or insertion of one, two, three or four nucleotides vs. SEQ ID NO: 5, SEQ ID NO: 6 or SEQ ID NO: 7.

SEQ ID NOs: 1 to 7 all comprise a 5' stop codon and a 3' start codon. SEQ ID NOs: 1 to 7 correspond to the intergenic regions preceding, respectively, rplW, rplP, rpmD, rplB, rpsG, rpsE and rplN of *Lactococcus lactis* ssp. *cremoris* strain MG1363 (Genbank accession number AM406671.1). These sequences are among other identical to the corresponding sequences of *Lactococcus lactis* ssp. *lactis* strain CV56 (Genbank accession number CP002365.1), *Lactococcus lactis* ssp. *cremoris* strain NZ9000 (Genbank accession number CP002094.1), *Lactococcus lactis* ssp. *lactis* strain KF147 (Genbank accession number CP001834.1), *Lactococcus lactis* ssp. *lactis* strain IL1403 (Genbank accession number AE005176.1), and *Lactococcus lactis* ssp. *cremoris* strain SK11 (Genbank accession number CP000425.1).

In another embodiment, the intergenic region, linker or spacer is selected from the group of intergenic regions comprising or consisting of intergenic regions preceding, i.e. 5' to, more particularly immediately 5' to, rplP, rpmD, rplM, rpsE, rplE, or rplF of a gram-positive bacterium. In an embodiment, said gram positive bacterium is a lactic acid bacterium, preferably an *Enterococcus* species, more preferably *Enterococcus faecium*, and any subspecies or strain thereof. In an embodiment, said intergenic region encompasses the start codon of rplP, rpmD, rplM, rpsE, rplE, or rplF and/or the stop codon of the preceding, i.e. 5', gene. The skilled person will appreciate that if the intergenic region encompasses a 5' stop codon and/or a 3' start codon, these respective codons preferably are not present in the genes which are linked by said intergenic regions, in order to avoid double start and/or stop codons, which may affect correct translation initiation and/or termination. Methods for identifying intergenic regions are known in the art. By means of further guidance, intergenic regions can for instance be identified based on prediction of operons, and associated promoters and open reading frames, for which ample software is known and available in the art.

In a further embodiment, said intergenic region sequence is selected from the group comprising, consisting essentially of or consisting of any of SEQ ID NOs: 8 to 13:

TAATC SEQ ID NO: 8

TAAGGAGGACAACAATA SEQ ID NO: 9

TAATAGGAGGGAATTTCA SEQ ID NO: 10

TTAGAAGAAGGAGGAATACCATTC SEQ ID NO: 11

TAAAAGTTTAAGGAAGGAGGGTCTTACTGA SEQ ID NO: 12

TAATCAAGTAGAATCTACAAGGAGGTGTCTTTAA SEQ ID NO: 13

In a further embodiment, said intergenic region sequence is selected from the group comprising, consisting essentially of or consisting of sequences displaying one mismatch or a deletion or insertion of one nucleotide vs. SEQ ID NO: 8, sequences displaying one, two or three mismatches, or a deletion or insertion of one, two or three nucleotides vs. SEQ ID NO: 9 or SEQ ID NO: 10 and sequences displaying one, two, three or four mismatches or a deletion or insertion of one, two, three or four nucleotides vs. SEQ ID NO: 11, SEQ ID NO: 12 or SEQ ID NO: 13. SEQ ID NOs: 8 to 13 correspond to the intergenic regions preceding, respectively, rplP, rpmD, rplM, rpsE, rplE, and rplF of *Enterococcus faecium* strain LMG15709.

In an embodiment, the intergenic regions as described herein, excluding any preceding stop codon and excluding any subsequent start codon may comprise or consist of more than 1 nucleotide, such as 2, 3, 4, 5, 6, 7, 8, 9, 10, 11, 12, 13, 14, 15, 16, 17, 18, 19, 20, 21, 22, 23, 24, 25 or more nucleotides, preferably more than 5 nucleotides, even more preferably 10 or more nucleotides. In another embodiment, the intergenic region may comprise 1 to 50 nucleotides, such as 1 to 40, 1 to 30, 1 to 25, 1 to 20, 1 to 15, or 1 to 10, preferably 5 to 50, 5 to 40, 5 to 30, 5 to 25, 5 to 20, 5 to 15, or 5 to 10 nucleotides, even more preferably 10 to 50, 10 to 40, 10 to 30, 10 to 25, 10 to 20, or 10 to 15 nucleotides.

Particularly preferred embodiments of gram-positive bacteria comprising a polycistronic expression unit as described herein are depicted in Tables 1 and 2, wherein said gram-positive bacterium comprises an endogenous promoter, 3' of which the endogenous gene coupled to the intergenic region as depicted in Tables 1 and 2, 3' of which one or more exogenous genes, open reading frame or coding sequence coupled to the intergenic region. In a preferred embodiment, each gene depicted in Tables 1 and 2 is transcriptionally controlled by its native promoter, and optionally regulatory sequences. In another preferred embodiment, said polycistronic expression unit is integrated in the bacterial chromosome. In a further preferred embodiment, said endogenous promoter and/or endogenous gene are present at their native locus on the bacterial genome or chromosome. Preferably, the start and stop codons, if present, replace the start and stop codons of said exogenous gene and said endogenous gene, respectively.

TABLE 1

Exemplary polycistronic expression unit may comprise or consist essentially of endogenous promoter >> endogenous gene >> intergenic region >> exogenous gene, wherein the endogenous gene and intergenic region are selected from the combinations below.

| endogenous gene | intergenic region |
| --- | --- |
| eno | rplW |
| eno | rplP |
| eno | rpmD |
| eno | rplB |
| eno | rpsG |
| eno | rpsE |
| eno | rplN |
| eno | rplM |
| eno | rplE |
| eno | rplF |
| usp45 | rplW |
| usp45 | rplP |
| usp45 | rpmD |
| usp45 | rplB |
| usp45 | rpsG |
| usp45 | rpsE |
| usp45 | rplN |
| usp45 | rplM |
| usp45 | rplE |
| usp45 | rplF |
| gap | rplW |
| gap | rplP |
| gap | rpmD |
| gap | rplB |
| gap | rpsG |
| gap | rpsE |
| gap | rplN |
| gap | rplM |
| gap | rplE |
| gap | rplF |
| pyk | rplW |
| pyk | rplP |
| pyk | rpmD |
| pyk | rplB |
| pyk | rpsG |
| pyk | rpsE |
| pyk | rplN |
| pyk | rplM |
| pyk | rplE |

TABLE 1-continued

Exemplary polycistronic expression unit may comprise or consist essentially of endogenous promoter >> endogenous gene >> intergenic region >> exogenous gene, wherein the endogenous gene and intergenic region are selected from the combinations below.

| endogenous gene | intergenic region |
|---|---|
| pyk | rplF |
| rpmB | rplW |
| rpmB | rplP |
| rpmB | rpmD |
| rpmB | rplB |
| rpmB | rpsG |
| rpmB | rpsE |
| rpmB | rplN |
| rpmB | rplM |
| rpmB | rplE |
| rpmB | rplF |
| rplS | rplW |
| rplS | rplP |
| rplS | rpmD |
| rplS | rplB |
| rplS | rpsG |
| rplS | rpsE |
| rplS | rplN |
| rplS | rplM |
| rplS | rplE |
| rplS | rplF |

Preferably, intergenic regions rplW, rplB, rpsG, and rplN originate from a *Lactococcus* species, subspecies or strain, preferably *Lactococcus lactis*. Preferably, intergenic regions rplP, rplM, and rplE originate from an *Enterococcus* species, subspecies or strain, preferably *Enterococcus faecalis* or *Enterococcus Faecium*. Preferably, intergenic regions rplP, rpmD, and rpsE originate from a *Lactococcus* species, subspecies or strain, preferably *Lactococcus lactis* or from an *Enterococcus* species, subspecies or strain, preferably *Enterococcus faecalis* or *Enterococcus Faecium*.

For example but without limitation, where the polycistronic expression unit comprises two exogenous genes, the structure represented as endogenous promoter>>endogenous gene>>intergenic region>> exogenous gene>>intergenic region>>exogenous gene may be as follows: usp45>>usp45>>rpmD>>exogenous gene 1>>rplN>>exogenous gene 2; enoA>>enoA>>rpmD>> exogenous gene 1>>rplN>>exogenous gene 2; gapB>>gapB>>rpmD>>exogenous gene 1>>rplN>>exogenous gene 2. For example, such arrangement may be particularly suited for the expression of heavy and light chains of antibodies (preferably in that order), such as anti-TNFα antibodies as taught herein.

TABLE 2

Exemplary polycistronic expression unit may comprise or consist essentially of endogenous promoter >> endogenous gene >> intergenic region >> exogenous gene, wherein the endogenous gene and intergenic region are selected from the combinations below.

| endogenous gene | intergenic region |
|---|---|
| eno | SEQ ID NO: 1 |
| eno | SEQ ID NO: 2 |
| eno | SEQ ID NO: 3 |
| eno | SEQ ID NO: 4 |
| eno | SEQ ID NO: 5 |
| eno | SEQ ID NO: 6 |
| eno | SEQ ID NO: 7 |
| eno | SEQ ID NO: 8 |
| eno | SEQ ID NO: 9 |
| eno | SEQ ID NO: 10 |
| eno | SEQ ID NO: 11 |
| eno | SEQ ID NO: 12 |
| eno | SEQ ID NO: 13 |
| usp45 | SEQ ID NO: 1 |
| usp45 | SEQ ID NO: 2 |
| usp45 | SEQ ID NO: 3 |
| usp45 | SEQ ID NO: 4 |
| usp45 | SEQ ID NO: 5 |
| usp45 | SEQ ID NO: 6 |
| usp45 | SEQ ID NO: 7 |
| usp45 | SEQ ID NO: 8 |
| usp45 | SEQ ID NO: 9 |
| usp45 | SEQ ID NO: 10 |
| usp45 | SEQ ID NO: 11 |
| usp45 | SEQ ID NO: 12 |
| usp45 | SEQ ID NO: 13 |
| gap | SEQ ID NO: 1 |
| gap | SEQ ID NO: 2 |
| gap | SEQ ID NO: 3 |
| gap | SEQ ID NO: 4 |
| gap | SEQ ID NO: 5 |
| gap | SEQ ID NO: 6 |
| gap | SEQ ID NO: 7 |
| gap | SEQ ID NO: 8 |
| gap | SEQ ID NO: 9 |
| gap | SEQ ID NO: 10 |
| gap | SEQ ID NO: 11 |
| gap | SEQ ID NO: 12 |
| gap | SEQ ID NO: 13 |
| pyk | SEQ ID NO: 1 |
| pyk | SEQ ID NO: 2 |
| pyk | SEQ ID NO: 3 |
| pyk | SEQ ID NO: 4 |
| pyk | SEQ ID NO: 5 |
| pyk | SEQ ID NO: 6 |
| pyk | SEQ ID NO: 7 |
| pyk | SEQ ID NO: 8 |
| pyk | SEQ ID NO: 9 |
| pyk | SEQ ID NO: 10 |
| pyk | SEQ ID NO: 11 |
| pyk | SEQ ID NO: 12 |
| pyk | SEQ ID NO: 13 |
| rpmB | SEQ ID NO: 1 |
| rpmB | SEQ ID NO: 2 |
| rpmB | SEQ ID NO: 3 |
| rpmB | SEQ ID NO: 4 |
| rpmB | SEQ ID NO: 5 |
| rpmB | SEQ ID NO: 6 |
| rpmB | SEQ ID NO: 7 |
| rpmB | SEQ ID NO: 8 |
| rpmB | SEQ ID NO: 9 |
| rpmB | SEQ ID NO: 10 |
| rpmB | SEQ ID NO: 11 |
| rpmB | SEQ ID NO: 12 |
| rpmB | SEQ ID NO: 13 |
| rplS | SEQ ID NO: 1 |
| rplS | SEQ ID NO: 2 |
| rplS | SEQ ID NO: 3 |
| rplS | SEQ ID NO: 4 |
| rplS | SEQ ID NO: 5 |
| rplS | SEQ ID NO: 6 |
| rplS | SEQ ID NO: 7 |
| rplS | SEQ ID NO: 8 |
| rplS | SEQ ID NO: 9 |
| rplS | SEQ ID NO: 10 |
| rplS | SEQ ID NO: 11 |
| rplS | SEQ ID NO: 12 |
| rplS | SEQ ID NO: 13 |

Preferably, the gram-positive bacterium having a polycistronic expression unit comprising any of SEQ ID NOs: 1 to 7 is a *Lactococcus* species, subspecies or strain, preferably *Lactococcus lactis*. Preferably, the gram-positive bacterium having a polycistronic expression unit comprising any of SEQ ID NOs: 8 to 13 is an *Enterococcus* species, subspecies or strain, preferably *Enterococcus faecalis* or *Enterococcus Faecium*.

The skilled person will appreciate that the exogenous genes, open reading frames or coding sequences according to the invention can be coupled to additional sequences, which additional sequences effect a particular purpose. For instance, in order to increase secretion of the exogenous gene, the gene may be coupled to a nucleic acid sequence encoding a secretion signal peptide. In a particularly preferred embodiment, the exogenous gene, open reading frame or coding sequence according to the invention is coupled at its 5' end to the polynucleic acid sequence encoding the Usp45 secretion signal, preferably originating from a *Lactococcus* species, more preferably *Lactococcus lactis* and subspecies and strains thereof.

Typically, a secretion signal sequence represents an about 16 to about 35 amino acid segment, usually containing hydrophobic amino acids that become embedded in the lipid bilayer membrane, and thereby allow for the secretion of an accompanying protein or peptide sequence from the host cell, and which usually is cleaved from that protein or peptide. Preferably, the secretion signal sequence may be so-active in a host cell intended for use with the nucleic acid comprising the said signal sequence.

Secretion signal sequences active in suitable host cells are known in the art; exemplary *Lactococcus* signal sequences include those of usp45 (see, U.S. Pat. No. 5,559,007) and others, see, e.g., Perez-Martinez et al. *Mol. Gen. Genet.*, 1992, vol. 234, 401-11; Sibakov et al., *Appl. Environ. Microbiol.*, 1991, vol. 57(2), 341-8. Preferably, the signal sequence is located between the promoter sequence and the ORF, i.e. the signal sequence is located 3' from the promoter sequence and precedes the ORF of the polypeptide of interest. In a preferred embodiment, the signal sequence encodes the amino acid sequence MKKKIISAILMSTVIL-SAAAPLSGVYA (usp45). Alternatively, a mutated usp45 signal sequence (usp45N) may be used which results in further controllable production and secretion of the polypeptide of interest. In particular, the mutant comprises an asparagine (N) at position 4 instead of a lysine (K), or a K4N mutation. In a preferred embodiment, the signal sequence encodes the amino acid sequence MKKNIISAILMSTVIL-SAAAPLSGVYADTN.

The invention also relates to a polynucleic acid sequence comprising a polycistronic expression unit according to the invention as described herein. In particular, in an aspect, the invention relates to a polynucleic acid sequence comprising a polycistronic expression unit according to the invention as described herein, wherein said polycistronic unit comprises one or more gene endogenous to a gram-positive bacterium and one or more gene, open reading frame or coding sequence exogenous to a gram-positive bacterium, wherein the one or more endogenous genes and the one or more exogenous genes are translationally or transcriptionally coupled in a way as described herein. Preferably the one or more endogenous genes is coupled to the 5' end of the one or more exogenous genes. Preferably, the one or more endogenous genes and the one or more exogenous genes are connected by an intergenic region as described herein, preferably an intergenic region preceding rplW, rplP, rpmD, rplB, rpsG, rpsE, and rplN as described herein elsewhere or an intergenic region corresponding to any of SEQ ID NOs: 1 to 7 or an intergenic region preceding rplP, rpmD, rplM, rpsE, rplE, or rplF as described herein elsewhere or an intergenic region corresponding to any of SEQ ID NOs: 8 to 13 or related sequences as described above. In an embodiment, the polynucleic acid sequence further comprises a promoter, preferably a promoter endogenous of a gram-positive bacterium. In another embodiment, the polynucleic acid sequence further comprises regulatory sequences, e.g. operator, terminator and the like. In a preferred embodiment, the promoter is the native promoter of the endogenous gene.

In a further aspect, the invention relates to a replicon comprising the polynucleic acid sequence as described herein. Preferably, said replicon is a vector, as described herein elsewhere. In an embodiment, said vector is suitable for prokaryotic expression. In another embodiment, said vector is suitable for homologous recombination in a gram-positive bacterium.

In another aspect, the invention relates to a polynucleic acid sequence comprising a ribosome binding site of a gram positive bacterium and a gene, open reading frame or coding sequence exogenous to said bacterium, wherein the ribosome binding site is configured to effect translation of the exogenous gene, open reading frame or coding sequence. In an embodiment, the polynucleic acid sequence comprises a ribosome binding site of a gram positive bacterium and a gene, open reading frame or coding sequence exogenous to said bacterium, wherein the ribosome binding site is connected at the 5' end of the exogenous gene, open reading frame or coding sequence.

In another aspect, the invention relates to a polynucleic acid sequence comprising an intergenic region, preferably an operon intergenic region, of a gram positive bacterium and a gene, open reading frame or coding sequence exogenous to said bacterium, wherein the intergenic region is configured to effect translation of the exogenous gene, open reading frame or coding sequence. In an embodiment, the polynucleic acid sequence comprises an intergenic region, preferably an operon intergenic region, of a gram positive bacterium and a gene, open reading frame or coding sequence exogenous to said bacterium, wherein the intergenic region is connected at the 5' end of the exogenous gene, open reading frame or coding sequence. Preferably, the intergenic region is an intergenic region preceding rplW, rplP, rpmD, rplB, rpsG, rpsE, or rplN as described herein elsewhere or an intergenic region corresponding to any of SEQ ID NOs: 1 to 7 or an intergenic region preceding rplP, rpmD, rplM, rpsE, rplE, or rplF as described herein elsewhere or an intergenic region corresponding to any of SEQ ID NOs: 8 to 13 or related sequences as described above.

In a further aspect, the invention relates to a polycistronic expression vector comprising the intergenic region preceding rplW, rplP, rpmD, rplB, rpsG, rpsE, or rplN as described herein elsewhere or an intergenic region corresponding to any of SEQ ID NOs: 1 to 7 or an intergenic region preceding rplP, rpmD, rplM, rpsE, rplE, or rplF as described herein elsewhere or an intergenic region corresponding to any of SEQ ID NOs: 8 to 13 or related sequences as described above. In an embodiment, said vector is suitable for cloning a gene, open reading frame or coding sequence at the 3' end of said intergenic region, preferably a gene which is exogenous to a gram-positive bacterium. In an embodiment, said vector is suitable for being replicated in a gram-positive bacterium. In a further embodiment, said vector is suitable for effecting homologous recombination in a gram-positive bacterium, in particular for chromosomal integration of said intergenic region and a gene, open reading frame or coding sequence at the 3' end of said intergenic region. In an embodiment, said vector further comprises one or more promoter, preferably a gram-positive bacterial promoter. In a further embodiment, said vector further comprises regulatory sequences, e.g. operator, terminator and the like. In yet another embodiment, said vector further comprises one or more selection markers, such as antibiotic resistance genes.

In another aspect, the invention relates to a method for exogenous gene expression in a gram-positive bacterium, comprising the step of transforming said gram-positive bacterium with the vector comprising an exogenous gene, open reading frame or coding sequence, optionally further comprising an (endogenous) promoter as described herein.

In a further aspect, the invention relates to the use of a polynucleic acid sequence comprising an intergenic region of a gram-positive bacterium as described herein for polycistronic expression of one or more gene, open reading frame or coding sequence exogenous to said gram-positive bacterium. In an embodiment, the invention relates to the use of a polynucleic acid sequence comprising an intergenic region of a gram-positive bacterium as described herein for polycistronic expression of one or more genes, open reading frames or coding sequences exogenous to said gram-positive bacterium and one or more gene, open reading frame or coding sequences endogenous to said gram-positive bacterium. In an embodiment, said one or more genes exogenous to said gram-positive bacterium is coupled to the 3' end of said endogenous gene. Preferably, the intergenic region is an intergenic region preceding rplW, rplP, rpmD, rplB, rpsG, rpsE or rplN as described herein elsewhere or an intergenic region corresponding to any of SEQ ID NOs: 1 to 7 or an intergenic region preceding rplP, rpmD, rplM, rpsE, rplE, or rplF as described herein elsewhere or an intergenic region corresponding to any of SEQ ID NOs: 8 to 13 or related sequences as described above.

In another aspect, the invention relates to a method for expressing of one or more exogenous protein in a gram-positive bacterium, comprising the step of introducing a polynucleic acid sequence encoding said one or more exogenous protein or a vector as described herein in said gram-positive bacterium such as to be transcribed in a polycistronic mRNA.

In yet another aspect, the invention relates to a method for generating a gram-positive bacterium capable of expressing one or more exogenous proteins, comprising the step of introducing a polynucleic acid sequence encoding one or more exogenous protein or a vector as described herein in said gram-positive bacterium such as to be transcribed in a polycistronic mRNA.

According to the invention, the one or more exogenous genes, open reading frame of coding sequence can be of any kind or origin. In an embodiment, the one or more exogenous genes encodes a protein, polypeptide and/or peptide, preferably a protein, polypeptide and/or peptide having a therapeutic or preventive effect in a subject, or preferably an antigen such as an antigen for inducing immunity or immunotolerance, a non-vaccinogenic therapeutically active polypeptide, an antibody or a functional fragment thereof such as Fab, a fusion protein or a multimeric protein. In a preferred embodiment, the one or more exogenous genes encodes an antibody or a functional antibody fragment. As used herein, the term "functional" refers to an antibody fragment, which can still exert its intended function, i.e. antigen binding. The term antibody, as used here, includes, but is not limited to conventional antibodies, chimeric antibodies, dAb, bispecific antibody, trispecific antibody, multispecific antibody, bivalent antibody, trivalent antibody, multivalent antibody, VHH, nanobody, Fab, Fab', F(ab')$_2$ scFv, Fv, dAb, Fd, diabody, triabody, single chain antibody, single domain antibody, single antibody variable domain.

In the present context, the term "antibody" is used to describe an immunoglobulin whether natural or partly or wholly engineered. As antibodies can be modified in a number of ways, the term "antibody" should be construed as covering any specific binding molecule or substance having a binding domain with the required binding specificity for the other member of the pair of molecules, i.e. the target molecule, as defined supra. Thus, this term covers antibody fragments, derivatives, functional equivalents and homologues of antibodies, as well as single chain antibodies, bifunctional antibodies, bivalent antibodies, VHH, nanobodies, Fab, Fab', F(ab')$_2$, scFv, Fv, dAb, Fd, diabodies, triabodies and camelid antibodies, including any polypeptide comprising an immunoglobulin binding domain, whether natural or wholly or partially engineered. Chimeric molecules comprising an immunoglobulin binding domain, or equivalent, fused to another polypeptide are therefore included. The term also covers any polypeptide or protein having a binding domain which is, or is homologous to, an antibody binding domain, e.g. antibody mimics. Examples of antibodies are the immunoglobulin isotypes and their isotypic subclasses, including IgG (IgG1, IgG2a, IgG2b, IgG3, IgG4), IgA, IgD, IgM and IgE. The person in the art will thus appreciate that the present invention also relates to antibody fragments, comprising an antigen binding domain such as VHH, nanobodies Fab, scFv, Fv, dAb, Fd, diabodies and triabodies. In an embodiment, the invention relates to a gram-positive bacterium or a recombinant nucleic acid as described herein, wherein one exogenous gene encodes the light chain ($V_L$) of an antibody or of a functional fragment thereof, and another exogenous gene encodes the heavy chain ($V_H$) of the antibody or of a functional fragment thereof, more preferably wherein the functional fragment is Fab. In an embodiment, the exogenous gene encoding $V_L$ or functional fragment thereof is transcriptionally coupled to the 3' end of the exogenous gene encoding $V_H$ or functional fragment thereof.

In an embodiment, the antibody as described herein at least partially or fully blocks, inhibits, or neutralises a biological activity of a target molecule, such as a cytokine or chemokine. As used herein, the expression "neutralises" or "neutralisation" means the inhibition of or reduction in a biological activity of a cytokine as measured in vivo or in vitro, by methods known in the art, such as, for instance, as detailed in the examples. In particular, the inhibition or reduction may be measured by determining the colitic score or by determining the target molecule in a tissue or blood sample. As used herein, the expression "neutralises" or "neutralisation" means the inhibition of or reduction in a biological activity of a cytokine as measured in vivo or in vitro, by at least 10% or more, preferably by at least 20%, 30%, 40%, 50%, 60%, 70%, 80%, 90% and even more preferably by 100%.

Preferably, said binding molecules are binding to and inhibiting the biological effect of cytokines chosen from the list of IL-1β, IL-2, IL-4, IL-5, IL-6, IL-7, IL-8, IL-9, IL-12 (or its subunits IL-12p35 and IL12p40), IL-13, IL-15, IL-16, IL-17, IL-18, IL-21, IL-23 (or its subunit IL-23p19), IL-27, IL-32 (and its splice variants), IFN (α, β, γ) and TNFα. Preferably, said binding molecules are soluble cytokine receptors such as gp130, or are binding to the receptors of said cytokines, for example IL-2R (CD25, CD122, CD132), IL-12R (beta1, beta2), IL15R, IL-17R, IL-23R or IL-6R, without triggering an inflammatory signal. Preferably, said binding molecules are neutralizing chemokines chosen from the list of MIF, MIP-1α, MCP-1, RANTES and Eotaxin. Preferably, said binding molecules are solving the blockade of immune activation via binding to costimulatory molecules from the list of CD3/CD28, HVEM, B7.1/67.2, CD40/CD40 L(CD154), ICOS/ICOSL, OX40/X40L, CD27/ CD27L(CD70), CD30/CD30L(CD153) and 41BB/41BBL. Preferably, said binding molecules are solving the blockade of inflammation via binding to adhesion molecules from the list I-CAM1, α4 integrin and α4β7 integrin. Preferably, said binding molecules have a costimulatory and agonistic effect on CD3, CTLA4 and/or PD1. Preferably, said binding molecules are neutralizing T-cells or B-cell activity by targeting CD25, CD20, CD52, CD95, BAFF, APRIL and/or IgE. Preferably, said binding molecules are solving the blockade of inflammation via binding to enzymes from the MMP family. Preferably, said binding molecules assert an anti-angiogenic effect, such as neutralizing αvβ3/α5β1 and IL-8 activity. In a further preferred embodiment said binding molecule is capable of neutralizing the biological effect of TNFα, IL-12, IFNγ, IL-23 or IL-17. Preferably, said binding molecule is chosen from the group consisting of an anti-TNFα antibody, anti-TNFα antibody fragment, anti-TNFα single antibody variable domain, soluble TNF receptor or dominant negative variant of TNFα;

anti-IL-12 antibody, anti-IL-12 antibody fragment, anti-IL-12 single antibody variable domain, soluble IL-12 receptor, dominant negative variant of IL-12 or IL-12 dAb;

anti-IL-12p35 antibody, anti-IL-12p35 antibody fragment, anti-IL-12p35 single antibody variable domain, soluble IL-12p35 receptor, dominant negative variant of IL-12p35 or IL-12p35 dAb;

anti-IL-12p40 antibody, anti-IL-12p40 antibody fragment, anti-IL-12p40 single antibody variable domain, soluble IL-12p40 receptor, dominant negative variant of IL-12p40 or IL-12p40 dAb;

anti-IL-23 antibody, anti-IL-23 antibody fragment, anti-IL-23 single antibody variable domain, soluble IL-23 receptor, dominant negative variant of IL-23 or IL-23 dAb;

anti-IL-23p19 antibody, anti-IL-23p19 antibody fragment, anti-IL-23p19 single antibody variable domain, soluble IL-23p19 receptor, dominant negative variant of IL-23p19 or IL-23p19 dAb;

an anti-IFNγ antibody, anti-IFNγ antibody fragment, anti-IFNγ single antibody variable domain, soluble IFNγ receptor or dominant negative variant of IFNγ;

anti-IL-17 antibody, anti-IL-17 antibody fragment, anti-IL-17 single antibody variable domain, soluble IL-17 receptor, dominant negative variant of IL-17 or IL-17 dAb; and anti-MCP-1 antibody, anti-MCP-1 antibody fragment, anti-MCP-1 single antibody variable domain, soluble IL-17 receptor, dominant negative variant of MCP-1 or MCP-1 dAb.

In a preferred embodiment, said antibody is a Fab fragment (fragment antigen-binding). Fab fragments are well known in the art. By means of further guidance, a Fab fragment is a region on an antibody that binds to antigens. It is composed of one constant and one variable domain of each of the heavy and the light chain.

In an embodiment, the Fab is cA2 anti-TNF Fab (of which the polynucleotide and polypeptide sequences of the variable domain of the heavy chain and the light chain are disclosed in U.S. Pat. No. 6,790,444 as SEQ ID NO: 4 and 5 (heavy chain) and SEQ ID NO: 2 and 3 (light chain), respectively) or CDP870 anti-TNF Fab (of which the polynucleotide and polypeptide sequences of the heavy chain and the light chain are disclosed in WO 01/94585 as SEQ ID NO: 114 and 115 (heavy chain) and SEQ ID NO: 112 and 113 (light chain), respectively).

The skilled person will appreciate that antibodies, as are functional antibody fragments, and in particular Fab fragments, are composed of different individual polypeptides which may be covalently linked by disulphide bridges. In particular, the heavy chain and the light chain are encoded by separate individual coding sequences.

Accordingly, the coding regions of the heavy and light chains may each be comprised in a polycistronic expression unit as described herein. Polynucleic acid sequences encoding heavy and light chains may be incorporated in different polycistronic expression units. Preferably, polynucleic acid sequences encoding heavy and light chains are incorporated in the same polycistronic expression unit. Accordingly, in an embodiment, the invention relates to a gram-positive bacterium as described herein, comprising one or more endogenous genes, one or more polynucleic acid sequence encoding an antibody heavy chain, or a fragment, preferably a functional fragment thereof, and one or more polynucleic acid sequence encoding an antibody light chain, or a fragment, preferably a functional fragment thereof, which are translationally or transcriptionally coupled. In another embodiment, the invention relates to a gram-positive bacterium comprising a polycistronic expression unit, wherein said polycistronic expression unit comprises one or more endogenous genes, one or more polynucleic acid sequence encoding an antibody heavy chain, or a fragment, preferably a functional fragment thereof, and one or more polynucleic acid sequence encoding an antibody light chain, or a fragment, preferably a functional fragment thereof. In yet another embodiment, the polynucleic acid sequence encoding a light chain is transcriptionally or translationally coupled to 3' end of the polynucleic acid sequence encoding the heavy chain. Advantageously, such coupling further increases the expression of both heavy and light chain.

The invention also relates to the use of the gram-positive bacteria according to the invention as described herein for therapy. The invention further relates to a pharmaceutical composition comprising the gram-positive bacterium according to the invention as described herein.

Accordingly, in an aspect, the invention relates to the gram-positive bacterium or a pharmaceutical composition comprising the gram-positive bacterium according to the invention as described herein for use as a medicament. In another aspect, the invention relates to the gram-positive bacterium or a pharmaceutical composition comprising the gram-positive bacterium according to the invention as described herein for use in therapy or treatment. In a further aspect, the invention relates to the use of the gram-positive bacterium or a pharmaceutical composition comprising the gram-positive bacterium according to the invention as described herein for the manufacture of a medicament. In yet another aspect, the invention relates to a method of treatment, comprising administering the gram-positive bacterium or a pharmaceutical composition comprising the gram-positive bacterium according to the invention as described herein. In an embodiment, the invention relates to a gram-positive bacterium or a pharmaceutical composition comprising a gram-positive bacterium as described herein, wherein the one or more exogenous genes encodes a product, such as a protein, polypeptide or peptide, which product has a therapeutic or preventive effect in a subject, preferably for use as a medicament, preferably for use in administration or delivery of said product to the subject.

In a related aspect, the invention provides a method for delivery of a polypeptide encoded by the one or more exogenous genes, open reading frame, or coding sequence comprised in the gram-positive bacterium of the invention to human or animal in need thereof, comprising administering to said human or animal a therapeutically effective amount of gram-positive bacteria according to the invention as described herein. The animal may preferably be a mammal, such as, e.g., domestic animals, farm animals, zoo animals, sport animals, pet and experimental animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on.

As used herein, the terms "treat" or "treatment" refer to both therapeutic treatment and prophylactic or preventative measures, wherein the object is to prevent or slow down (lessen) an undesired physiological change or disorder. A "human or animal in need of treatment" includes ones that would benefit from treatment of a given condition.

The term "therapeutically effective amount" refers to an amount of a therapeutic substance or composition effective to treat a disease or disorder in a subject, e.g., human or animal, i.e., to obtain a desired local or systemic effect and performance. By means of example, a therapeutically effective amount of bacteria may comprise at least 1 bacterium, or at least 10 bacteria, or at least $10^2$ bacteria, or at least $10^3$ bacteria, or at least $10^4$ bacteria, or at least $10^5$ bacteria, or at least $10^6$ bacteria, or at least $10^7$ bacteria, or at least $10^8$ bacteria, or at least $10^9$, or at least $10^{10}$, or at least $10^{11}$, or at least $10^{12}$, or at least $10^{13}$, or at least $10^{14}$, or at least $10^{15}$, or more gram-positive bacteria, e.g., in a single or repeated dose.

The gram-positive bacteria of the present invention may be administered alone or in combination with one or more active compounds. The latter can be administered before, after or simultaneously with the administration of the gram-positive bacteria.

A number of prior art disclosures on the delivery of antigens and/or therapeutically active polypeptides exist, and it shall be appreciated that such disclosures may be further advantageously modified with the gram-positive bacteria of the present invention. By means of example and not limitation, bacterial delivery of interleukins in particular IL-10 for treating colitis (e.g. WO 00/23471), IL-27 for modulating an inflammatory response (WO 2004/069177), delivery of antigens as vaccines (e.g. WO 97/14806), delivery of GLP-2 and related analogs may be used to treat short bowel disease, Crohn's disease, osteoporosis and as adjuvant therapy during cancer chemotherapy, etc. Furthermore, bacterial delivery of trefoil peptides may be used to treat diseases of the alimentary canal (e.g. WO 01/02570). In particular, the use of trefoil proteins or peptides for treatment of disorders of and damage to the alimentary canal, including the mouth, oesophagus, stomach, and large and small intestine, as well as for the protection and treatment of tissues that lie outside the alimentary canal are described in WO 97/38712 and WO 92/14837. These proteins can be used either to treat lesions in these areas or to inhibit the formation of lesions. These lesions can be caused by: radiation therapy or chemotherapy for the treatment of cancer, any other drug including alcohol which damages the alimentary canal, accidental exposure to radiation or to a caustic substance, infection, a digestive disorder including but not limited to oral mucositis, intestinal mucositis, esophagitis, proctitis, non-ulcer dyspepsia, gastritis, peptic or duodenal ulcer, gastric cancer, colon cancer, MALT lymphoma, Menetier's syndrome, gastro-oesophageal reflux disease, Crohn's disease, ulcerative colitis and acute colitis of chemical, bacterial or obscure origin. Trefoil peptides are particularly useful to treat acute colitis, oral mucositis, intestinal mucositis, esophagitis, proctitis. Further therapeutic applications are envisioned using the promoters and host cells of the invention.

Further non-limiting examples of the types of diseases treatable in humans or animals by delivery of therapeutic polypeptides according to the invention include, but are not limited to, e.g., inflammatory bowel diseases including Crohn's disease and ulcerative colitis (treatable with, e.g., IL-Ira, IL-10, IL-27 or trefoil peptides); autoimmune diseases, including but not limited to psoriasis, rheumatoid arthritis, lupus erythematosus (treatable with, e.g., IL-Ira, IL-27, IL-10 or the relevant auto-antigen); allergic diseases including but not limited to asthma, food allergies, (treatable with the relevant allergen); celiac disease (treatable with gluten allergens); neurological disorders including, but not limited to Alzheimer's disease, Parkinson's disease and amyotrophic lateral sclerosis (treatable with, e.g., brain devated neurotropic factor and ciliary neurotropic factor); cancer (treatable with, e.g., IL-1, colony stimulating factors or interferon-W); osteoporosis (treatable with, e.g., transforming growth factor f3); diabetes (treatable with, e.g., insulin); cardiovascular disease (treatable with, e.g., tissue plasminogen activator); atherosclerosis (treatable with, e.g., cytokines and cytokine antagonists); hemophilia (treatable with, e.g., clotting factors); degenerative liver disease (treatable with, e.g., hepatocyte growth factor or interferon a); pulmonary diseases such as cystic fibrosis (treatable with, e.g., alpha antitrypsin); obesity; pathogen infections, e.g., viral or bacterial infections (treatable with any number of the above-mentioned compositions or antigens); etc.

The gram-positive bacteria according to the invention can also be used to treat infectious diseases. In an embodiment, passive immunization against *Clostridium* associated disease, preferably *Clostridium dificile* associated disease (CDAD), with toxin-neutralizing antibodies locally produced and secreted via the gram-positive bacterium according to the invention can be obtained. Preferably, said gram positive bacterium is a *Lactococcus* sp., more preferably *Lactococcus lactis* or a subspecies or a strain thereof.

CDAD is mediated by two exotoxins, toxin A (enterotoxin; see for instance Genbank NC_009089.1, region: 795843 . . . 803975 for DNA sequence or YP_001087137.1 for protein sequence) and toxin B (cytotoxin; see for instance Genbank NC_009089.1, region: 787393 . . . 794493 for DNA sequence or YP_001087135.1 for protein sequence). Both are high-molecular-mass proteins that bind to the surface of intestinal epithelial cells, where they are internalized and catalyze the glucosylation of cytoplasmic rho proteins, leading to cell death, inflammation and diarrhea. They have also been implicated in promoting *C. difficile* virulence, colonization, and neutrophil chemotaxis and activation. The bacteria itself is not invasive and does not cause tissue damage. By neutralizing the *C. difficile* toxins with antibodies, the pathogenic mechanism of the pathogen is blocked, its ability to thrive in the gut may be diminished, and the impact on the microbial ecology could be minimized, allowing recovery of the normal microflora. The medical advantage of this approach could include more rapid recovery, fewer relapses, and relief from selective pressure for antibiotic resistance in normal gut flora.

Accordingly, in an embodiment, the invention relates to a gram-positive bacterium as described herein, in which the polycistronic expression unit comprises an antibody or fragment thereof, preferably a Fab, as described herein elsewhere, directed against toxin A and/or toxin B of *Clostridium*. Most preferably, said antibody or fragment thereof is a neutralizing antibody. In a further embodiment, the invention relates to a gram-positive bacterium, preferably a *Lactococcus* sp. such as *Lactococcus lactis* or an *Enterococcus* sp. such as *Enterococcus faecalis* or *Enterococcus faecium*, comprising a polycistronic expression unit, preferably integrated in the bacterial chromosome, said polycistronic expression unit comprising an endogenous gene, preferably selected from the group consisting of eno, usp45, gap, pyk, rpmB and rplS, preferably originating from a *Lactococcus* sp. or an *Enterococcus* sp., and one or more exogenous genes encoding a neutralizing antibody or antibody fragment, preferably a Fab, against toxin A and/or toxin B of *Clostridium*, preferably *Clostridium dificile*, said polycistronic expression unit being preferably chromosomally integrated at the native locus of said endogenous gene, and said toxin A and/or toxin B antibody (fragment) gene preferably being transcriptionally coupled to the 3' end of said endogenous gene, said transcriptional coupling preferably being effected by an intergenic region, preferably selected from the group consisting of intergenic regions preceding rplW, rplP, rpmD, rplB, rpsG, rpsE, rplN, rplM, rplE, and rplF of a gram-positive bacterium, preferably a *Lactococcus* sp. or a *Enterococcus* sp. The *Clostridium* toxin A and toxin B antibodies as described herein are known in the art (see e.g. Leung et al., J Pediatr 1991; 118(4 Pt 1):633-637; Wilcox. J Antimicrob Chemother 2004; 53(5): 882-884; Sougioultzis et al., Gastroenterology 2005; 128(3): 764-770; Kyne et al., N Engl J Med 2000; 342(6):390-397; Lowy et al., N Engl J Med; 362(3):197-205). Both antibodies or fragments thereof may be located on separate polycistronic expression units in the same or different gram-positive bacterium, but preferably are located on a single polycistronic expression unit. The invention further relates to a method for preventing and/or treating CDAD, comprising administering such gram-positive bacterium.

The skilled reader shall appreciate that the herein specifically recited diseases are only exemplary and their recitation is in no way intended to confine the use of the reagents provided by the invention, e.g., the promoters, nucleic acids, vectors and host cells of the invention, to these particular diseases. Instead, a skilled reader understands that the reagents of the invention can be used to express in principle any expression products, preferably polypeptides, of interest, which may be of therapeutic relevance in not only the recited ones but also in various further diseases or conditions of humans and animals. Consequently, once a suitable expression product, preferably a polypeptide, e.g., an antigen, antibody (fragment) and/or a non-vaccinogenic therapeutically active polypeptide, has been chosen or determined for a given ailment, a skilled person would be able to achieve its expression, isolation and/or delivery using the reagents of the invention.

The invention also contemplates treatment of diseases in other animals including dogs, horses, cats and birds. Diseases in dogs include but are not limited to canine distemper (paramyxovirus), canine hepatitis (adenovirus Cav-1), kennel cough or laryngotracheitis (adenovirus Cav-2), infectious canine enteritis (coronavirus) and haemorrhagic enteritis (parvovirus).

Diseases in cats include but are not limited to viral rhinotracheitis (herpesvirus), feline caliciviral disease (calicivirus), feline infectious peritonitis (parvovirus) and feline leukaemia (feline leukaemia virus). Other viral diseases in horses and birds are also contemplated as being treatable using the methods and compositions of the invention. To this purpose, the use of microorganisms expressing recombinant interferons will be particularly preferred.

As used herein, the pharmaceutical composition preferably comprises a therapeutically effective amount of the gram-positive bacteria of the invention and a pharmaceutically acceptable carrier, i.e., one or more pharmaceutically acceptable carrier substances and/or additives, e.g., buffers, carriers, excipients, stabilisers, etc.

The term "pharmaceutically acceptable" as used herein is consistent with the art and means compatible with the other ingredients of a pharmaceutical composition and not deleterious to the recipient thereof.

The gram-positive bacteria of the invention can be suspended in a pharmaceutical formulation for administration to the human or animal having the disease to be treated. Such pharmaceutical formulations include but are not limited to live gram-positive bacteria and a medium suitable for administration. The gram-positive bacteria may be lyophilized in the presence of common excipients such as lactose, other sugars, alkaline and/or alkali earth stearate, carbonate and/or sulphate (for example, magnesium stearate, sodium carbonate and sodium sulphate), kaolin, silica, flavorants and aromas. Gram-positive bacteria so-lyophilized may be prepared in the form of capsules, tablets, granulates and powders (e.g. a mouth rinse powder), each of which may be administered by the oral route. Alternatively, some gram-positive bacteria may be prepared as aqueous suspensions in suitable media, or lyophilized bacteria may be suspended in a suitable medium just prior to use, such medium including the excipients referred to herein and other excipients such as glucose, glycine and sodium saccharinate.

For oral administration, gastroresistant oral dosage forms may be formulated, which dosage forms may also include compounds providing controlled release of the gram-positive bacteria and thereby provide controlled release of the desired protein encoded therein. For example, the oral dosage form (including capsules, tablets, pellets, granulates, powders) may be coated with a thin layer of excipient (usually polymers, cellulosic derivatives and/or lipophilic materials) that resists dissolution or disruption in the stomach, but not in the intestine, thereby allowing transit through the stomach in favour of disintegration, dissolution and absorption in the intestine.

The oral dosage form may be designed to allow slow release of the gram-positive bacteria and of the produced exogenous proteins, for instance as controlled release, sustained release, prolonged release, sustained action tablets or capsules. These dosage forms usually contain conventional and well known excipients, such as lipophilic, polymeric, cellulosic, insoluble, swellable excipients. Controlled release formulations may also be used for any other delivery sites including intestinal, colon, bioadhesion or sublingual delivery (i.e., dental mucosal delivery) and bronchial delivery. When the compositions of the invention are to be administered rectally or vaginally, pharmaceutical formulations may include ointments, suppositories and creams. In this instance, the gram-positive bacteria are suspended in a mixture of common excipients also including lipids. Each of the aforementioned formulations are well known in the art and are described, for example, in the following references: Hansel et al., Pharmaceutical dosage forms and drug delivery systems, 5th edition, William and Wilkins, 1990; Chien 1992, Novel drug delivery system, 2nd edition, M. Dekker;

Prescott et al. (1989, Novel drug delivery, J.Wiley & Sons); Cazzaniga et al, (1994, Oral delayed release system for colonic specific delivery, Int. J. Pharm.i08:7'.

Preferably, an enema formulation may be used for rectal administration. The term "enema" is used to cover liquid preparations intended for rectal use. The enema may be usually supplied in single-dose containers and contains one or more active substances dissolved or dispersed in water, glycerol or macrogols or other suitable solvents.

Thus, according the invention, in a preferred embodiment, the gram-positive bacteria according to the invention as described herein encoding a desired exogenous gene may be administered to the animal or human via mucosal, e.g., an oral, nasal, rectal, vaginal or bronchial route by any one of the state-of-the art formulations applicable to the specific route. Dosages of gram-positive bacteria for administration will vary depending upon any number of factors including the type of bacteria and the gene encoded thereby, the type and severity of the disease to be treated and the route of administration to be used.

Thus, precise dosages cannot be defined for each and every embodiment of the invention, but will be readily apparent to those skilled in the art once armed with the present invention. The dosage could be anyhow determined on a case by case way by measuring the serum level concentrations of the recombinant protein after administration of predetermined numbers of cells, using well known methods, such as those known as ELISA or Biacore (see examples). The analysis of the kinetic profile and half life of the delivered recombinant protein provides sufficient information to allow the determination of an effective dosage range for the transformed host cells.

In an embodiment, when the gram-positive bacteria according to the invention as described herein express an antigen, the invention may thus also provide a vaccine.

The term "vaccine" identifies a pharmaceutically acceptable composition that, when administered in an effective amount to an animal or human subject, is capable of inducing antibodies to an immunogen comprised in the vaccine and/or elicits protective immunity in the subject.

The vaccine of the invention would comprise the gram-positive bacteria according to the invention as described herein and further optionally an excipient. Such vaccines may also comprise an adjuvant, i.e., a compound or composition that enhances the immune response to an antigen. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, and potentially useful pharmaceutically acceptable human adjuvants such as BCG (bacille Calmette-Guerin) and *Corynebacterium parvum.*

It is thus made apparent that there have been provided in accordance with the invention, biomarkers, uses and methods that provide for substantial advantages in the diagnosis, prediction, prognosis and/or monitoring of impaired fracture healing. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The aspects and embodiments of the invention are further supported by the following non-limiting examples.

EXAMPLES

Example 1: Selection of Intergenic Regions from the *Lactococcus lactis* Genome

Figure 1:
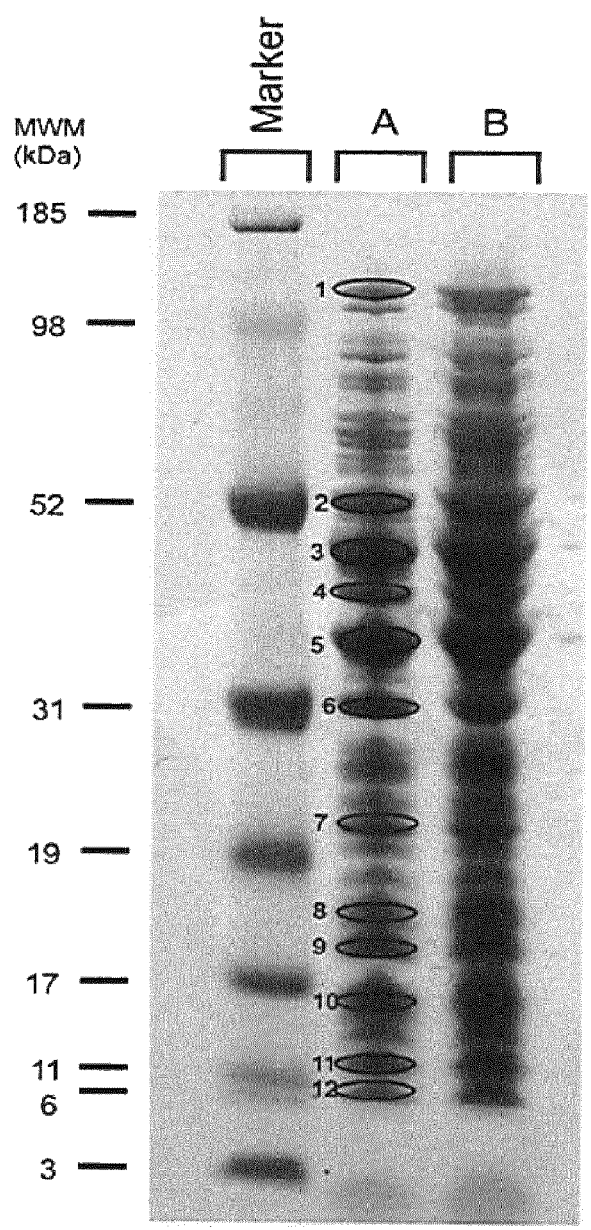
FIG. 1: Coomassie blue staining of cellular proteins of a *Lactococcus lactis* ssp. *Cremoris* strain MG1363 end-log culture. Prominent protein bands are indicated 1 to 12.

Cellular proteins of an end-log culture of *Lactococcus lactis* ssp. *cremoris* strain MG1363 were visualized onto a protein gel with Coomassie blue staining, as indicated in FIG. 1. Lanes A and B contained 29 μg and 58 μg MG1363 proteins, respectively. 12 defined proteins bands from lane A were isolated from the gel. Proteins were isolated and intergenic regions were identified by:
 1) Identification of abundantly expressed proteins in the fragments by partial peptide sequencing (MALDI-TOF/TOF) and database search using combined peptide masses and sequence information
 2) Identification, using the chromosome sequence of *Lactococcus lactis* ssp. *cremoris* strain MG1363 (Wegmann et al), of genes encoding the abundantly expressed proteins (1) that are present in an operon, but not as a "first gene"
 3) Identification of intergenic regions that precede these abundantly expressed genes Table 3 lists thus identified intergenic regions. Underlined sequences represent ribosome binding sites.

TABLE 3

| Intergenic region | 2$^{nd}$ gene | Function 2$^{nd}$ gene |
| --- | --- | --- |
| TAATG (SEQ ID NO: 1) | rplW | 50 S ribosomal protein L23 |
| TAATCCATG (SEQ ID NO: 2) | rplP | 50 S ribosomal protein L16 |
| TAAGGAGGAAAAAATG (SEQ ID NO: 3) | rpmD | 50 S ribosomal protein L30 |
| TAATAGAGGAGGAAAATCGTG (SEQ ID NO: 4) | rplB | 50 S ribosomal protein L2 |
| TAAGAAGGGAGATAAGTAAGAATG (SEQ ID NO: 5) | rpsG | 30 S ribosomal protein S7 |
| TAAGGAAAGGGGTAATTAAACATG (SEQ ID NO: 6) | rpsE | 30 S ribosomal protein S5 |

TABLE 3-continued

| Intergenic region | 2$^{nd}$ gene | Function 2$^{nd}$ gene |
|---|---|---|
| TAAGCAAAACTAGGAGGAATATAGCATG (SEQ ID NO: 7) | rplN | 50 S ribosomal protein L14 |

Example 2: Selection of Sites for Bicistronic Expression

Table 4 lists target promoters identified in Example 1 as driving high level expression. These promoters can be used as target sites for polycistronic expression of exogenous genes.

TABLE 4

| Band | Gene as annotated in MG1363 | Name |
|---|---|---|
| 1 | DNA-directed RNA polymerase, beta' subunit/160 kD subunit | rpoC |
|  | DNA-directed RNA polymerase, beta subunit/140 kD subunit | rpoB |
|  | non-heme iron-binding ferritin | dpsA |
| 2 | pyruvate kinase | pyk |
|  | glutamyl -tRNA synthetases | gltX |
| 3 | phosphopyruvate hydratase | eno |
|  | glutamine synthetase | glnA |
|  | glutamine synthetase repressor | glnR |
|  | dipeptidase PepV | pepV |
|  | F0F1-type ATP synthase beta subunit (ATP synthase F1 beta subunit) | atpD |
|  | F0F1-type ATP synthase alpha subunit | atpA |
| 4 | multiple sugar-binding transport ATP-binding protein | msmK |
|  | acetoin dehydrogenase complex E1 component alpha subunit (acoA) | pdhA |
|  | cell division protein | ftsA |
|  | UDP-galactopyranose mutase | glfl |
|  | 3-phosphoglycerate kinase | pgk |
|  | glyceraldehyde-3-phosphate dehydrogenase | gapB |
|  | acetate kinase | ackA1 |
|  | 3-oxoacyl-(acyl-carrier-protein) synthase II | fabF |
| 5 | 3-ketoacyl-(acyl-carrier-protein) reductase | fabG |
|  | DNA-directed RNA polymerase, alpha subunit/40 kD subunit | rpoA |
|  | Proline dipeptidase | pepQ |
|  | glutamyl aminopeptidase | pepA |
|  | predicted dehydrogenase related protein | llmg_0272 |
| 6 | 30S ribosomal protein S2 | rpsB |
|  | 50S ribosomal protein L4 (rplD) | rplD |
|  | 50S ribosomal protein L23 | rplW |
|  | 50S ribosomal protein L2 | rplB |
|  | Phenylalanyl-tRNA synthetase beta chain | pheT |
|  | fructose-bisphosphate aldolase | fbaA |
| 7 | 30S ribosomal protein S4 | rpsD |
|  | translation initiation factor 3 (IF-3) | infC |
|  | transcription elongation factor GreA | greA |
|  | protease subunit of ATP-dependent Clp protease | clpP |
|  | superoxide dismutase | sodA |
| 8 | 30S ribosomal protein S12 | rpsL |
|  | 30S ribosomal protein S7 | rpsG |
|  | 50S ribosomal protein L18 | rplR |
|  | 30S ribosomal protein S5 | rpsE |
|  | 50S ribosomal protein L30/L7E | rpmD |
|  | S-ribosylhomocysteinase | luxS |
|  | 50S ribosomal protein L15 | rplO |
|  | 50S ribosomal protein L11 | rplK |
| 9 | 30S ribosomal protein S8 | rpsH |
|  | 50S ribosomal protein L21 | rplU |
|  | 30S ribosomal protein S13 | rpsM |

TABLE 4-continued

| Band | Gene as annotated in MG1363 | Name |
|---|---|---|
|  | 30S ribosomal protein S19 (rpsS) | rpsS |
|  | ribosomal protein L22 (rplV) | rplV |
|  | ribosomal protein L16 (rplP) | rplP |
|  | ribosomal protein L14 (rplN) | rplN |
|  | 30S ribosomal protein L19 | rplS |
|  | 30S ribosomal protein S11 | rpsK |
| 10 | 30S ribosomal protein S10 | rpsJ |
|  | co-chaperonin GroES | groES |
|  | 50S ribosomal protein L24 | rplX |
|  | 50S ribosomal protein L10 | rplJ |
|  | 50S ribosomal protein L7/L12 | rplL |
| 11 | HU-like DNA-binding protein | hllA |
|  | 50S ribosomal protein L28 | rpmB |
|  | phosphotransferase system IIB component | ptcB |

Figure 2:
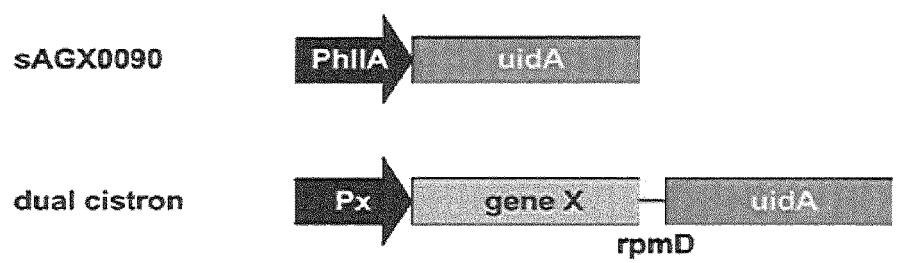
FIG. 2: Representation of a reference, monocistronic expression construct (top, sAGX0090) and polycistronic (bicistronic, dual cistron) construct according to an embodiment of the invention (bottom) whereby gene X represents an endogenous gene. Both expression constructs are intended for the expression of β-glucuronidase from the *E. coli* uidA gene, serving here as an exemplary exogenous gene.

The β-glucuronidase (uidA) gene from *E. coli* was introduced as reporter gene in *Lactococcus lactis* MG1363. The uidA gene product β-glucuronidase, catalyses the cleavage of a wide variety of β-glucuronides that are commercially available as histochemical and spectrophotometric substrates. Strain sAGX0090 has the PhllA>>uidA expression cassette at the thyA locus (FIG. 2). This promoter was also used in strains sAGX0037 and sAGX0085.

As depicted in FIG. 2, dual cistron constructs were made by inserting uidA in the *Lactococcus lactis* MG1363 chromosome at the 3' end of several endogenous genes (gene X). Hereby, rpmD was used as intergenic sequence between the endogenous genes of interest from Table 4 and uidA to identify sites that result in higher β-glucuronidase (GUS) activity compared to sAGX0090.

*Lactococcus lactis* cultures were grown for 16 hours at 30° C. in GM17 supplemented with thymidine when needed. Cells of 1 ml culture were washed and resuspended in 1 ml demineralized water. Cells were disrupted with MP Biomedicals lysing matrix B and Fasprep-24 device at 6 m/s for 40 seconds. Tubes were centrifuged and a dilution series of the cell supernatant was made. GUS activity was measured by adding p-nitrophenyl substrate and β-mercaptoethanol which gives the solution a yellow colour upon presence of β-glucuronidase. GUS activity was measured at 405 nm and expressed relatively to reference strain sAGX0090. All strains were treated in parallel.

Figure 3:
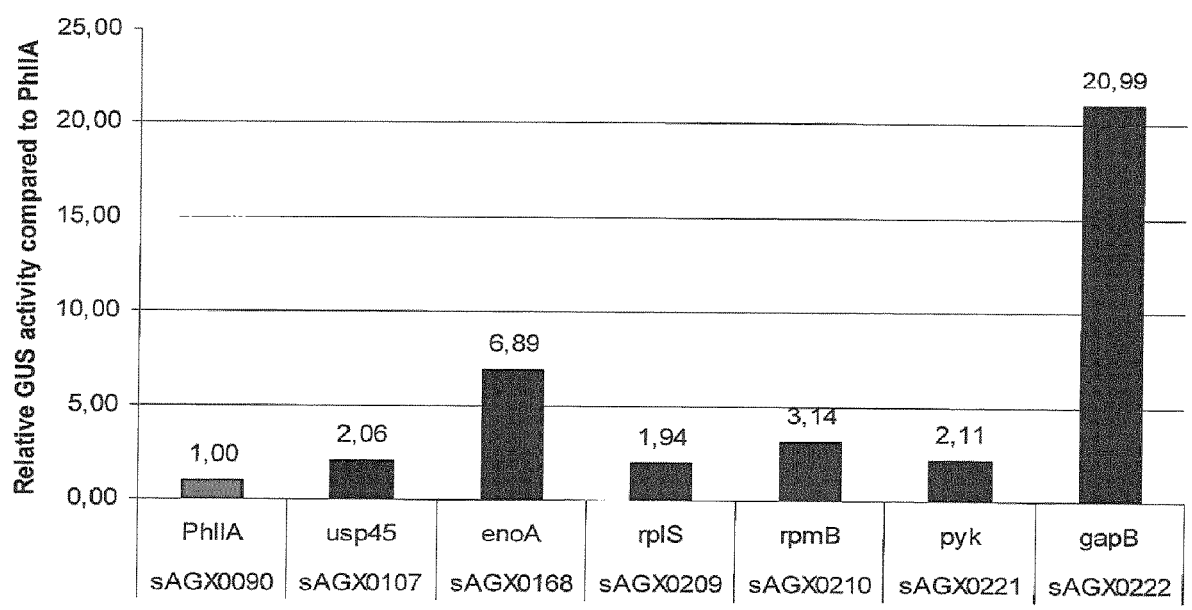
FIG. 3: Relative β-glucuronidase (GUS)-activity in a reference host (monocistronic: PhllA>>uidA, sAGX0090) and in a host comprising a polycistronic (bicistronic) construct according to an embodiment of the invention (endogenous gene X>>rpmD>>uidA), organized as in FIG. 2. The endogenous genes X are, in this example, usp45, enoA, rplS, rpmB, pyk and gapB. In this example, the rpmD intergenic region provides transcriptional coupling of the endogenous and the exogenous gene. The exogenous *E. coli* uidA gene encodes β-glucuronidase. All expression constructs are embedded in the bacterial chromosome. The monocistronic construct is present in the thyA locus, bicistronic constructs are embedded at the native position of geneX. The data show that all bicistronic constructs have b-galactosidase activity superior to the monocistronic PhllA>>uidA construct.

FIG. 3 shows relative GUS-activity of gene X>>rpmD>>uidA dual cistron constructs. GUS-activity is expressed relatively to reference strain sAGX0090 that carries the PhllA>>uidA expression cassette and is indicated on the Y-axis. GUS-activity in all dual cistron strains was found to be higher than the reference strain. In particular, GUS-activity in sAGX0168 (enoA>>rpmD>>uidA) and sAGX0222 (gapB>>rpmD>>uidA) was found to be 6.89 and 20.99 times higher when compared to sAGX0090, respectively.

These results clearly confirm that bicistronic expression allows enhanced protein expression levels over a wide variety of settings.

Example 3: Bicistronic Expression of Human Pro-Insulin

Figure 4:
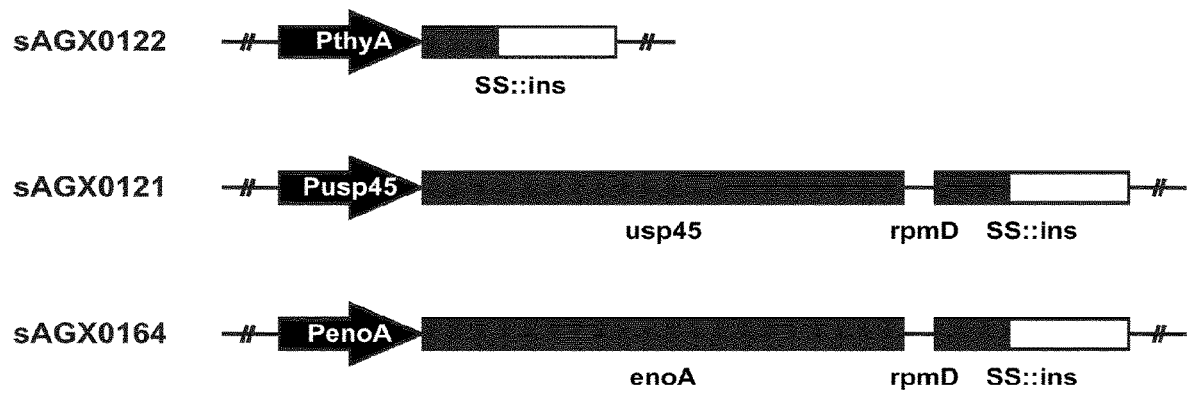
FIG. 4: Quantification of human pro-insulin (ins) secretion by *Lactococcus lactis* in a reference host (sAGX0122) and hosts according to an embodiment of the invention (sAGX0121 and sAGX0164). (A) Schematic overview of ins expression modules. Strain sAGX0122 carries a monocistronic expression construct in which the thyA promoter drives the expression of a secretion leader—human pro-insulin fusion (SS::ins), embedded in the *Lactococcus lactis* MG1363 chromosome at the thyA locus. Bicistronic expression constructs in sAGX0121 and sAGX0164 consist of a transcriptional coupling of the endogenous usp45 and enoA respectively with SS::ins, through the rpmD intergenic region. These constructs are located on the *Lactococcus lactis* MG1363 chromosome at the native positions of the usp45 and enoA genes respectively. (B) Levels of pro-insulin detected in the supernatants of the various strains. Strain codes (sAGX0122, sAGX0121 and sAGX0164) are indicated underneath the columns respectively indicating human pro-insulin levels in the supernatants of these strains. The data show that strains carrying both bicistronic constructs have human pro-insulin levels superior to the strain carrying the monocistronic PthyA>>ins construct.
Figure 4:
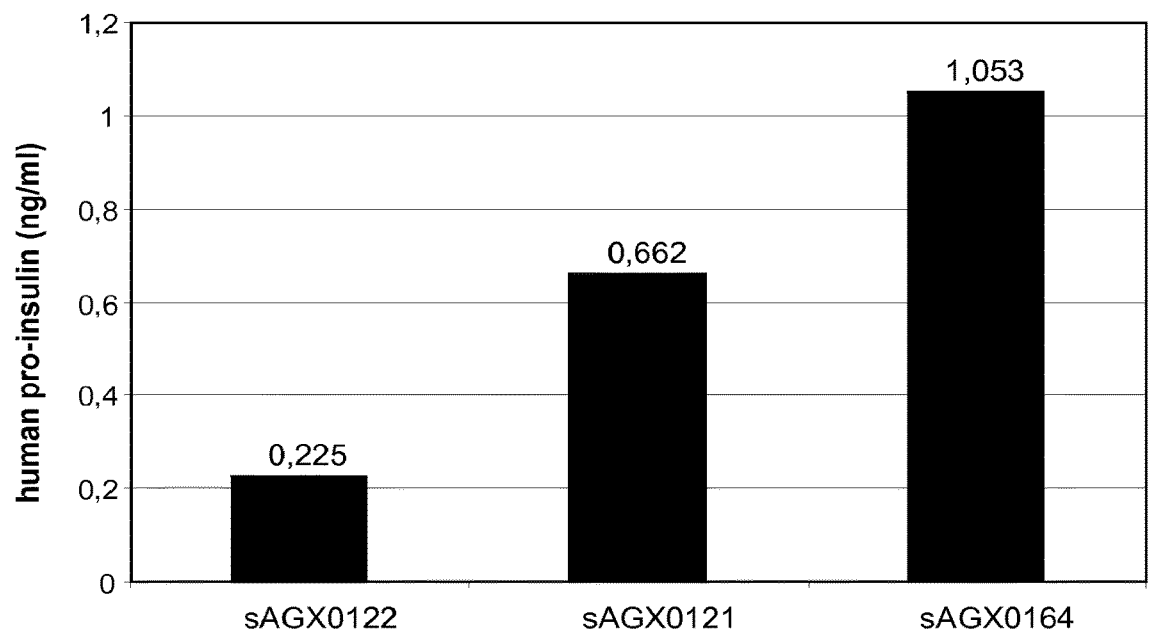

The usp45 secretion leader (SS) was fused to human pro-insulin (ins) to obtain secretion of pro-insulin (SS::ins). The [SS::ins] expression cassette was either integrated in the *Lactococcus lactis* MG1363 chromosome at the thyA locus and expressed directly from PthyA (sAGX0121) or was inserted, along with the rpmD intergenic region preceding SS::ins, as a second cistron downstream from usp45 (sAGX0121) or enoA (sAGX0164) (FIG. 4*a*). The insulin secretion capacity was quantified by ELISA to evaluate bicistronic expression of cargo compared to PthyA driven expression at the thyA locus.

Attempts to construct a PhllA>>SS::Ins integration plasmid have failed.

Strains were inoculated from single colony into 2 ml GM17 supplemented with 200 µM thymidine when needed and grown for 16 hours at 30° C. For the quantification of pro-insulin secretion, these saturated overnight cultures were diluted 1/25 in 5 ml fresh GM17 medium and grown for 4 hours at 30° C. Cells were collected by centrifugation at 3220×g for 10 minutes, resuspended in an equal amount BAM9 medium and cultured for another 3 hours at 30° C. BAM9 contains M9 salts, 0.5% aminoplasmal, 0.5% glucose, 25 mM NaHCO$_3$, 25 mM Na$_2$CO$_3$, 2 mM MgSO$_4$, 0.1 mM CaCl$_2$ and 200 µM thymidine. Cells and culture supernatants were separated by centrifugation at 3220×g for 10 minutes. The amount of secreted human pro-insulin in the culture supernatant was quantified by ELISA provided by Mercodia. All strains were treated in parallel.

FIG. 4*b* represents the quantification of human pro-insulin secretion by *Lactococcus lactis* strains sAGX0122, sAGX0121 and sAGX0164, The amount of secreted pro-insulin was expressed as ng/ml and indicated on the Y-axis. The figure clearly demonstrates that strains comprising a bicistronic expression cassette have a significantly higher cargo expression than reference strain. In particular, insulin secretion was highest when SS::ins was coupled through rpmD to enoA.

Example 4: Bicistronic Expression of cA2 Fab

Dual cistron expression constructs were generated with heavy chain and light chain of cA2 anti-hTNF Fab. All expression units are driven by the thyA promoter and are located on plasmids. All carry genes for the light chain, VLCL (L) and the Fab fragment of the heavy chain, VHCH1 (H), derived from the cA2 infliximab monoclonal antibody. L>>H and H>>L configurations are coupled by intergenic regions preceding rpmD, rplB, rpsG, rpsE or rplN. All constructs are plasmid borne.

Figure 5:
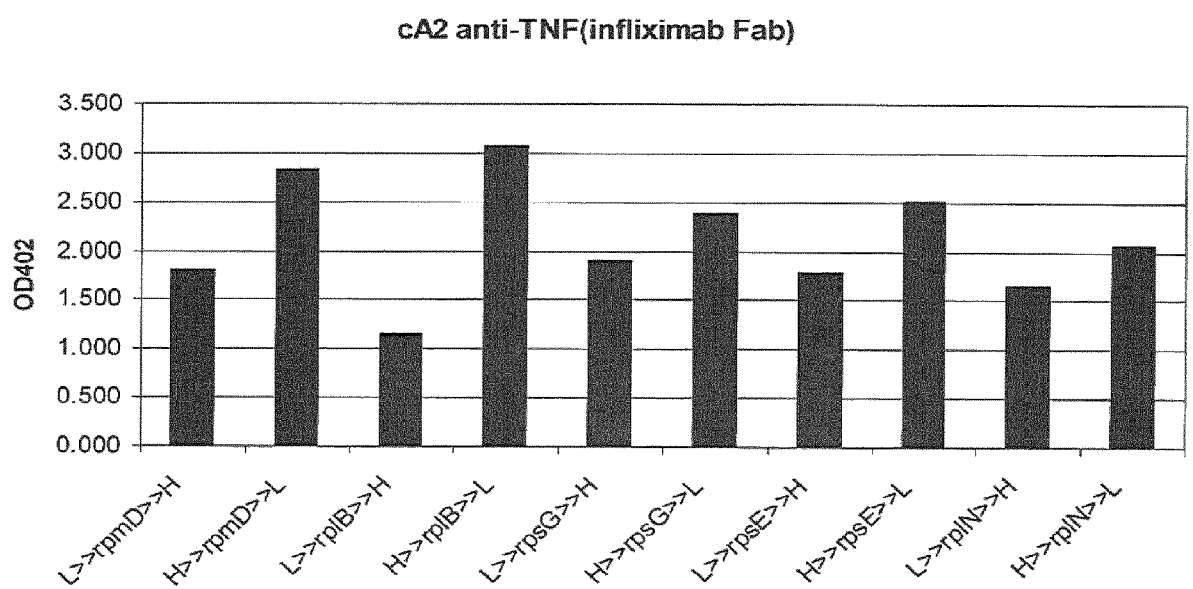
FIG. 5: cA2 anti-TNF Fab expression in *Lactococcus lactis*. Genes encoding VLCL (L) and VHCH1 (H) fragments were transcriptionally coupled by rpmD, rplB, rpsG, rpsE and rplN intergenic regions. Constructs were made in which either L or H are positioned as the first gene of the bicistronic construct. All anti-TNF expression constructs were plasmid borne and placed under the control of the PthyA promoter. Anti-TNF activity was measured in the supernatants of the various strains. The data show that there is higher anti-TNF activity in all constructs where H is the first gene of the bicistronic construct.

FIG. 5 reveals that both heavy chain and light chains were highly expressed by the dual cistron constructs, leading to high levels of functional cA2 anti-TNF Fab. FIG. 5 further reveals that cA2 anti-TNF expression increased when the heavy chain was positioned before the light chain, irrespective of the intergenic region.

For the quantification of anti-hTNF secretion, strains were inoculated from single colony into 2 ml GM17 and grown for 16 hours at 30° C. These saturated overnight cultures were diluted 1/25 in 5 ml fresh GM17 medium and grown for 4 hours at 30° C. Cells were collected by centrifugation at 3220×g for 10 minutes, resuspended in an equal amount BAM9 medium and cultured for another 3 hours at 30° C. BAM9 contains M9 salts, 0.5% aminoplasmal, 0.5% glucose, 25 mM NaHCO$_3$, 25 mM Na$_2$CO$_3$, 2 mM MgSO$_4$, 0.1 mM CaCl$_2$ and 200 µM thymidine. Cells and culture supernatants were separated by centrifugation at 3220×g for 10 minutes. Crude supernatants from strains carrying the individual constructs were prepared in parallel and were assayed for the presence of anti-TNF activity. This was done by direct ELISA using human TNF as capture protein. VLCL portions were detected by rabbit anti-human IgG antiserum and revealed by alkaline phosphatase conjugated anti-rabbit antiserum. Phosphatase activity was measured by colorimetric assay and read out as OD402. All strains were treated in parallel.

Example 5: Bicistronic Expression of CDP870

Dual cistron expression constructs were generated with heavy chain and light chain of CDP870 anti-TNF Fab. All expression units are located on the bacterial chromosome.

Figure 6:
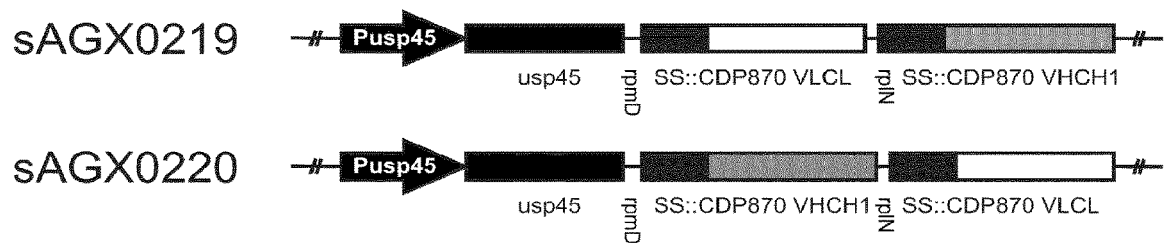
FIG. 6: CDP870 anti-TNF Fab expression in *Lactococcus lactis*. (A) CDP870 light and heavy chain fusions to usp45 secretion leader encoding sequences (SS::CDP870 VLCL and SS::CDP870 VHCH1) were inserted as a second and third cistron downstream from usp45 (sAGX0219, sAGX0220) in the *Lactococcus lactis* MG1363 chromosome. In sAGX0219 and sAGX0220, rpmD was used to couple SS::CD870 genes to usp45. To avoid genetic instability, light and heavy chain genes were coupled through the intergenic region preceding rplN. In sAGX0219, the light chain gene precedes the heavy chain gene, while in sAGX0220, the heavy chain gene precedes the light chain gene. (B) Quantification of anti-human TNF activity in crude culture supernatants. Both heavy chain and light chains were highly expressed by the dual cistron constructs, leading to high levels of functional CDP870 anti-TNF Fab. CDP870 anti-TNF expression substantially increased when the heavy chain was positioned before the light chain.
Figure 6:
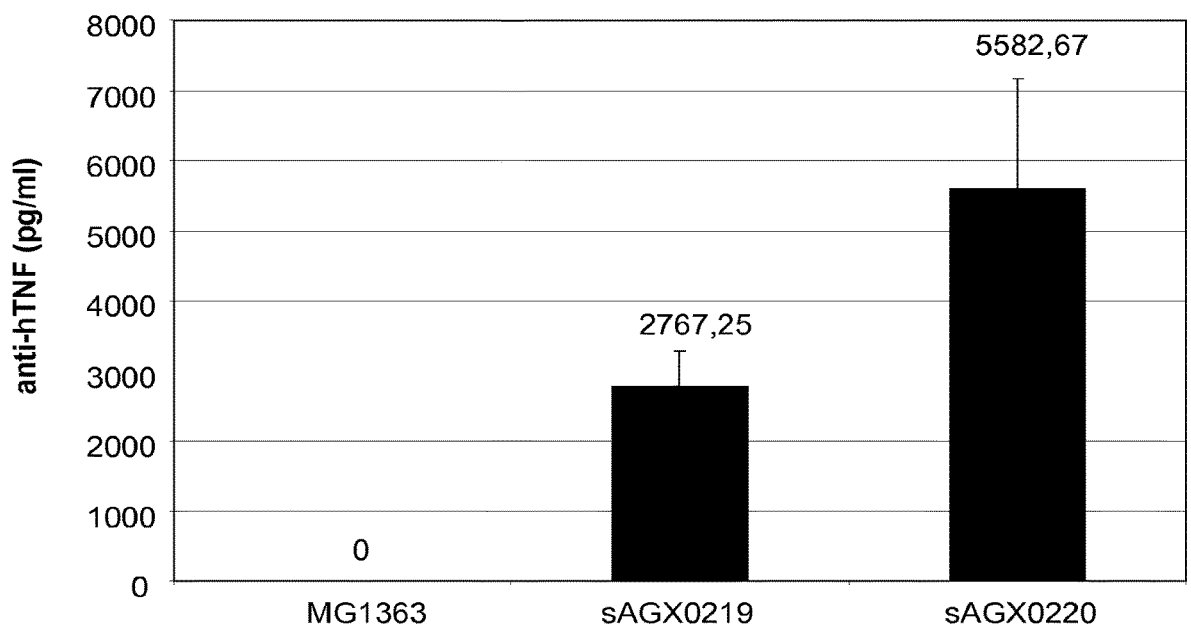

FIG. 6*a*: CDP870 light and heavy chain Fab fusions to usp45 secretion leader encoding sequences (SS::CDP870 VLCL and SS::CDP870 VHCH1) were inserted as a second and third cistron downstream from usp45 (sAGX0219, sAGX0220). In sAGX0219 and sAGX0220, rpmD was used to couple SS::CD870 genes to usp45. To avoid genetic instability, light and heavy chain genes were coupled through the intergenic region preceding rplN. In sAGX0219, the light chain gene precedes the heavy chain gene, while in sAGX0220, the heavy chain gene precedes the light chain gene.

For the quantification of anti-hTNF secretion, strains were inoculated from single colony into 2 ml GM17 and grown for 16 hours at 30° C. These saturated overnight cultures were diluted 1/25 in 5 ml fresh GM17 medium and grown for 4 hours at 30° C. Cells were collected by centrifugation at 3220×g for 10 minutes, resuspended in an equal amount BAM9 medium and cultured for another 3 hours at 30° C. BAM9 contains M9 salts, 0.5% aminoplasmal, 0.5% glucose, 25 mM NaHCO$_3$, 25 mM Na$_2$CO$_3$, 2 mM MgSO$_4$, 0.1 mM CaCl$_2$ and 200 µM thymidine. Cells and culture supernatants were separated by centrifugation at 3220×g for 10 minutes. Crude supernatants from strains carrying the individual constructs were prepared in parallel and were assayed for the presence of anti-TNF activity. This was done by direct ELISA using human TNF as capture protein with Remicade as a reference standard. VLCL portions were detected by rabbit anti-human IgG antiserum and revealed by alkaline phosphatase conjugated anti-rabbit antiserum. Phosphatase activity was measured by colorimetric assay and read out as OD402. All strains were treated in parallel.

FIG. 6*b* reveals that both heavy chain and light chains were highly expressed by the dual cistron constructs, leading to high levels of functional CDP870 anti-TNF Fab. FIG. 6*b* further reveals that CDP870 anti-TNF expression substantially increased when the heavy chain was positioned before the light chain.

Example 6: Bicistronic Expression of Human Trefoil Factor 1 (hTFF1)

Expression constructs were generated with the usp45 secretion leader coding sequence fused to hTFF1 (SS::hTFF1). All expression units are located on the bacterial chromosome. It was not possible to construct integration plasmids for monocistronic hTFF1 expression using stronger promoters than PhllA.

Figure 7:
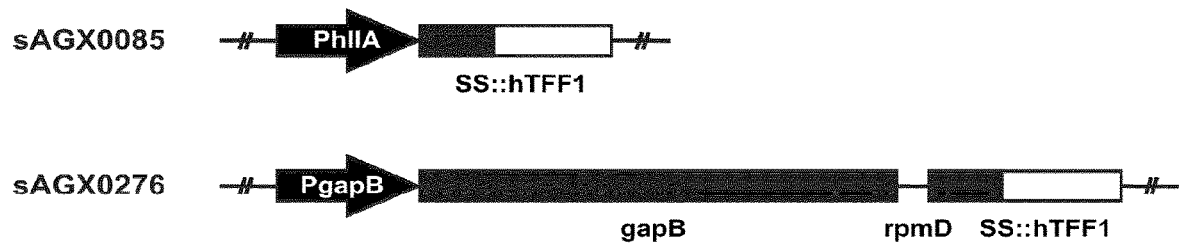
FIG. 7: Quantification of human trefoil factor-1 (hTFF1) secretion by *Lactococcus lactis* in a reference host (sAGX0085) and a host according to an embodiment of the invention (sAGX0276). (A) Schematic overview of hTFF1 expression modules. Strain sAGX0085 carries a monocistronic expression construct in which the PhllA promoter drives the expression of a secretion leader-hTFF1 fusion (SS::hTFF1), embedded in the *Lactococcus lactis* MG1363 chromosome at the thyA locus. The bicistronic expression construct in sAGX0276 consist of a transcriptional coupling of gapB with SS::hTFF1, through the rpmD intergenic region. This construct is located on the *Lactococcus lactis* MG1363 chromosome at the native positions of the gapB gene. (B) Levels of hTFF1 detected in the supernatants of the various strains. Strain codes (sAGX0085 and sAGX0276) are indicated underneath the columns respectively indicating human hTFF1 levels in the supernatants of these strains. The data show that sAGX0276, carrying the bicistronic construct produces hTFF1 levels superior to sAGX0085 which holds the monocistronic construct.
Figure 7:
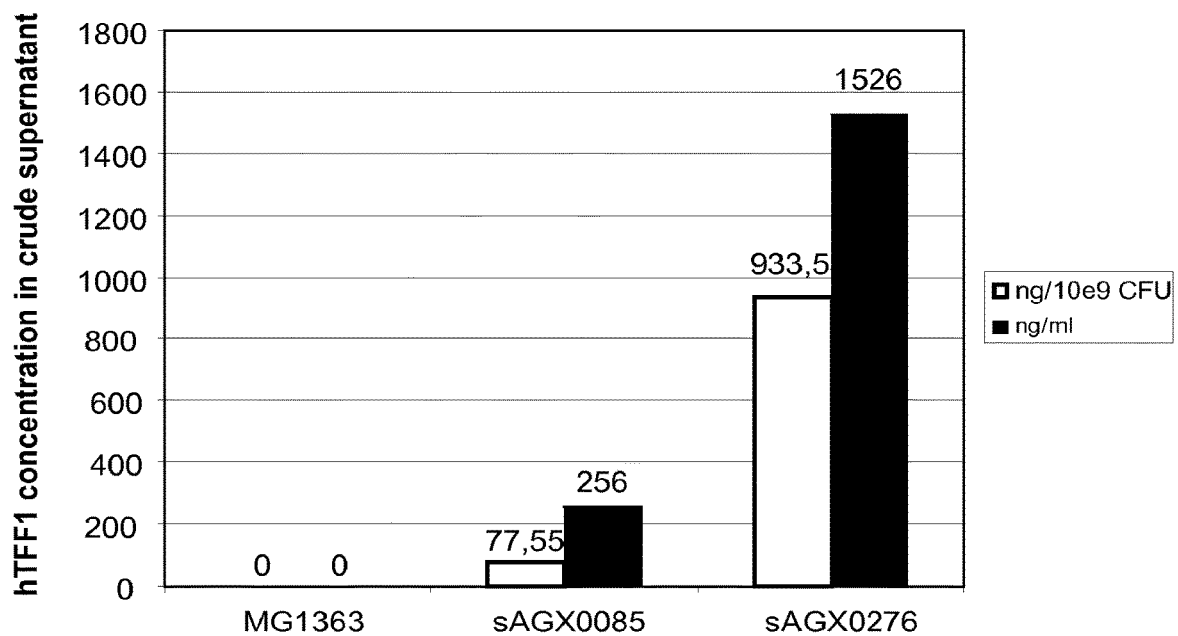

FIG. 7*a*: The usp45 secretion leader coding sequence (SS) was fused to hTFF1 to obtain secretion of hTFF1 (SS::hTFF1). The SS::hTFF1 expression cassette was either integrated in the *Lactococcus lactis* MG1363 chromosome at the thyA locus and expressed directly from PhllA (sAGX0085) or was inserted, along with the rpmD intergenic region preceding SS::hTFF1, as a second cistron downstream from gapB (sAGX0276).

FIG. 7b: The hTFF1 secretion capacity was quantified by ELISA to evaluate bicistronic expression of cargo compared to PhllA driven expression at the thyA locus.

For the quantification of hTFF1 secretion, strains were inoculated from single colony into 2 ml GM17 and grown for 16 hours at 30° C. These saturated overnight cultures were diluted 1/25 in 5 ml fresh GM17 medium and grown for 4 hours at 30° C. Cells were collected by centrifugation at 3220×g for 10 minutes, resuspended in an equal amount BAM9 medium and cultured for another 3 hours at 30° C. BAM9 contains M9 salts, 0.5% aminoplasmal, 0.5% glucose, 25 mM $NaHCO_3$, 25 mM $Na_2CO_3$, 2 mM $MgSO_4$, 0.1 mM $CaCl_2$ and 200 μM thymidine. At this stage, colony forming units (CFU) of all cultures were determined. Cells and culture supernatants were separated by centrifugation at 3220×g for 10 minutes. Crude supernatants from strains carrying the individual constructs were prepared in parallel and were assayed by ELISA using purified hTFF1 as a reference standard. The amount of secreted hTFF1 was expressed as ng/ml and $ng/10^9$ CFU. All strains were treated in parallel.

FIG. 7b clearly demonstrates that the strain comprising a bicistronic expression cassette (sAGX0276) has a significantly higher cargo expression than reference strain (sAGX0085). The amount of secreted hTFF1 expression was substantially enhanced (>5 fold per ml; >12 fold per CFU) when hTFF1 was coupled through rpmD to gapB.

Figure 8:
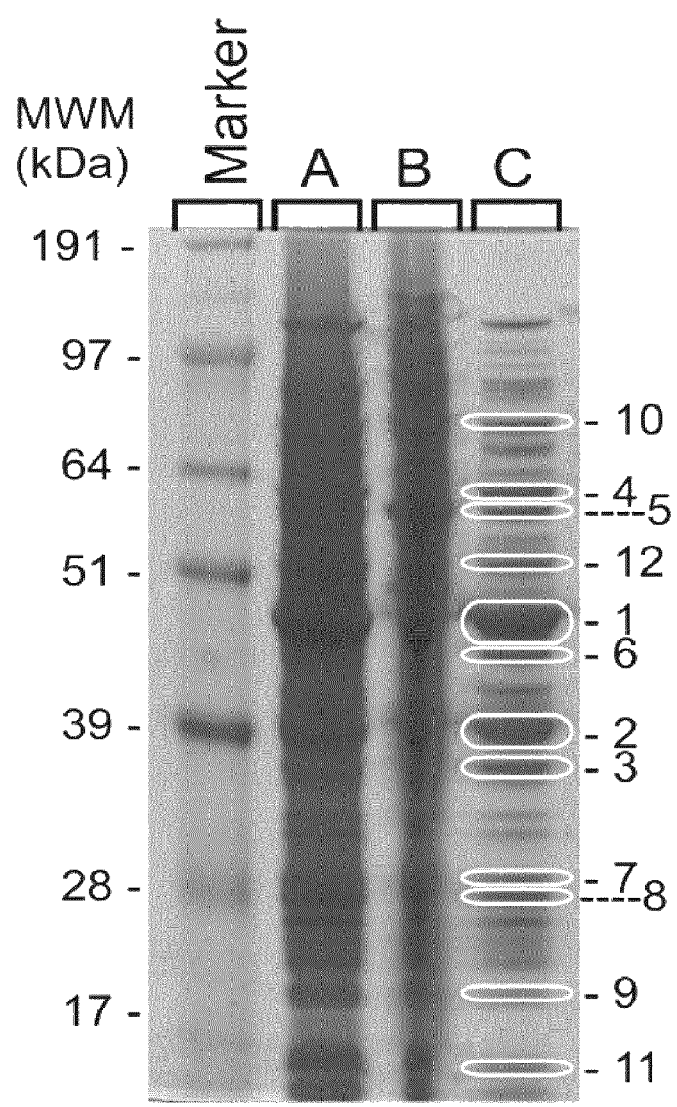
FIG. 8: Coomassie blue staining of cellular proteins of a *Enterococcus faecium* strain LMG 15709 end-log culture. Prominent protein bands are indicated 1 to 12.

Example 7: Selection of Intergenic Regions from the *Enterococcus faecium* Genome Cellular proteins of an end-log culture of *Enterococcus faecium* strain LMG 15709 (*Enterococcus faecium* [Orla-Jensen 1919] Schleifer and Kilpper-Bälz 1984 VP; LMG 15709; ATCC 6057; DSM 2146; NCIMB 8842) were visualized onto a protein gel with Coomassie blue staining, as indicated in FIG. 8. Lanes A, B and C contained the cellular proteins of the lysed cell equivalent of 284 μl, 142 μl and 56.8 μl end-log culture of *Enterococcus faecium* LMG15709, respectively. 12 defined proteins bands from lane C were isolated from the gel. Proteins were isolated and intergenic regions were identified by:

1) Identification of abundantly expressed proteins in the fragments by partial peptide sequencing (MALDI-TOF/TOF) and database search using combined peptide masses and sequence information.

2) Identification, using the chromosome sequence of *Enterococcus faecium* PC4.1 (retrieved form the NCBI Genome databank, GenBank accession number ADMM01000000), of genes encoding the abundantly expressed proteins (1) that are present in an operon, but not as a "first gene".

3) Identification of intergenic regions that precede these abundantly expressed genes (Table 5).

Table 5 lists identified intergenic regions in *Enterococcus faecium* LMG15709. Underlined sequences represent ribosome binding sites.

TABLE 5

| Intergenic region | $2^{nd}$ gene | Function $2^{nd}$ gene |
| --- | --- | --- |
| TAAT (SEQ ID NO: 8) | rplP | 50S ribosomal protein L16 |
| TAAGGAGGACAACAATA (SEQ ID NO: 9) | rpmD | 50S ribosomal protein L30 |
| TAATAGGAGGGAATTTCA (SEQ ID NO: 10) | rplM | 50S ribosomal protein L13 |
| TTAGAAGAAGGAGGAATACCATTC (SEQ ID NO: 11) | rpsE | 30S ribosomal protein S5 |
| TAAAAGTTTAAGGAAGGAGGGTCTTACTGA (SEQ ID NO: 12) | rplE | 50S ribosomal protein L5 |
| TAATCAAGTAGAATCTACAAGGAGGTGTCTTTAA (SEQ ID NO: 13) | rplF | 50S ribosomal protein L6 |

Example 8: Selection of Sites in the *Enterococcus faecium* Genome for Bicistronic Expression Table 6 lists highly expressed *Enterococcus faecium* genes identified in Example 7 as driving high level expression. Promoters driving these genes can be used as target sites for polycistronic expression of exogenous genes. These endogenous genes can further be used as first gene in a polycistronic expression module, transcriptionally or translationally coupled, through an intergenic region, to downstream exogenous genes.

TABLE 6

| Band | Gene annotation | Name |
| --- | --- | --- |
| 1 | Enolase [*Enterococcus faecium* DO]; gi|69249235 | eno |
|  | Elongation factor Tu [*Enterococcus faecium* TX13330]; gi|227550718 | tuf |
| 2 | Glyceraldehyde-3-phosphate dehydrogenase [*Enterococcus faecium* TX1330]; gi|227552066 | gap |

TABLE 6-continued

| Band | Gene annotation | Name |
|---|---|---|
| 3 | L-lactate dehydrogenase [*Enterococcus faecium* DO]; gi|69245441 | ldh |
| | Aspartate carbamoyltransferase [*Enterococcus faecium* DO]; gi|69247601 | pyrB |
| | Ribose-phosphate pyrophosphokinase [*Enterococcus faecium* DO]; gi|69245416 | |
| 4 | Pyruvate kinase [*Enterococcus faecium* DO]; gi|69247355 | pyk |
| | Oligoendopeptidase F [*Enterococcus faecium* E1039]; gi|293553061 | pepF |
| | Aspartyl-tRNA synthetase bacterial/mitochondrial type [*Enterococcus faecium* DO]; gi|69247937 | aspS |
| 5 | Lysyl-tRNA synthetase [*Enterococcus faecium* TX1330]; gi|227552660 | lysS |
| | GroEL [*Enterococcus faecium*]; gi|35187728 | groEL |
| 6 | Phosphoglycerate kinase [*Enterococcus faecium* E1039]; gi|293557157 | pgk |
| 7 | Fructose-bisphosphate aldolase class-II [*Enterococcus faecium* 1,230,933]; gi|293557157 | |
| | 2,3-bisphosphoglycerate-dependent phosphoglycerate mutase [*Enterococcus faecium* E1039]; gi|293556592 | |
| | Saicar synthetase [*Enterococcus faecium* 1,141,733]; gi|257887626 | purC |
| 8 | 2,3-bisphosphoglycerate-dependent phosphoglycerate mutase [*Enterococcus faecium* E1039]; gi|293556592 | |
| | Saicar synthetase [*Enterococcus faecium* 1,231,501]; gi|257884790 | purC |
| 9 | 50S ribosomal protein L5 [*Enterococcus faecium* DO]; gi|69247181 | rplE |
| | 50S ribosomal protein L6 [*Enterococcus faecium* DO]; gi|69247184 | rplF |
| | Peroxiredoxin [*Enterococcus faecium* TX1330]; gi|227551517 | aphC |
| | Xanthine phosphoribosyltransferase [*Enterococcus faecium* 1,230,933]; gi|257878081 | |
| 10 | Elongation factor G [*Enterococcus faecium* TX1330]; gi|227550717 | fusA |
| 11 | 30S ribosomal protein S5, bacterial and organelle form [*Enterococcus faecium* DO]; gi|69247186 | rpsE |
| | 50S ribosomal protein L16 [*Enterococcus faecium*]; gi|9931590 | rplP |
| | Universal stress protein family [*Enterococcus faecium* E980]; gi|293571359 | |
| | Ferritin [*Enterococcus faecium* 1,230,933]]; gi|257880413 | |
| | 30S ribosomal protein S7 [*Enterococcus faecium* TX1330]; gi|227550716 | rpsG |
| | 50S ribosomal protein L13 [*Enterococcus faecium* 1,230,933]; gi|257880414 | rplM |
| 12 | M20 family peptidase PepV [*Enterococcus faecium* TX1330]; gi|227550917 | pepV |
| | Glutamyl-tRNA synthetase bacterial/mitochondrial [*Enterococcus faecium* DO]; gi|69245495 | gltX |
| | Cell division protein FtsA [*Enterococcus faecium* DO]; gi|69244711 | ftsA |
| | Asparaginyl-tRNA synthetase, class IIb [*Enterococcus faecium* DO]; gi|69247321 | asnC |

In such way, the β-glucuronidase (uidA) gene from *E. coli* was introduced as reporter gene in *Enterococcus faecium* LMG15709. The uidA gene product β-glucuronidase, catalyses the cleavage of a wide variety of β-glucuronides that are commercially available as histochemical and spectrophotometric substrates. As depicted in FIG. 9, dual cistron constructs were made by inserting uidA in the *Enterococcus faecium* LMG15709 chromosome at the 3' end of several endogenous genes (gene X, gap and eno in this example; FIG. 9). Hereby, rpmD of *Enterococcus faecium* was used as intergenic region between the endogenous genes of interest from Table 6 and uidA to identify sites that result in highest β-glucuronidase (GUS) activity (FIG. 10).

*Enterococcus faecium* cultures were grown for 16 hours at 30° C. in GM17 supplemented with thymidine. Cells of 1 ml culture were washed and resuspended in 1 ml demineralized water. Cells were disrupted with MP Biomedicals lysing matrix B and Fasprep-24 device at 6 m/s for 40 seconds. Tubes were centrifuged and a dilution series of the cell supernatant was made. GUS activity was measured by adding p-nitrophenyl substrate and β-mercaptoethanol which gives the solution a yellow colour upon presence of β-glucuronidase. GUS activity was measured at 405 nm and expressed relatively to reference *Lactococcus lactis* strain sAGX0090. All strains were treated in parallel.

Figure 10:
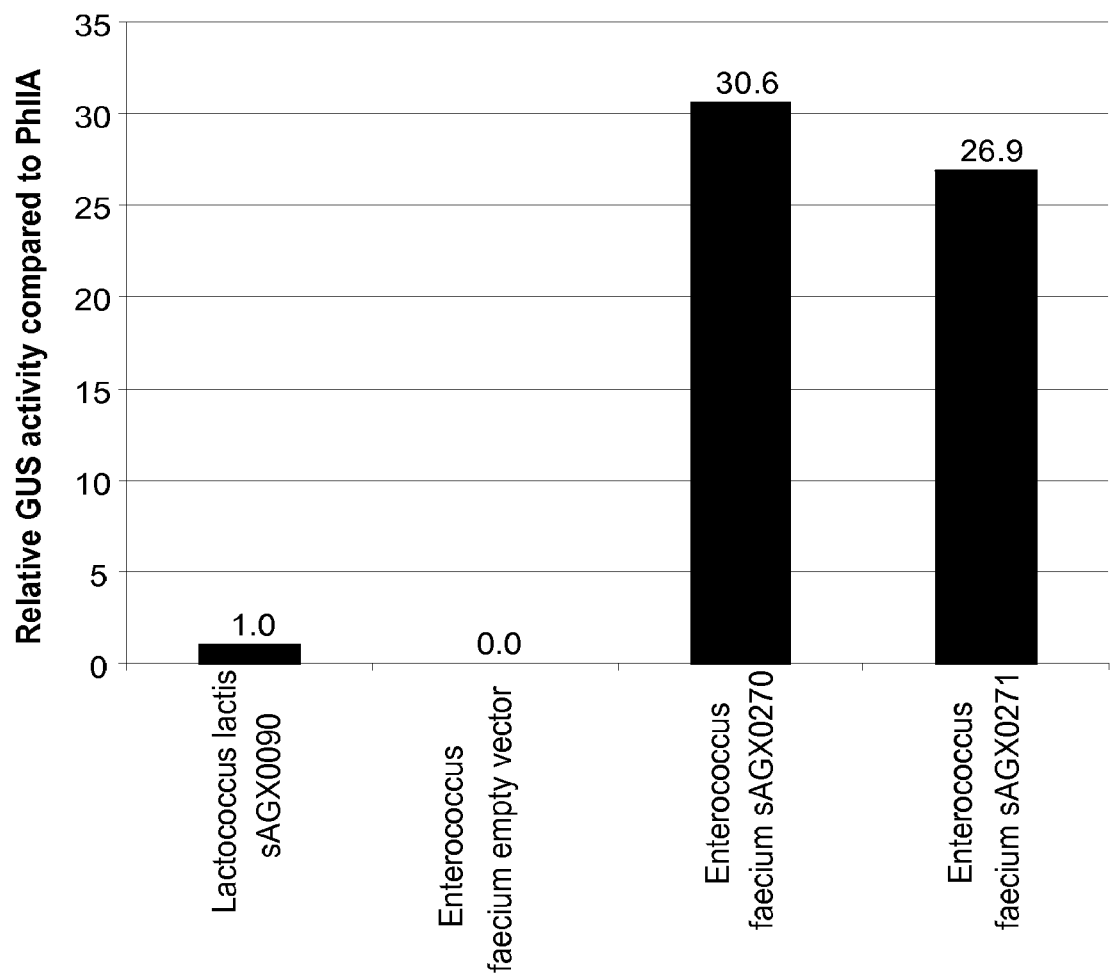
FIG. 10: Relative β-glucuronidase (GUS)-activity in a reference host (monocistronic: PhllA>>uidA, sAGX0090)

FIG. 10 shows relative GUS-activity of gene X>>rpmD>>uidA dual cistron constructs. GUS-activity is expressed relatively to reference strain sAGX0090 that carries the PhllA>>uidA expression cassette and is indicated on the Y-axis. GUS-activity in all dual cistron strains was found to be higher than the reference strain.

In particular, GUS-activity in sAGX0270 (gap>>rpmD>>uidA) and sAGX0271 (eno>>rpmD>>uidA) was found to be 30.6 and 26.9 times higher when compared to sAGX0090, respectively.

These results clearly confirm that bicistronic expression allows enhanced protein expression levels over a wide variety of settings.

Example 9: Bicistronic Expression of Human Interleukin-10 (hIL10) by *Enterococcus faecium*

The DNA coding sequence of the usp45 secretion leader of *Lactococcus lactis* (SS) was fused in frame to the DNA sequence of mature hIL10 to obtain secretion of hIL10. The [SS::hIL10] expression cassette was inserted, along with the rpmD intergenic region of *Enterococcus faecium* preceding SS::hIL10, as a second cistron downstream from gap (sAGX0279; FIG. 11a). The hIL10 secretion capacity was quantified by ELISA to evaluate bicistronic expression of cargo in *Enterococcus faecium*. *Enterococcus faecium* sAGX0270 served as a negative control.

Strains were inoculated from single colony into 10 ml GM17 supplemented with 200 μM thymidine (GM17T)

when needed and grown for 16 hours at 30° C. For the quantification of hIL10 secretion, these saturated overnight cultures were diluted 1/25 in 5 ml fresh GM17T medium and grown for 4 hours at 30° C. Cells were collected by centrifugation at 3220×g for 10 minutes, resuspended in an equal amount BAM9T medium and cultured for another 3 hours at 30° C. BAM9T contains M9 salts, 0.5% aminoplasmal, 0.5% glucose, 25 mM $NaHCO_3$, 25 mM $Na_2CO_3$, 2 mM $MgSO_4$, 0.1 mM $CaCl_2$ and 200 µM thymidine. Cells and culture supernatants were separated by centrifugation at 3220×g for 10 minutes. The amount of secreted human hIL10 in the culture supernatant was quantified by sandwich hIL10 ELISA. All strains were treated in parallel.

FIG. 11b represents the quantification of human hIL10 secretion by *Enterococcus faecium* strains sAGX0270 and sAGX0279 The amount of secreted hIL10 was expressed as $ng/10^9$ CFU cells in 3 hours and indicated on the Y-axis. The figure clearly demonstrates that *Enterococcus faecium* strains comprising a bicistronic expression cassette are able to secrete considerable amounts of the cargo protein hIL10.

Example 10: Bicistronic Expression of Human Interleukin-27 (hIL27) by *Enterococcus faecium*

The DNA coding sequence of the usp45 secretion leader of *Lactococcus lactis* (SS) was fused in frame to the DNA sequence of mature hIL27 to obtain secretion of hIL27. The [SS::hIL27] expression cassette was inserted, along with the rpmD intergenic region of *Enterococcus faecium* preceding SS::hIL27, as a second cistron downstream from gap (sAGX0317; FIG. 12a). The hIL27 secretion capacity was quantified by ELISA to evaluate bicistronic expression of hIL27. *Enterococcus faecium* sAGX0270 served as a negative control, Strains were inoculated from single colony into 10 ml GM17 supplemented with 200 µM thymidine (GM17T) and grown for 16 hours at 30° C. For the quantification of hIL27 secretion, these saturated overnight cultures were diluted 1/25 in 5 ml fresh GM17T medium and grown for 4 hours at 30° C. Cells were collected by centrifugation at 3220×g for 10 minutes, resuspended in an equal amount BM9T medium and cultured for another 3 hours at 30° C. BM9T contains M9 salts, 0.5% casitone, 0.5% glucose, 25 mM $NaHCO_3$, 25 mM $Na_2CO_3$, 2 mM $MgSO_4$, 0.1 mM $CaCl_2$ and 200 µM thymidine. Cells and culture supernatants were separated by centrifugation at 3220×g for 10 minutes. The amount of secreted human hIL27 in the culture supernatant was quantified by sandwich hIL27 ELISA (R&D systems). All strains were treated in parallel.

FIG. 12b represents the quantification of human hIL27 secretion by *Enterococcus faecium* strains sAGX0270 and sAGX0317. The amount of secreted hIL27 was expressed as $ng/10^9$ CFU cells in 3 hours and indicated on the Y-axis. The figure clearly demonstrates that *Enterococcus faecium* strain sAGX0317 comprising a bicistronic expression cassette positioned downstream of the *Enterococcus faecium* gap gene is able to efficiently secrete considerable amounts of the exogenous protein hIL27.

Example 11: Bicistronic Expression of CDP870 Fab by *Enterococcus faecium*

A dual cistron expression constructs was generated with heavy chain and light chain genes of CDP870 Fab. All expression units are located on the bacterial chromosome.

FIG. 13a: CDP870 heavy and light chain Fab fusions to the *Lactococcus lactis* MG1363 usp45 secretion leader (SS) encoding sequences [SS::CDP870 VHCH1] and [SS:: CDP870 VLCL] were inserted as a second and third cistron downstream from the *Enterococcus faecium* LMG15709 gap gene (sAGX0278). In sAGX0278, the intergenic region of *Enterococcus faecium* rpmD was used to couple SS::CD870 expression cassettes to gap. To avoid genetic instability, heavy and light chain genes were coupled through the intergenic region preceding *Lactococcus lactis* rpmD and different codon usage was used in the usp45 secretion signals of the two SS::CD870 expression cassettes The heavy expression cassette precedes the light chain expression cassette in sAGX0278.

For the quantification of CDP870 fab secretion, strains were inoculated from single colony into 10 ml GM17T and grown for 16 hours at 30° C. These saturated overnight cultures were diluted 1/25 in 5 ml fresh GM17T medium and grown for 4 hours at 30° C. Cells were collected by centrifugation at 3220×g for 10 minutes, resuspended in an equal amount BAM9T medium and cultured for another 3 hours at 30° C. BAM9T contains M9 salts, 0.5% aminoplasmal, 0.5% glucose, 25 mM $NaHCO_3$, 25 mM $Na_2CO_3$, 2 mM $MgSO_4$, 0.1 mM $CaCl_2$ and 200 µM thymidine. Cells and culture supernatants were separated by centrifugation at 3220×g for 10 minutes. Crude supernatants from strains carrying the individual constructs were prepared in parallel and were assayed for the presence of TNF binding activity. This was done by direct ELISA using human TNF as capture protein with Cimzia® (CDP870 fab linked to PEG) as a reference standard. CDP870 fab was detected by goat anti-human Fab antiserum and revealed by HRP conjugated donkey anti-goat IgG(H+L) antiserum. HRP activity was visualized by TMB substrate. Reaction was stopped after 30 minutes by adding HCl. Absorbance was measured at 450 nm with 595 nm as reference wavelength. All strains were treated in parallel.

FIG. 13b reveals that both heavy chain and light chains were expressed by the multiple cistron construct in *Enterococcus faecium*, leading to the secretion of functional CDP870 anti-TNF Fab.

Example 12: Anti-hTNF Producing *L. lactis* Bacteria (According to the Invention) Protects Against hTNF-Induced Intestinal Damage in A20IEC-KO Mice Generation of Tissue-Specific A20 Deficient Mice.

Conditional A20/tnfaip3 knockout mice, in which exons IV and V of tnfaip3 gene are flanked by two LoxP sites, were generated as described (Piguet et al., 1999, Lab Invest 79, 495-500). A20 floxed mice were crossed with Villin-Cre transgenic mice generating IEC-specific A20 knockout mice ($A20^{IEC-KO}$) (Madison et al., 2002, J Biol Chem 277, 33275-33283). Experiments were performed on mice back-crossed into the C57BL/6 genetic background for at least four generations.

In Vivo TNF Toxicity.

Mice were injected i.p. with different doses hTNF (50, 10, 8, 6, 4 and 2 µg hTNF/20 g body weight). *E. coli*-derived recombinant hTNF had a specific activity of $6.8 \times 10^7$ IU/mg. Human TNF was produced and purified to homogeneity in our laboratory, and endotoxin levels did not exceed 1 ng/mg of protein. hTNF injection in A20IEC-KO mice induces several pathological and immunological changes that are indicative of intestinal damage. Low dose hTNF does not induce severe systemic effects and lethality, but induces pro-inflammatory cytokine and chemokine expression which can be measured both in serum and homogenates of intestinal tissue. Mice were euthanized after 4 or 5 h for histological analysis. For therapeutic studies, A20$^{IEC-KO}$ mice received anti-TNF producing *L. lactis* bacteria (according to the invention) by oral gavage 5 times (5×10$^{10}$ CFU with 30 min interval) prior to an intraperitoneal injection with hTNF (2 µg and 6 µg hTNF/20 g body weight). Control groups were either treated with the parental *L. lactis* strain MG1363 or with bacterial medium BM9T (vehicle). In addition, a positive control group was treated with a single injection of Remicade (30 mg/kg). Body temperatures were monitored every hour.

Tissue Sample Preparation.

Freshly isolated colonic and ileal segments were flushed with PBS to remove the fecal content and subsequently flushed with formalin (4% formaldehyde in phosphate buffered saline (PBS)) and fixed by incubation overnight in a 10-fold excess of formalin at 4° C. The formalin was removed and intestines were washed twice with PBS prior to embedding in paraffin wax using standard methods.

Histology.

Tissue sections of 4 µm were cut and stained with hematoxylin/eosin using standard techniques. For combined Alcian Blue (AB) and PAS stainings, dewaxed sections were hydrated to distilled water and incubated in Alcian Bleu for 20 min. Sections were subsequently incubated in 1% periodic acid for 10 min followed by incubation in Schiff's reagent for 10 min. Nuclei were counterstained with Mayer's Haematoxylin for 30 sec. Alkaline phosphatase detection was performed by incubation of dewaxed and hydrated tissue sections in NBT/BCIP solution in the dark (70 µl NBT+70 µl BCIP+4860 µl Buffer A, NBT=1.5% Nitroblue Tetrazolium Chloride solution in 70% dimethyl formamide, BCIP=1% 5-bromo-4-Cloro-3-Indolyl Phosphatase in 100% dimethyl formamide, Buffer A=0.1M TrisHCl, 0.1M NaCl, 0.05M MgCl2, pH9.5). For immunochemistry, sections were dewaxed and incubated in Dako antigen retrieval solution and boiled for 20 min in a Pick cell cooking unit and cooled down for 2.5 h. Endogenous peroxidase activity was blocked by immersing slides in peroxidase-blocking buffer buffer (0.040 M citric acid, 0.121 M disodium hydrogen phosphate, 0.030 M sodium azide, 1.5% hydrogen peroxide) for 15 min at room temperature. Blocking buffer (1% bovine serum albumin in PBS) was added to the slides for 30 min at room temperature. Primary antibodies (rabbit anti-lysozyme; 1:1, 750 dilution—Dako; rabbit anti-mucin-2; 1:500 22) were added in blocking buffer and tissue sections were incubated overnight. Secondary antibody was added (polymer horseradish peroxidase-labelled anti-rabbit, Envision) for 30 min at room temperature. Peroxidase was detected by adding diaminobuteric acid (DAB) substrate for 10 min at room temperature and nuclei were counterstained with Mayer's haematoxylin for 2 min. Microscopic measurement of Paneth cell granule radii was done with Leica Image manager 500 software.

Quantification of Cytokines.

Cytokines and chemokines in serum and tissue homogenates were quantified by Cytometric Bead Array kits (CBA) (BD Biosciences) on a FACS Calibur cytometer equipped with CellQuest Pro and CBA software (BD Biosciences).

Quantitative Real-Time PCR.

Ileal segments of 5 cm long were freshly isolated and flushed with PBS to remove the fecal content. One end was ligated and segments were filled with RNA lysis buffer (Aurum Total RNA Mini kit, Bio-Rad Laboratories) and incubated on ice for 5 min. RNA was purified from the lysate solution using the Aurum Total RNA Mini kit (Bio-Rad Laboratories). cDNA synthesis was performed using the iScript cDNA synthesis kit (Bio-Rad Laboratories) according to the manufacturer's instructions. 10 ng cDNA was used for quantitative PCR in a total volume of 10 μl with LightCycler 480 SYBR Green I Master Mix (Roche) and specific primers on a LightCycler 480 (Roche). Real-time PCR reactions were performed in triplicates. The following mouse-specific primers were used: ubiquitin forward, 5'-AGGTCAAACAGGAAGACAGACGTA-3' (SEQ ID NO: 14); and ubiquitin reverse, 5'-TCACACCCAAGAACAAGCACA-3' (SEQ ID NO: 15). Lysozyme-P forward, 5'-GCCAAGGTCTAACAATCGTTGTGAGTTG-3' (SEQ ID NO: 16); Lysozyme-P reverse, 5'-CAGTCAGCCAGCTTGACACCACG-3' (SEQ ID NO: 17); Cryptidin-1 forward, 5'-TCAAGAGGCTGCAAAGGAAGAGAAC-3' (SEQ ID NO: 18); Cryptidin-1 reverse, 5'-TGGTCTCCATGTTCAGCGACAGC-3' (SEQ ID NO: 19).

Statistical Analyses.

Results are expressed as the mean±SEM. Statistical significance between experimental groups was assessed using an unpaired two-sample Student t-Test.

Characterization of Anti-hTNF Producing *L. lactis* Bacteria to Protect Against hTNF-Induced Pathological and Immunological Alterations in A20IEC-KO Mice.

Both control groups injected with 2 μg hTNF showed a more drastic drop in body temperature compared to A20IEC-KO mice treated with anti-hTNF producing *L. lactis* bacteria (FIG. 14*a*, left panel). The protective effect of sAGX0220 treatment observed in mice treated with 2 μg hTNF could no longer be observed when mice were injected with a higher concentration of hTNF (6 μg), whereas Remicade treatment clearly had a protective effect (FIG. 14*a*, right panel). sAGX0220 pretreatment significantly reduced MCP-1, KC and IL-6 levels in ileal and colon homogenates and in serum of mice treated with either 2 μg hTNF, compared to vehicle-treated mice (FIG. 14*b,c*). However, there was a comparable reduction in mice treated with the parental *L. lactis* strain MG1363, indicating that the administration of bacteria on itself can already have a probiotic protective effect. Mice challenged with 6 μg hTNF showed a similar reduction in serum and tissue cytokine and chemokine levels upon sAGX0220 pretreatment, to the same extent as Remicade does (FIG. 14*d,e*). In this setting, however, the protective effect of the parental MG1363 strain is mostly lost (FIG. 14*d,e*).

Example 13: Passive Immunization Against *Clostridium difficile*-Associated Disease with Toxin-Neutralizing Antibodies Locally Produced and Secreted Via *Lactococcus lactis* a) Gene Synthesis of VLCL and VHCH1 of *C. difficile* Toxin A and *C. difficile* Toxin B Neutralizing mAb De novo gene synthesis (optimized for *L. lactis* codon usage) is performed based on the VH and VL amino acid sequence information according to a routine method (Stemmer et al., Gene 1995; 164(1):49-53). This method makes use of synthetic 40-mer oligonucleotides that span the entire coding as well as the non-coding strand, in such way that every oligonucleotide from the coding strand will be 100% complementary with respectively the last and first 20 base pairs of two consecutive oligonucleotides in the non-coding strand, and vice versa.

Genetic information that encodes the secretion leader of *L. lactis* unidentified secreted 45-kDa protein (Usp45) is added to the 5' end of VLCL and VHCH1 genes.

To guarantee coordinated expression, these synthetic VLCL and VHCH1 genes are placed in tandem and joined by the rpmD intergenic region. This leads to the formation of functional VLCL>>VHCH1 operons. Also constructed are variants of the above described synthetic genes that also encode C-terminal E and FLAG peptide tags. This visualizes full size and/or potential degradation products, and enables the verification of light chain and heavy chain assembly and toxin binding.

The resulting gene constructs will be sequence verified.
b) Construction of L. lactis Strains Secreting Toxin A/B Neutralizing Fab: Integration at the Usp45 Locus This task consists of the following stages:
1. Construction of integration vectors for the integration downstream the usp45 locus of
   VLCL>>VHCH1 of C. difficile toxin A neutralizing Mab
   VLCL>>VHCH1 of C. difficile toxin B neutralizing Mab
   3' E and FLAG tagged variants of the above The synthetic VLCL>>VHCH1 operons are flanked at the 5'end by 1 kb of the 3' end of the L. lactis usp45 gene followed by the rplN intergenic region. The VLCL>>VHCH1 operons are flanked at the 3' end by a 1 kb fragment of the 3' downstream flanking region of the L. lactis usp45 gene. Constructions are made by overlap PCR DNA annealing. The resulting plasmids are sequence verified.

2. The above generated integration plasmids are used for integration via translational coupling to the usp45 gene of L. lactis MG1363. Integration is performed by double homologous recombination at both 5' and 3' flanking regions (corresponding to 1 kb regions flanking the 3' end of usp45), and verified by PCR and DNA sequencing.

c) Construction of L. lactis Strains Secreting Toxin A/B Neutralizing Fab: Integration at the enoA Locus This task consists of the following stages:
1. Construction of integration vectors for the integration downstream of the enoA locus of
   VLCL>>VHCH1 of C. difficile toxin A neutralizing Mab
   VLCL>>VHCH1 of C. difficile toxin B neutralizing Mab
   3' E and FLAG tagged variants of the above The synthetic VLCL>>VHCH1 operons from Task 7 are flanked at the 5'end by 1 Kb of the 3' end of the L. lactis enoA gene followed by the rplN intergenic region. The VLCL>>VHCH1 operons are flanked at the 3' end by a 1 Kb fragment of the 3' downstream flanking region of the L. lactis enoA gene. Constructions are made by overlap PCR DNA annealing. The resulting plasmids are sequence verified.

2 The above generated integration plasmids are used for integration via translational coupling to the enoA gene of L. lactis MG1363. Integration is performed by double homologous recombination at both the 5' and 3' flanking regions (corresponding to 1 kb regions flanking the 3' end of enoA), and verified by PCR and DNA sequencing.

d) Establishment of a TopAct™ Compatible Hamster Model of CDAD

The hamster model of CDAD is a well-established model for the study of toxin-induced antibiotic-associated diarrhea and colitis. The most extensively studied model of C. difficile infection in hamsters is the primary challenge model. Briefly, hamsters are pretreated with clindamycin (10-30 mg/kg) orogastrically 24 hours prior to the administration of C. difficile spores to disrupt the normal colonic flora in the hamster. C. difficile spores (e.g. 100 spores of strain 630 or B1; see Goulding et al., Infect Immun 2009; 77(12):5478-5485) are administered orogastrically, and the hamsters are observed (CDAD primary challenge model). Typically, 100% of hamsters succumb to disease between 36 and 72 hours after spore administration. Prior to mortality, symptoms of disease include diarrhea and weight loss. In general, the symptoms are much more severe than those seen in humans, but the hamster model responds to therapeutic maneuvers used in clinical disease, such as treatment with vancomycin, and is therefore widely used in the study of CDAD.

In order to simulate CDAD relapse control, a modified primary disease hamster model is used. Vancomycin protects hamsters from C. difficile disease, as it does in humans. When vancomycin treatment is discontinued, hamsters relapse with severe disease, but the attack rate varies. Briefly, hamsters are given a single dose of clindamycin followed by the orogastric administration of C. difficile strain B1 spores 1 day later. Vancomycin treatment began on the day of spore challenge or 24 hours later and continued daily for two to four subsequent days (CDAD relapse model). This protocol can be further optimized to ensure relapse after rescue with vancomycin.

To assess the benefit of toxin-neutralizing Fab, intestinally delivered by L. lactis, in preventing mortality in the primary and/or relapse model of infection in the hamster, it is important to document the impact of clindamycin and vancomycin on the growth and Fab production capacity of L. lactis. Therefore, in vitro/in vivo studies are performed to determine viability and metabolic activity of the Fab-secreting L. lactis strains.

In vitro evaluation: Fab production (via ELISA) and growth (via plating) from clindamycin/vancomycin-supplemented L. lactis cultures is compared to an antibiotics-free culture and to a culture supplemented with chloramphenicol (Cm) at 5 µg/ml. At this concentration, Cm is a known inhibitor of protein synthesis and growth, to which L. lactis is sensitive.

In vivo evaluation: Fab production (via ELISA) and viability (via plating) is determined in the small/large intestine following oral gavage of hamsters and concomitant treatment with different doses of clindamycin/vancomycin.

These evaluations allow designing and adapting the hamster model (challenge and relapse) of CDAD that is well-suited for the evaluation of the L. lactis delivery system for their preventive and curative effects: this is using (lower) clindamycine (and vancomycine) concentrations and/or a different cocktail of antibiotics demonstrating susceptibility to C. difficile infection without negative effect on L. lactis viability and metabolic activity.

e) Validation of the Hamster Model of CDAD.

In the hamster primary challenge model, Syrian golden hamsters (70 to 80 g) are given different oral doses (qd, bid or tid) of the selected anti-toxin A/B-secreting L. lactis (anti-toxin A and anti-toxin B alone and combined) or 1 ml anti-toxin A/B mAb (as a positive control) intraperitoneally for 4 days beginning 3 days prior to the administration of C. difficile spores. Clindamycin (dose or another cocktail of antibiotics as defined above) is administered orogastrically 24 hours prior to C. difficile spore challenge using a standard small animal feeding needle. Animals are observed for morbidity and mortality, intestinal tissues are scored for histological and macroscopic damage, and C difficile toxin production in luminal contents and feces is determined.

In the hamster relapse model, Syrian golden hamsters (70 to 80 g) are given clindamycin (dose or another cocktail of antibiotics as defined above) orogastrically and 24 hours later challenged with *C. difficile* B1 spores orogastrically. At the time of spore administration or 24 hours later, vancomycin treatment (dose as defined above) orogastrically starts and continues daily for a total of 2-4 days. Beginning 1, 2, 3, 4 or 5 days following vancomycin treatment, different oral doses (qd, bid or tid) of the selected anti-toxin A/B-secreting *L. lactis* (anti-toxin A and anti-toxin B alone and combined) or 1 ml anti-toxin A/B mAb (as a positive control, intraperitoneally) is administered for a total of 5-10 days. Animals are observed for morbidity and mortality, intestinal tissues are scored for histological and macroscopic damage, and *C. difficile* toxin production in luminal contents and feces is determined.

It can be concluded that the gram-positive bacteria according to the invention can effectively be used for immunizing against CDAD. In particular, the gram-positive bacteria according to the invention can prevent the occurrence of CDAD, prevent relapse of CDAD, as well as treat CDAD.

Example 14: Mouth Rinse Powder for Reconstitution

The Drug Substance (DS) of a mouth rinse formulation is a homogeneous, lyophilized powder of an engineered strain according to the invention and mixed with cryoprotectants (dextrin, sorbitol and sodium glutamate).

The production process for the Drug Substance includes the following successive steps: fermentation, biomass concentration (by diafiltration or centrifugation), formulation with cryoprotectants, filling into suitable trays and bulk lyophilization. Homogenization and sieving of the lyophilized cake is performed to produce a homogeneous powder (the Drug Substance) suitable for mixing with excipient and filling into the desired pharmaceutical dosage form.

The mouth rinse Drug Product (DP) powder for reconstitution consists of the freeze-dried *L. lactis* bacteria, mixed with mannitol as an excipient and presented as a (compressed) powder. The clinical formulation is an oral, topical administration in the form of a mouth rinse. This mouth rinse suspension is prepared by reconstitution of the DP into a selected solution.

The production process of the mouth rinse powder for reconstitution includes a series of successive steps:
mixing of Bulk DS with mannitol,
compressing of 500 mg the DP powder mix in 500 mg dispersible powder compacts,
filling of the compressed powder in glass vials,
closing of the vials with tamper-evident, child-resistant screw caps, and
packaging of vials in aluminum (Alu) bags.

Example 15: Bicistronic Expression of CDP870

Dual cistron expression constructs were generated with heavy chain and light chain of CDP870 anti-TNF Fab. All expression units are located on the bacterial chromosome.

FIG. 15 A, schematic overview of CDP870 anti-TNF expression units in various strains: CDP870 light and heavy chain Fab fusions to usp45 secretion leader encoding sequences (SS::CDP870 VLCL and SS::CDP870 VHCH1) were inserted as a second and third cistron downstream from usp45 (sAGX0309, sAGX0319), enoA (sAGX0275) and gapB (sAGX0323, sAGX0326). In these strains, rpmD was used to couple SS::CD870 genes to usp45, enoA or gapB respectively. To avoid genetic instability, light and heavy chain genes were coupled through the intergenic region preceding rplN. In FIGS. 15 B and C 4 identical clones of sAGX0326 (clone 1-4) were analyzed and reported. Strains were processed in parallel throughout the experiments.

For the visualization and quantification of CDP870 anti-hTNF secretion, strains were inoculated from single colony into 10 ml GM17T (Difco™ M17, BD, Sparks, Md., +0.5% glucose+200 µM thymidine) and grown for 16 hours at 30° C. Bacteria from these saturated overnight cultures were collected by centrifugation at 3220×g for 10 minutes and resuspended in 10 ml fresh GM17T medium and grown for 2 hours at 30° C. Bacteria and crude culture supernatants were separated by centrifugation at 3220×g for 10 minutes. Crude supernatants from all strains were prepared in parallel and split up per strain for analysis (FIGS. 15 B and C).

Total protein content of 5 ml volumes of crude culture supernatants was extracted with phenol, precipitated with ethanol and resuspended in SDS-PAGE sample buffer. Equivalents of 1 ml of crude culture supernatants were analyzed by western blot using goat anti-human Fab as a primary antiserum and revealed by rabbit anti-goat AP and NBT/BCIP staining (FIG. 15 B; strains are indicated at the right of respective lanes).

Crude supernatants from strains carrying the individual constructs were assayed for the presence of hTNF binding activity. This was done by direct ELISA using hTNF as capture protein with Cimzia as a reference standard. VLCL portions were detected by goat anti-human IgG antiserum and revealed by horseradish peroxydase (HRP) conjugated anti-goat antiserum. HRP activity was measured by colorimetric assay. Data are presented in FIG. 15 C, strains are indicated underneath respective bars.

FIG. 15 (B and C) reveal that both heavy chain and light chains were highly expressed by the dual cistron constructs, leading to high levels of functional CDP870 anti-TNF Fab. FIG. 15 (B and C) reveals that CDP870 anti-TNF expression slightly increased when heavy and light chain genes were inserted as a second and third cistron downstream from enoA when compared to insertion downstream of usp45. FIG. 15 (B and C) further reveals that CDP870 anti-TNF expression was substantially increased when heavy and light chain genes were inserted as a second and third cistron downstream from gapB when compared to insertion downstream of usp45 or enoA.

For the determination of specific hTNF neutralizing capacity (biological activity per quantity of TNF binding protein), strains were inoculated from single colony into 5 ml GM17T and grown for 16 hours at 30° C. Bacteria from these saturated overnight cultures were collected by centrifugation at 3220×g for 10 minutes and resuspended in 5 ml BM9T medium and grown for 2 hours at 30° C. Bacteria and crude culture supernatants were separated by centrifugation at 3220×g for 10 minutes. Crude supernatants from strains carrying the individual strains were prepared in parallel and split up per strain for analysis (FIGS. 15 D and E).

Crude supernatants from strains carrying the individual constructs were assayed for the presence of TNF binding activity. This was done by direct ELISA using human TNF as capture protein with Cimzia as a reference standard. VLCL portions were detected by goat anti-human IgG antiserum and revealed by horseradish peroxydase (HRP) conjugated anti-goat antiserum. HRP activity was measured by colorimetric assay. All strains were treated in parallel. Data are presented in FIG. 15 D, strains are indicated underneath respective bars.

Crude supernatants from strains carrying the individual constructs were assayed for the presence of TNF neutralizing activity. This was done by incubation of hTNF susceptible WEHI cells with human TNF and addition of anti-TNF. Anti-TNF will scavenge hTNF and will protect WEHI cells from cell death. A ½ dilution series of the crude supernatants as well as reference standard (Cimzia at 63 ng/ml) were added to the cell cultures subjected to hTNF. The impact on cell death was determined. Data are presented in FIG. 15 E, strains are indicated underneath respective bars.

FIG. 15 D reveals that both heavy chain and light chains were highly expressed by the dual cistron constructs, leading to high levels of functional CDP870 anti-TNF Fab. FIG. 15 D further reveals that CDP870 anti-TNF expression substantially increased when heavy and light chain genes were inserted as a second and third cistron downstream from gapB when compared to insertion downstream of usp45.

FIGS. 15 D and E show that specific TNF neutralizing capacity (biological activity per quantity of TNF binding protein) of CDP870 anti-TNF in the crude culture supernatants of strains sAGX0323 and sAGX0326 is identical to that of Cimzia.

Example 16: Efficacy of *L. lactis* Secreting Anti-hTNFα Fab Fragment

The experimental set up is based on the Tg1278TNFko mouse, a transgenic mouse with normally regulated human TNF expression in the absence of mouse TNF (Keffer et al. EMBO. J 10, 4025-4031, 1991). Colitis was induced by rectal administration challenge of 4% TNBS in 40% ethanol after one cutaneous presensitization. Briefly, mice were sensitized 7 days (Day −7) prior intrarectal challenge by applying 1 volume 5% TNBS+4 volumes 4:1 acetone:olive oil to a shaved 1.5×1.5 cm skin area on the back. On the day of the challenge (Day 0), mice were first anesthetized with ketamine/xylazine, subsequently 100 µl 4% TNBS/40% EtOH was administered per rectum by a flexible catheter inserted 4 cm into the rectum. To ensure equal distribution of the enema within the colon, mice were held in a vertical position for 30 seconds directly after the rectal challenge.

Treatment was initiated 1 day before the rectal TNBS challenge (Day −1) and was continued for another 4 days (Day +3). Three groups of mice received once daily intragastric inoculations with $10^{10}$ CFU of MG1363 (negative control), $10^{10}$ CFU sAGX0309, or 10 µg Cimzia (positive control). Starting from Day 0 and on a daily basis, mice were monitored for body weight, morbidity and survival. On Day +3 mice were sacrificed and colon samples and serum were collected for histology (colon) and cytokine (colon and serum) analysis.

Treatment with a strain according to an embodiment of the invention (anti-hTNF-secreting *L. lactis* strain sAGX0309) resulted in an enhanced survival (FIG. 16 and Table 7), in comparison with the wild type *L. lactis* strain MG1363 and surprisingly even a higher survival percentage than mice treated with Cimzia.

TABLE 7

| SURVIVAL | *L. lactis* sAGX0309 | *L. Lactis* MG1363 | Cimzia |
|---|---|---|---|
| Day 1 | 100% (7/7) | 100% (9/9) | 100% (9/9) |
| Day 2 | 86% (6/7) | 89% (8/9) | 89% (8/9) |
| Day 3 | 86% (6/7) | 56% (5/9) | 78% (7/9) |

Body weight of the mice was also followed during treatment, and is depicted in FIG. 17. From FIG. 17, it is evident that weight loss is lower after treatment with a strain according to an embodiment of the invention in comparison with treatment with Cimzia.

The histological status of the colon was also analyzed and a histological score was attributed according to Table 8. The results are indicated in FIG. 18. From FIG. 18, a significant improvement in the histological score, and hence a diminished colitic pathology, is evident after treatment with a strain according to an embodiment of the invention.

TABLE 8

| Histological score | Description |
|---|---|
| 0 | No inflammation; no epithelial dammage |
| 1 | Inflammation in the mucosa around the crypt bases; no epithelial dammage |
| 2 | Inflammation in the submucosa; mild epithelial dammage with loss of goblet cells |
| 3 | Inflammation in the submucosa; local loss of crypt architecture |
| 4 | Inflammation in the submucosa; loss of crypt architecture in extended areas of the mucosa |

Finally, from FIG. 19, it is apparent that treatment with a strain according to an embodiment of the invention resulted in a suppression of colonic proinflammatory cytokine secretion.

The invention claimed is:

1. A recombinant nucleic acid comprising a polycistronic expression unit, wherein said polycistronic expression unit comprises:
   a functional gene endogenous to a Gram-positive bacterium, and
   one or more genes exogenous to said Gram-positive bacterium, which encode a therapeutic product,
   wherein said endogenous gene and said one or more exogenous genes are transcriptionally controlled by a promoter endogenous to said Gram-positive bacterium, wherein said promoter is a ribosomal gene promoter or a glycolysis gene promoter, wherein said endogenous gene and said one or more exogenous genes are transcriptionally coupled by one or more intergenic regions active in said Gram-positive bacterium, and wherein said one or more intergenic regions are preceding rplW, rplP, rpmD, rplB, rpsG, rpsE, rplN, rplM, rplE, or rplF.

2. The recombinant nucleic acid of claim 1, wherein said promoter is the promoter of pyk, eno, pgk, gap (gapA or gapB), tbp, fbaA, rpsD, rpsL, rpsG, rplR, rpsE, rpmD, rplS, rpsK, rplJ, rplL, rpmB, rplD, rplW, rplB, rp10, rplK, rpsH, rplU, rpsM, rpsS, rplU, rplV, rplP, rplN, rpsJ, or rplX of said Gram-positive bacterium.

3. The recombinant nucleic acid of claim 2, wherein said promoter is the promoter of eno, gap, pyk, rpmB, or rplS of said Gram-positive bacterium.

4. The recombinant nucleic acid of claim 1, wherein said one or more exogenous genes are transcriptionally coupled to the 3' end of said endogenous gene.

5. The recombinant nucleic acid of claim 4, wherein one of said one or more exogenous genes is the most 3' gene of said polycistronic expression unit.

6. The recombinant nucleic acid of claim 1, wherein said one or more intergenic regions are endogenous to said Gram-positive bacterium.

7. The recombinant nucleic acid of claim 1, wherein said therapeutic product is:
   (i) an antigen for inducing immunity or immunotolerance,
   (ii) a non-vaccinogenic therapeutically active polypeptide,
   (iii) an antibody or a functional fragment thereof, or
   (iv) a fusion protein or a multimeric protein.

8. The recombinant nucleic acid of claim 7, wherein said therapeutic product is an antibody or a functional fragment thereof.

9. The recombinant nucleic acid of claim 8, wherein one exogenous gene encodes the light chain ($V_L$) of an antibody or of a functional fragment thereof, and another exogenous gene encodes the heavy chain ($V_H$) of the antibody or of a functional fragment thereof.

10. The recombinant nucleic acid of claim 8, wherein said functional fragment is an Fab.

11. The recombinant nucleic acid of claim 9, wherein the exogenous gene encoding said $V_L$ or functional fragment thereof is transcriptionally coupled to the 3' end of the exogenous gene encoding said $V_H$ or functional fragment thereof.

12. The recombinant nucleic acid of claim 8, wherein said one or more exogenous genes encode a single domain antibody.

13. The recombinant nucleic acid of claim 8, wherein said one or more exogenous genes encode an anti-TNFα antibody, an anti-TNFα antibody fragment, or an anti-TNFα single antibody variable domain.

14. The recombinant nucleic acid of claim 1, wherein said one or more exogenous genes encode:
   (i) proinsulin;
   (ii) cA2 anti-TNFα Fab;
   (iii) CDP870 anti-hTNFα Fab;
   (iv) trefoil factor;
   (v) IL-10;
   (vi) IL-27; or
   (vii) an antibody against a toxin from *Clostridium difficile*.

15. The recombinant nucleic acid of claim 1, wherein said Gram-positive bacterium is a lactic acid bacterium or a *Bifidobacterium*.

16. The recombinant nucleic acid of claim 15, wherein said lactic acid bacterium is a *Lactococcus*, a *Lactobacillus*, or an *Enterococcus*.

17. The recombinant nucleic acid of claim 15, wherein said lactic acid bacterium is *Lactococcus lactis* or *Enterococcus faecium*.

18. A vector comprising the recombinant nucleic acid of claim 1.

19. The recombinant nucleic acid of claim 1, wherein the polycistronic expression unit comprises, in 5' to 3' order, (i) an eno promoter as said endogenous promoter, (ii) eno as said functional endogenous gene, and (iii) said one or more exogenous genes.

20. The recombinant nucleic acid of claim 19, wherein said eno and said one or more exogenous genes are transcriptionally coupled by an intergenic region preceding rpmD.

21. The recombinant nucleic acid of claim 1, wherein said Gram-positive bacterium is *Lactococcus lactis*.

22. The recombinant nucleic acid of claim 2, wherein said Gram-positive bacterium is *Lactococcus lactis*.

23. The recombinant nucleic acid of claim 3, wherein said Gram-positive bacterium is *Lactococcus lactis*.

24. The recombinant nucleic acid of claim 4, wherein said Gram-positive bacterium is *Lactococcus lactis*.

25. The recombinant nucleic acid of claim 5, wherein said Gram-positive bacterium is *Lactococcus lactis*.

26. The recombinant nucleic acid of claim 6, wherein said Gram-positive bacterium is *Lactococcus lactis*.

27. The recombinant nucleic acid of claim 7, wherein said Gram-positive bacterium is *Lactococcus lactis*.

28. The recombinant nucleic acid of claim 8, wherein said Gram-positive bacterium is *Lactococcus lactis*.

29. The recombinant nucleic acid of claim 9, wherein said Gram-positive bacterium is *Lactococcus lactis*.

30. The recombinant nucleic acid of claim 10, wherein said Gram-positive bacterium is *Lactococcus lactis*.

31. The recombinant nucleic acid of claim 11, wherein said Gram-positive bacterium is *Lactococcus lactis*.

32. The recombinant nucleic acid of claim 12, wherein said Gram-positive bacterium is *Lactococcus lactis*.

33. The recombinant nucleic acid of claim 13, wherein said Gram-positive bacterium is *Lactococcus lactis*.

34. The recombinant nucleic acid of claim 14, wherein said Gram-positive bacterium is *Lactococcus lactis*.

35. The recombinant nucleic acid of claim 15, wherein said Gram-positive bacterium is *Lactococcus lactis*.

36. The recombinant nucleic acid of claim 16, wherein said lactic acid bacterium is *Lactococcus lactis*.

37. The recombinant nucleic acid of claim 17, wherein said lactic acid bacterium is *Lactococcus lactis*.

38. The vector of claim 18, wherein said Gram-positive bacterium is *Lactococcus lactis*.

39. The recombinant nucleic acid of claim 19, wherein said Gram-positive bacterium is *Lactococcus lactis*.

40. The recombinant nucleic acid of claim 20, wherein said Gram-positive bacterium is *Lactococcus lactis*.

41. The recombinant nucleic acid of claim 1, wherein said one or more intergenic regions are:
   a) a nucleic sequence comprising or consisting of any one of SEQ ID NOs: 1-13;
   b) a nucleic sequence comprising one mismatch, or a deletion or an insertion of one nucleotide as compared to either SEQ ID NO: 2 or SEQ ID NO: 8;
   c) a nucleic sequence comprising one, two, or three mismatches, or a deletion or an insertion of one, two, or three nucleotides as compared to any one of SEQ ID NOs: 3-4 and SEQ ID NOs: 9-10; or
   d) a nucleic sequence comprising one, two, three, or four mismatches, or a deletion or an insertion of one, two, three, or four nucleotides as compared to any one of SEQ ID NOs:
   5-7 and SEQ ID NOs: 11-13.

42. The recombinant nucleic acid of claim 41, wherein said one or more intergenic regions are endogenous to said Gram-positive bacterium.

43. A vector comprising said recombinant nucleic acid of claim 42.

44. The vector of claim 43, wherein said Gram-positive bacterium is *Lactococcus lactis*.

* * * * *

SEQUENCE LISTING

<160> NUMBER OF SEQ ID NOS: 19

<210> SEQ ID NO 1
<211> LENGTH: 5
<212> TYPE: DNA
<213> ORGANISM: Lactococcus lactis

<400> SEQUENCE: 1 taatg     5

<210> SEQ ID NO 2
<211> LENGTH: 9
<212> TYPE: DNA
<213> ORGANISM: Lactococcus lactis

<400> SEQUENCE: 2

-continued

```
taatccatg                                                           9

<210> SEQ ID NO 3
<211> LENGTH: 16
<212> TYPE: DNA
<213> ORGANISM: Lactococcus lactis

<400> SEQUENCE: 3
taaggaggaa aaaatg                                                  16

<210> SEQ ID NO 4
<211> LENGTH: 21
<212> TYPE: DNA
<213> ORGANISM: Lactococcus lactis

<400> SEQUENCE: 4
taatagagga ggaaaatcgt g                                            21

<210> SEQ ID NO 5
<211> LENGTH: 24
<212> TYPE: DNA
<213> ORGANISM: Lactococcus lactis

<400> SEQUENCE: 5
taagaaggga gataagtaag aatg                                         24

<210> SEQ ID NO 6
<211> LENGTH: 24
<212> TYPE: DNA
<213> ORGANISM: Lactococcus lactis

<400> SEQUENCE: 6
taaggaaagg ggtaattaaa catg                                         24

<210> SEQ ID NO 7
<211> LENGTH: 28
<212> TYPE: DNA
<213> ORGANISM: Lactococcus lactis

<400> SEQUENCE: 7
taagcaaaac taggaggaat atagcatg                                     28

<210> SEQ ID NO 8
<211> LENGTH: 5
<212> TYPE: DNA
<213> ORGANISM: Enterococcus faecium

<400> SEQUENCE: 8 taatc                                                               5

<210> SEQ ID NO 9
<211> LENGTH: 17
<212> TYPE: DNA
<213> ORGANISM: Enterococcus faecium

<400> SEQUENCE: 9
taaggaggac aacaata                                                 17

<210> SEQ ID NO 10
<211> LENGTH: 18
<212> TYPE: DNA
<213> ORGANISM: Enterococcus faecium
```

```
<400> SEQUENCE: 10
taataggagg gaatttca                                              18

<210> SEQ ID NO 11
<211> LENGTH: 24
<212> TYPE: DNA
<213> ORGANISM: Enterococcus faecium

<400> SEQUENCE: 11
ttagaagaag gaggaatacc attc                                       24

<210> SEQ ID NO 12
<211> LENGTH: 30
<212> TYPE: DNA
<213> ORGANISM: Enterococcus faecium

<400> SEQUENCE: 12
taaaagttta aggaaggagg gtcttactga                                 30

<210> SEQ ID NO 13
<211> LENGTH: 34
<212> TYPE: DNA
<213> ORGANISM: Enterococcus faecium

<400> SEQUENCE: 13
taatcaagta gaatctacaa ggaggtgtct ttaa                            34

<210> SEQ ID NO 14
<211> LENGTH: 24
<212> TYPE: DNA
<213> ORGANISM: Artificial
<220> FEATURE:
<223> OTHER INFORMATION: Primer

<400> SEQUENCE: 14
aggtcaaaca ggaagacaga cgta                                       24

<210> SEQ ID NO 15
<211> LENGTH: 21
<212> TYPE: DNA
<213> ORGANISM: Artificial
<220> FEATURE:
<223> OTHER INFORMATION: Primer

<400> SEQUENCE: 15
tcacacccaa gaacaagcac a                                          21

<210> SEQ ID NO 16
<211> LENGTH: 28
<212> TYPE: DNA
<213> ORGANISM: Artificial
<220> FEATURE:
<223> OTHER INFORMATION: Primer

<400> SEQUENCE: 16
gccaaggtct aacaatcgtt gtgagttg                                   28

<210> SEQ ID NO 17
<211> LENGTH: 23
<212> TYPE: DNA
<213> ORGANISM: Artificial
<220> FEATURE:
<223> OTHER INFORMATION: Primer

<400> SEQUENCE: 17
```

```
cagtcagcca gcttgacacc acg                                              23

<210> SEQ ID NO 18
<211> LENGTH: 25
<212> TYPE: DNA
<213> ORGANISM: Artificial
<220> FEATURE:
<223> OTHER INFORMATION: Primer

<400> SEQUENCE: 18
tcaagaggct gcaaaggaag agaac                                            25

<210> SEQ ID NO 19
<211> LENGTH: 23
<212> TYPE: DNA
<213> ORGANISM: Artificial
<220> FEATURE:
<223> OTHER INFORMATION: Primer

<400> SEQUENCE: 19
tggtctccat gttcagcgac agc                                              23
```